US007135330B2

(12) United States Patent
Ohtaka

(10) Patent No.: US 7,135,330 B2
(45) Date of Patent: Nov. 14, 2006

(54) NUCLEIC ACID DETECTING CASSETTE, NUCLEIC AND DETECTING APPARATUS UTILIZING NUCLEIC ACID DETECTING CASSETTE, AND NUCLEIC ACID DETECTING SYSTEM UTILIZING NUCLEIC ACID DETECTING CASSETTE

(75) Inventor: Yoshimitsu Ohtaka, Sunto-gun (JP)

(73) Assignees: Kabushiki Kaisha Toshiba (JP); Toshiba Tec Kabushiki Kaisha (JP)

( * ) Notice: Subject to any disclaimer, the term of this patent is extended or adjusted under 35 U.S.C. 154(b) by 0 days.

(21) Appl. No.: 10/994,976

(22) Filed: Nov. 22, 2004

(65) Prior Publication Data

US 2005/0153430 A1 Jul. 14, 2005

(30) Foreign Application Priority Data

Nov. 28, 2003 (JP) ............................ 2003-400878

(51) Int. Cl.
*C12M 1/34* (2006.01)

(52) U.S. Cl. ............................... 435/287.2; 435/287.3; 435/288.5

(58) Field of Classification Search ..................... None
See application file for complete search history.

(56) References Cited

U.S. PATENT DOCUMENTS

| | | | |
|---|---|---|---|
| 5,229,297 A | 7/1993 | Schnipelsky et al. | |
| 5,639,428 A | 6/1997 | Cottingham | |
| 5,863,801 A * | 1/1999 | Southgate et al. | 436/63 |
| 6,929,239 B1 | 8/2005 | Colin et al. | |
| 2003/0214057 A1 | 11/2003 | Huang | |

FOREIGN PATENT DOCUMENTS

| | | |
|---|---|---|
| FR | 2 782 935 | 3/2000 |
| JP | 8-62225 | 3/1996 |
| JP | 2536945 | 7/1996 |
| JP | 2573443 | 10/1996 |
| JP | 9-511407 | 11/1997 |
| WO | WO 00/53320 | 9/2000 |
| WO | WO 01/32930 | 5/2001 |

OTHER PUBLICATIONS

Shoji, S. et al, "Smallest Dead Volume Microvalves for Integrated Chemical Analyzing Systems", IEEE, Jun. 24-27, 1991, pp. 1052-1055.

Vieider, C. et al, "A Pneumatically Actuated Micro Valve with a Silicone Rubber Membrance for Integration with Fluid-Handling Systems", Eurosensors, vol. 2, Jun. 25, 1995, pp. 284-286.

Communication from European Patent Office re: related application.

* cited by examiner

*Primary Examiner*—David Redding
(74) *Attorney, Agent, or Firm*—Harness, Dickey & Pierce, P.L.C.

(57) ABSTRACT

A nucleic acid detecting cassette comprises a fluid holding channel capable of varying the inner volume and holding a reagent, an inlet-outlet port connected to the fluid holding channel and capable of selecting an opened state under which the fluid injection out of the outer portion of the cassette can be achieved and a closed state under which the fluid injection can be interrupted, joining channels connected to the fluid holding channel and capable of selecting an opened state under which the fluid transfer to the other fluid holding channel can be achieved and a closed state under which the fluid transfer can be interrupted, inlet-outlet pads capable of maintaining the inlet-outlet port under a closed state, and joining pads capable of maintaining the joining channels under a closed state.

20 Claims, 67 Drawing Sheets

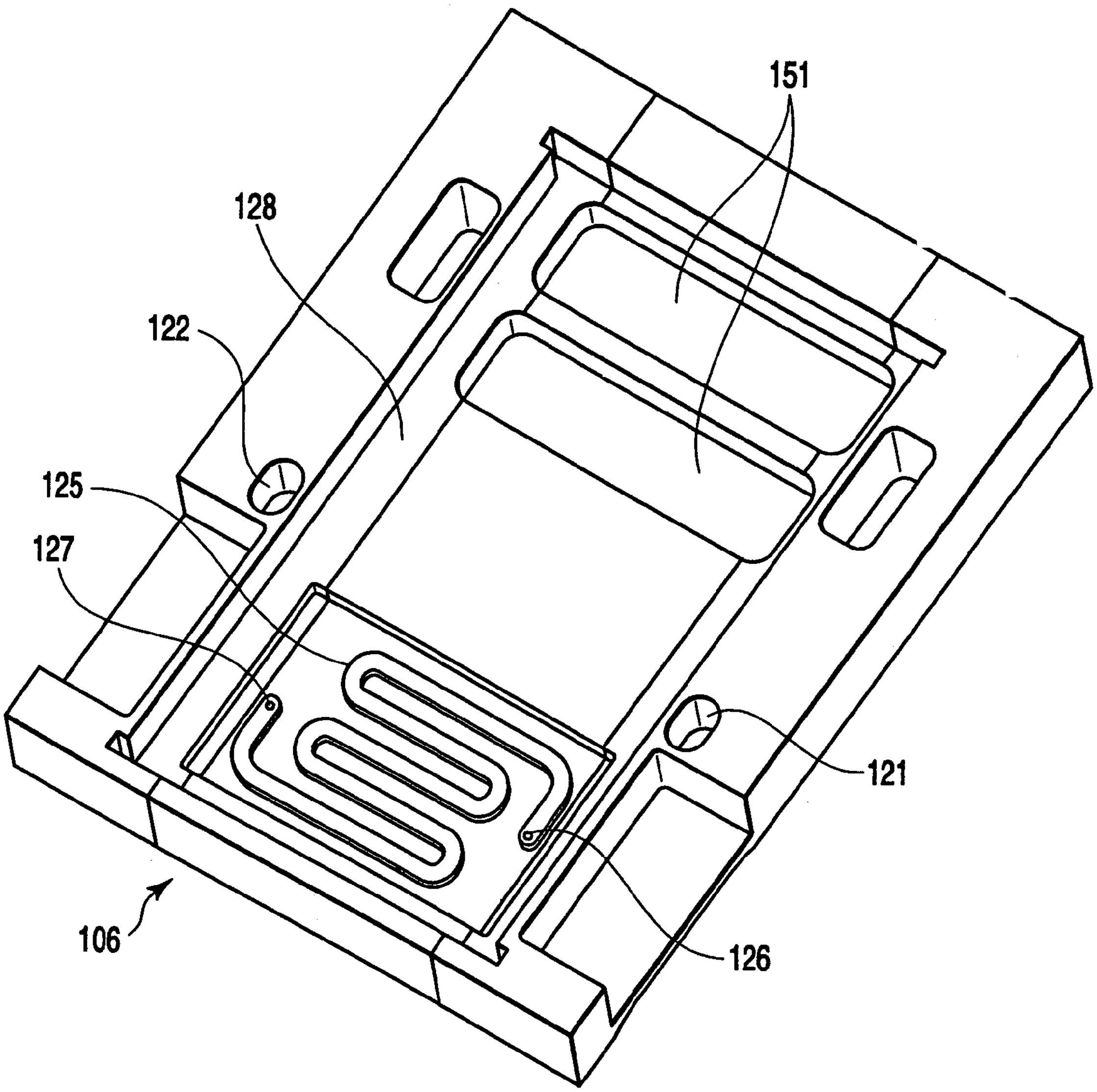
FIG. 40
FIG. 41
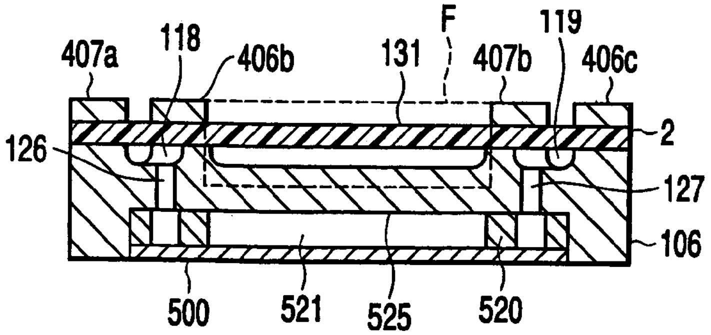

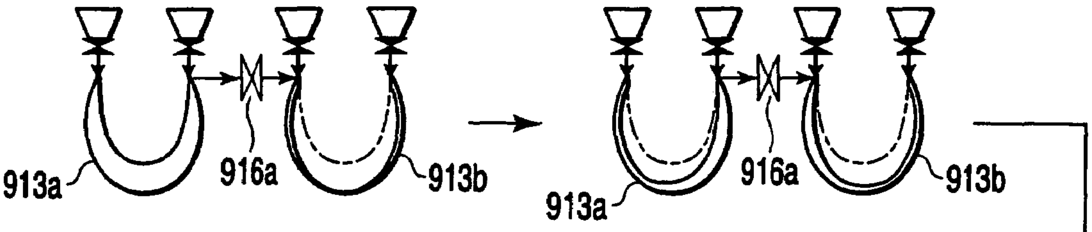
FIG. 81A
FIG. 81B
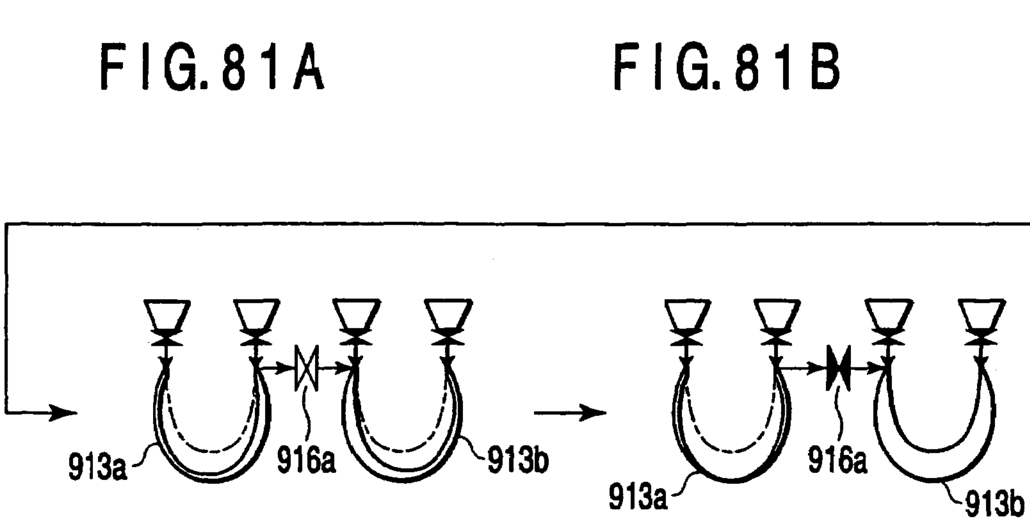
FIG. 81C
FIG. 81D
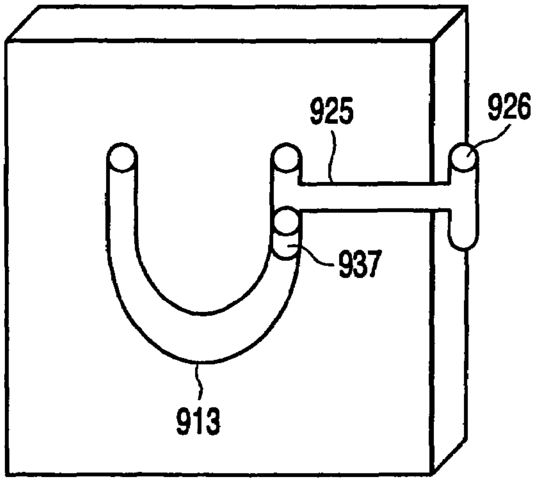
FIG. 82

NUCLEIC ACID DETECTING CASSETTE, NUCLEIC AND DETECTING APPARATUS UTILIZING NUCLEIC ACID DETECTING CASSETTE, AND NUCLEIC ACID DETECTING SYSTEM UTILIZING NUCLEIC ACID DETECTING CASSETTE

CROSS-REFERENCE TO RELATED APPLICATIONS

This application is based upon and claims the benefit of priority from prior Japanese Patent Application No. 2003-400878, filed Nov. 28, 2003, the entire contents of which are incorporated herein by reference.

BACKGROUND OF THE INVENTION

1. Field of the Invention

The present invention relates to a nucleic acid detecting cassette for detecting nucleic acid, a nucleic acid detecting device utilizing the nucleic acid detecting cassette and a nucleic acid detecting system utilizing the nucleic acid detecting device, particularly, to a nucleic acid detecting closed cassette adapted to an automatic successive processing throughout the entire procedure of detecting the target nucleic acid including the step of putting a sample containing nucleic acid into the nucleic acid detecting cassette, the amplification of nucleic acid and other required processing, and the detection of the target nucleic acid, as well as to a nucleic acid detecting deice and a nucleic acid detecting system each utilizing the particular nucleic acid detecting cassette.

2. Description of the Related Art

As a result of the advent of the technology for amplifying nucleic acid and the improvement in the technology for detecting nucleic acid, the detection of a specified DNA strand has come to be propagated. However, in the amplification of nucleic acid, it may be possible for the environment to be contaminated by the amplified nucleic acid. Also, since complex operations relating to, for example, the temperature conditions, the injection of the solution, and the mixing of the solutions are required for the detection of nucleic acid, the detection of nucleic acid by the application of these technologies is limited to that for the testing and the research.

Proposed in, for example, U.S. Pat. No. 5,229,297 is a throwaway type closed detection container in which a series of operations starting with the processing of a sample containing nucleic acid and ending with the detection of the target nucleic acid are automatically carried out in succession. Also disclosed is a detecting apparatus using the particular detection container. The detection container and the detecting apparatus disclosed in the U.S. patent document quoted above are intended to overcome the above-noted problems so as to make it possible to detect nucleic acid in, for example, a hospital, a clinical laboratory, and a quarantine office.

To be more specific, disclosed in the U.S. patent document quoted above is a channel structure in which a series of steps starting with the amplification and ending with the inspection of nucleic acid, which are carried out by utilizing a pouch type cuvette, can be carried out continuously. However, the pouch type cuvette is unstable in shape so as to give rise to the problem that an undesirable entry of air bubbles is unavoidable in the injecting stage of the solution.

BRIEF SUMMARY OF THE INVENTION

An object of the present invention is to provide a nucleic acid detecting closed cassette adapted to an automatic successive processing throughout the entire procedure of detecting the target nucleic acid including the amplification of nucleic acid, other required processing, and the detection of the target nucleic acid, and to provide a nucleic acid detecting device and a nucleic acid detecting system each utilizing the particular nucleic acid detecting cassette.

According to an aspect of the present invention, there is provided a nucleic acid detecting cassette in which a channel is formed by the combination of a stationary member and a flexible member for detecting nucleic acid contained in a sample, wherein:

the cassette comprises:

a fluid holding channel capable of varying the inner volume;

an inlet-outlet port connected to the fluid holding channel and capable of selecting an open-state under which the communication with the outer portion of the nucleic acid detecting cassette can be achieved and a closed-state under which the communication with outside of the nucleic acid detecting cassette can be interrupted;

a joining channel connected to the fluid holding channel and capable of selecting an open-state under which the fluid transfer to the fluid holding channel can be achieved and a closed-state under which fluid transfer to the fluid holding channel can be interrupted;

an inlet-outlet opening-closing means capable of maintaining the inlet-outlet port under the closed-state; and a joining channel opening-closing means capable of maintaining the joining channel under the closed-state.

According to another aspect of the present invention, there is provided a nucleic acid detecting device, comprising the nucleic acid detecting cassette defined above, all necessary reagents loaded in the fluid holding channels of the nucleic acid detecting cassette, and a nucleic acid probe of a single stranded nucleic acid immobilized within the detecting channel of the nucleic acid detecting cassette and having a base sequence complementary to that of nucleic acid to be detected.

Further, according to still another aspect of the present invention, there is provided a nucleic acid detecting system, comprising:

the nucleic acid detecting device defined above;

a device holding means for holding the nucleic acid detecting device;

a first driving mechanism for deforming the flexible member against a first region of the fluid holding channel within the nucleic acid detecting device held by the device holding means so as to deform the fluid holding channel;

a second driving mechanism for deforming the flexible member against a second region of the fluid holding channel within the nucleic acid detecting device held by the device holding means so as to deform the fluid holding channel;

a joining channel opening-closing driving mechanism for driving the joining channel opening-closing means; and a temperature control means for controlling the temperature of the fluid holding channel and the detecting channel.

The present invention relating to the nucleic acid detecting device and the nucleic acid detecting system noted above also constitutes an invention of the method utilizing the nucleic acid detecting device and the nucleic acid detecting system noted above.

BRIEF DESCRIPTION OF THE SEVERAL VIEWS OF THE DRAWING

FIG. 40 is an oblique view schematically showing the detecting section block shown in FIG. 38 as viewed from the back side;

FIG. 41 is a cross sectional view showing the construction of the detecting section block along the line XLI—XLI shown in FIG. 38;

FIGS. 81A to 81D schematically show collectively the solution transfer process in the nucleic acid detecting cassette shown in FIG. 80; and FIG. 82 shows an example of arranging a filter in the fluid holding channel shown in FIGS. 81A to 81D.

DETAILED DESCRIPTION OF THE INVENTION

The nucleic acid detecting cassettes for detecting nucleic acid according to embodiments of the present invention, the nucleic acid detecting device utilizing the particular nucleic acid detecting cassette and the nucleic acid detecting system utilizing the particular nucleic acid detecting device will now be described with reference to the accompanying drawings.

First Embodiment (1) Basic Construction of Cassette:

The basic construction of the nucleic acid detecting cassette for detecting nucleic acid will now be described first with reference to FIGS. 1 and 2.

Figure 1:
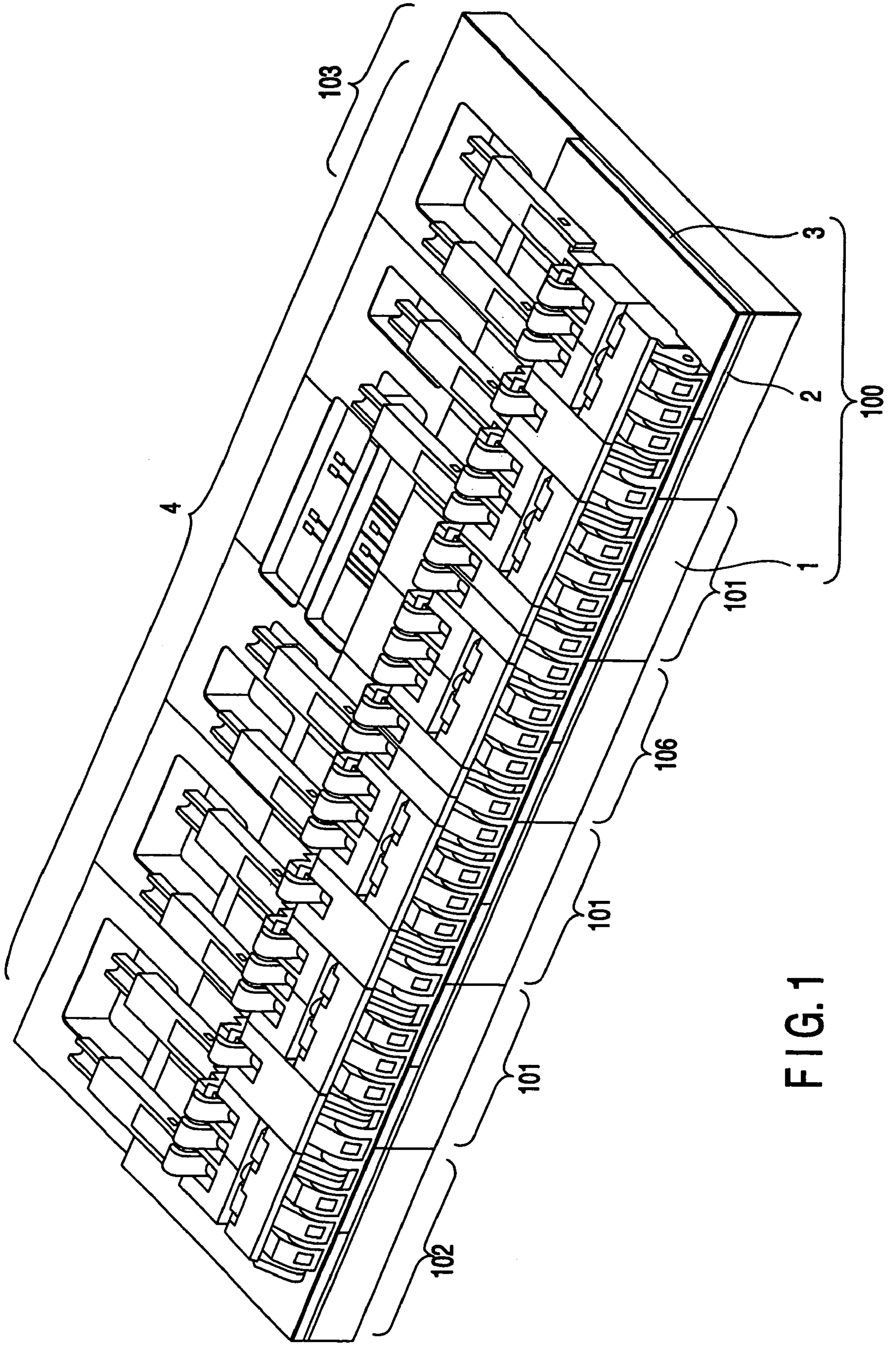
FIG. 1 is an oblique view schematically showing the construction of a nucleic acid detecting cassette according to a first embodiment of the present invention.

(1)-1 Construction of Detecting Cassette:

FIG. 1 is an oblique view schematically showing the outer appearance of a nucleic acid detecting cassette 100 according to the first embodiment of the present invention. As shown in the drawing, the nucleic acid detecting cassette 100 is of a channel closed type, and comprises a stationary base plate 1, a flexible sheet 2 arranged on the stationary base plate 1, and a cover plate 3 arranged on the flexible sheet 2. The stationary base plate 1 is formed of a rigid member, and continuous channels are formed in the stationary base plate 1.

(1)-2 Material of Detecting Cassette:

The flexible sheet 2 is formed of a flexible member and is arranged to cover the upper surface of the channel formed by the stationary base plate 1. Also, the flexible sheet 2 is sandwiched between the cover plate 3 and the stationary base plate 1, and the cover plate 3 is provided with a pushing block 4 for locally pushing and deforming the flexible sheet 2.

The stationary base plate 1 is formed of a polymeric material such as polypropylene, polycarbonate, POM, or PMMA; silicon; glass; ceramic materials; or a metal such as stainless steel, or aluminum. The flexible sheet is formed of a high molecular weight elastomer such as a silicone rubber, a polypropylene rubber or a urethane rubber. Further, the cover plate 3 is formed of a polymeric material such as polypropylene, polycarbonate, POM, or PMMA; or a metal such as silicon, stainless steel or aluminum. Where each of the stationary base plate 1, the flexible sheet 2 and the cover plate 3 is formed of a plurality of parts, it is possible for the materials described above and/or other materials to be selected and combined appropriately so as to form the parts noted above.

(1)-3 Block Structure of Detecting Cassette:

The nucleic acid detecting cassette 100 is separated into a plurality of blocks having the functions described herein later imparted thereto. In the example of the construction shown in FIG. 1, an edge section block 102, two intermediate section blocks 101, a detecting section block 106, another intermediate section block 101, and another edge section block 103 are arranged in the nucleic acid detecting cassette 100 in the order mentioned as viewed from the upstream side of the channel of the sample, i.e., the left side in the drawing, toward the downstream side. The detecting section block 106 is arranged particularly for detecting nucleic acid, and the other blocks, i.e., the edge section blocks 102, 103 and the intermediate section block 101 are arranged for the various reactions other than the detection of nucleic acid. These blocks are joined to each other such that the channels formed on the surfaces of these blocks are connected to each other. These blocks are joined to each other by a fastening member (not shown) or a fastening section (not shown). Incidentally, it is apparent that these blocks can be integrally formed in the form of a single structure.

Figure 2:
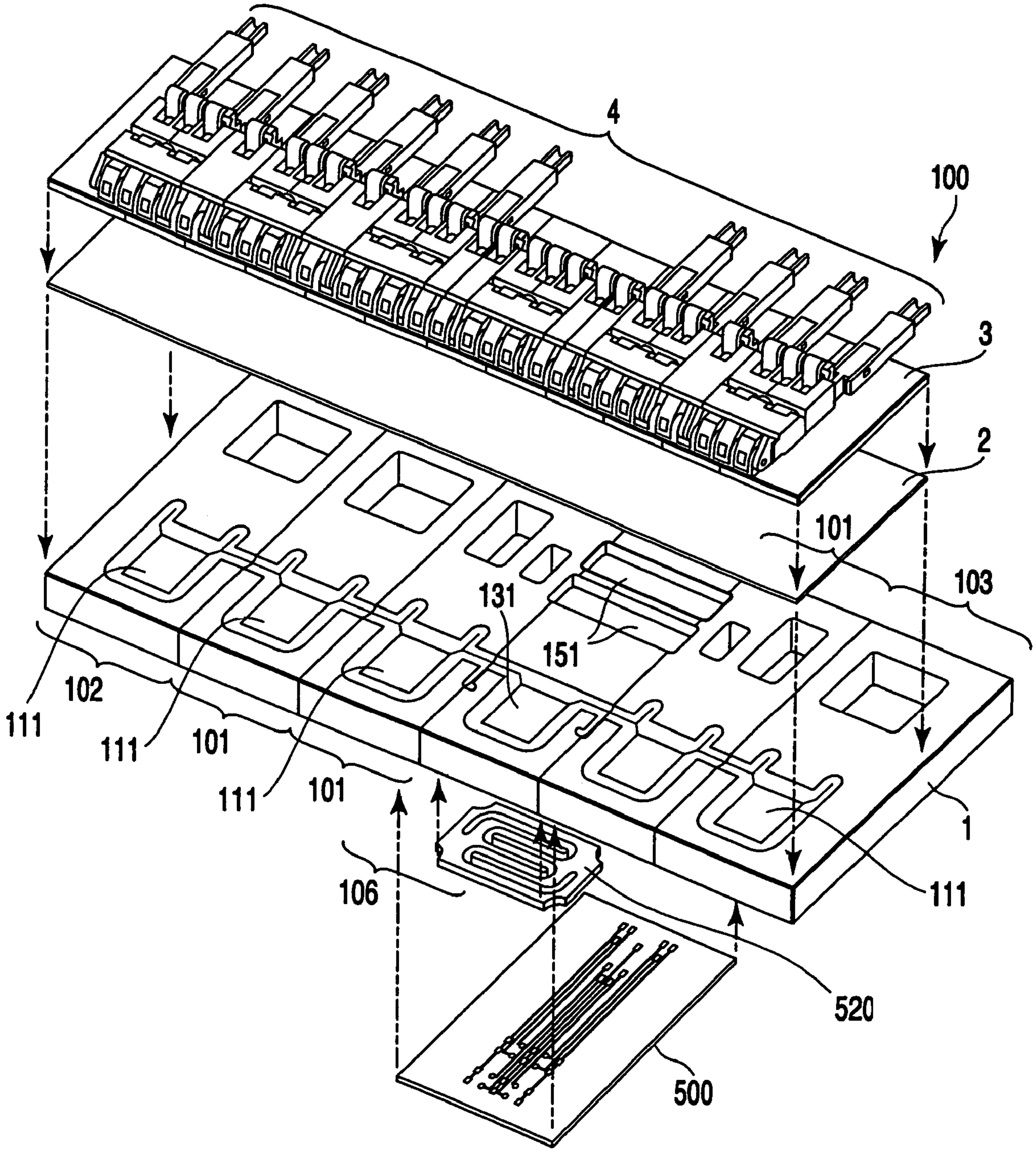
FIG. 2 is an oblique view showing in a dismantled fashion the construction of the nucleic acid detecting cassette shown in FIG. 1.

FIG. 2 is an oblique view showing in a dismantled fashion the nucleic acid detecting cassette 100 shown in FIG. 1. As shown in FIG. 2, channels providing the stationary parts of channels are formed on the upper surface of the stationary base plate 1. Also, the lower surface of the flexible sheet 2 is bonded or welded or contact to the upper surface of the stationary base plate 1 in a manner to cover the channels. It follows that the channels are closed by the flexible sheet 2 so as to define the channels. To be more specific, formed is the channel having the bottom surface and the side surface defined by the stationary base plate 1 and having the upper surface covered with the flexible sheet 2. The channels formed on the edge section block 102 and the intermediate section blocks 101 perform the function of a fluid holding channels 111 serving to hold the fluids. On the other hand, the channel formed on the detecting section block 106 performs the function of a retreating channel 131 serving to permit the fluid to retreat. The fluid holding channels 111 and the retreating channel 131 are connected to each other via a channel. The lower surface of the cover plate 3 is bonded or welded or adhered to the upper surface of the flexible sheet 2. It follows that, if the pushing block 4 arranged on the upper surface of the cover plate 3 pushes the flexible sheet 2, the pushed portion of the flexible sheet 2 is flexed so as to close the channel.

A nucleic acid detecting chip 500 for detecting nucleic acid is held stationary on the lower surface of the detecting section block 106.

A detecting channel seal 520 is sandwiched between a nucleic acid detecting chip 500 and the lower surface of the detecting section block 106 in a manner to form the channel for the detection. Also, two contact point openings 151 extending from the front surface to reach the back surface are formed in the detecting section block 106. An electric connector (not shown) is inserted into the contact point opening 151 so as to be brought into contact with the exposed surface of the nucleic acid detecting chip 500, with the result that an electric signal generated from the chip surface is output from the electric connector.

(2) Channel and Pushing Mechanism:

The construction that permits the pushing block 4 to deform the flexible sheet 2 so as to vary the inner volumes in the desired portions of the channel and the operation of the particular construction will now be described with reference to FIGS. 3 to 28.

Figure 3:
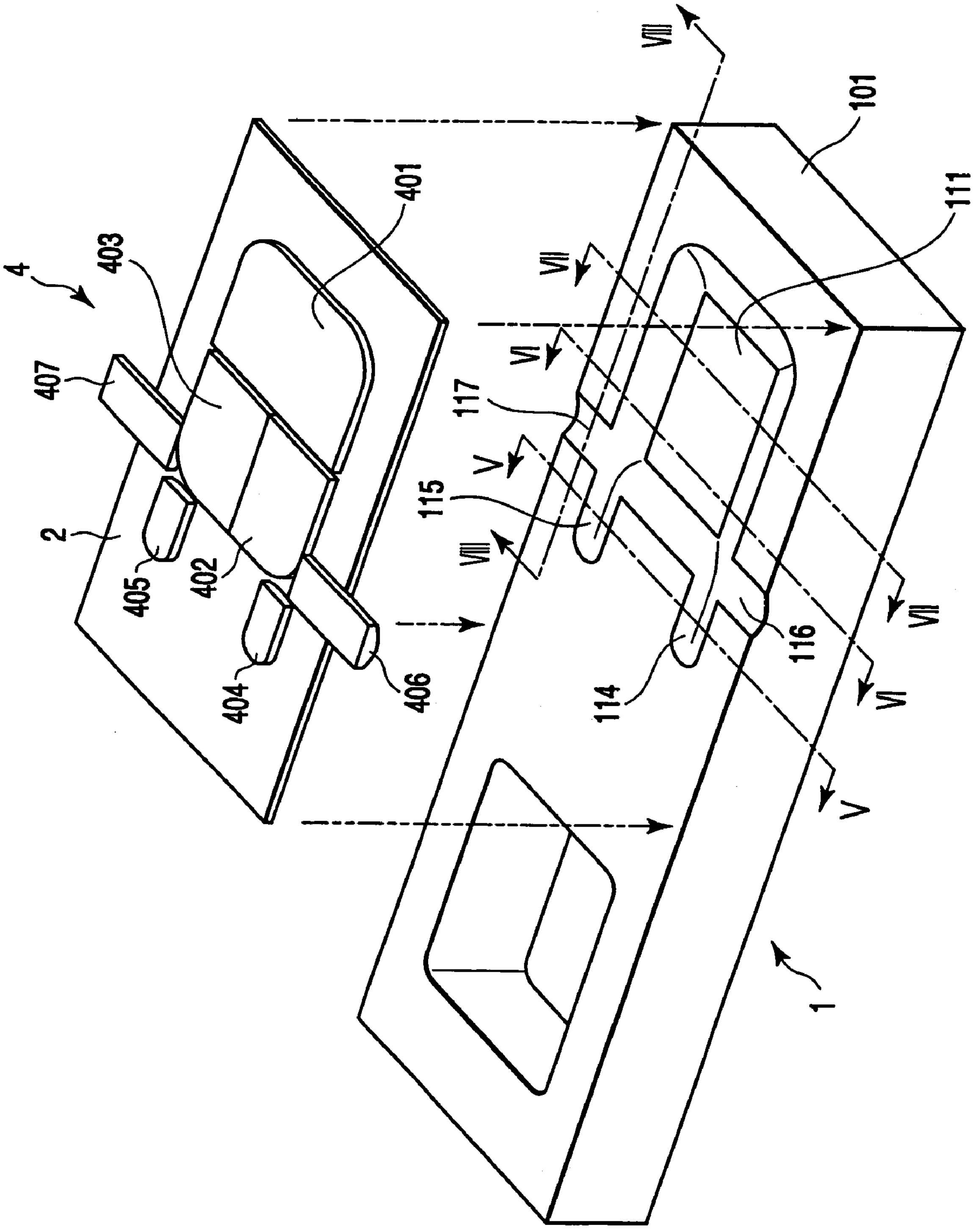
FIG. 3 is an oblique view partly broken away and showing the construction of the intermediate section block shown in FIG. 2.

(2)-1 Intermediate Section Block 101:

FIG. 3 is an oblique view partially showing the construction of the intermediate section block 101, which is separated from the other blocks. As shown in FIG. 3, inlet-outlet channels 114 and 115 are connected, respectively, to the starting edge section of the channel and the terminating edge section of the channel of the fluid holding channel 111 that is shaped substantially rectangular. These inlet-outlet channels 114 and 115 are arranged for injecting a reagent and a sample containing nucleic acid into the nucleic acid detecting cassette 100 or discharging the reagent and the sample to the outside of the nucleic acid detecting cassette 100. Also, a joining channel 116 is connected to the channel starting edge section, and another joining channel 117 is connected to the channel terminating edge section. These joining channels 116 and 117 extend to reach the periphery of the intermediate section block 101 and can be joined to a channel formed in another adjacent block joined to the intermediate section 101. These joining channel 116, fluid holding channel 111, and joining channel 117 are connected to each other in the order mentioned so as to form a large channel. To be more specific, a liquid material or a gaseous material, which are hereinafter referred to simply as fluid, from another block is transferred through one of the joining channels 116 and 117 into the fluid holding channel 111. Also, it is possible to transfer the fluid within the fluid holding channel 111 into another block through one of the joining channels 116 and 117.

(2)-2 Edge Section Blocks 102, 103 and Detecting Section Block 106

Figure 4:
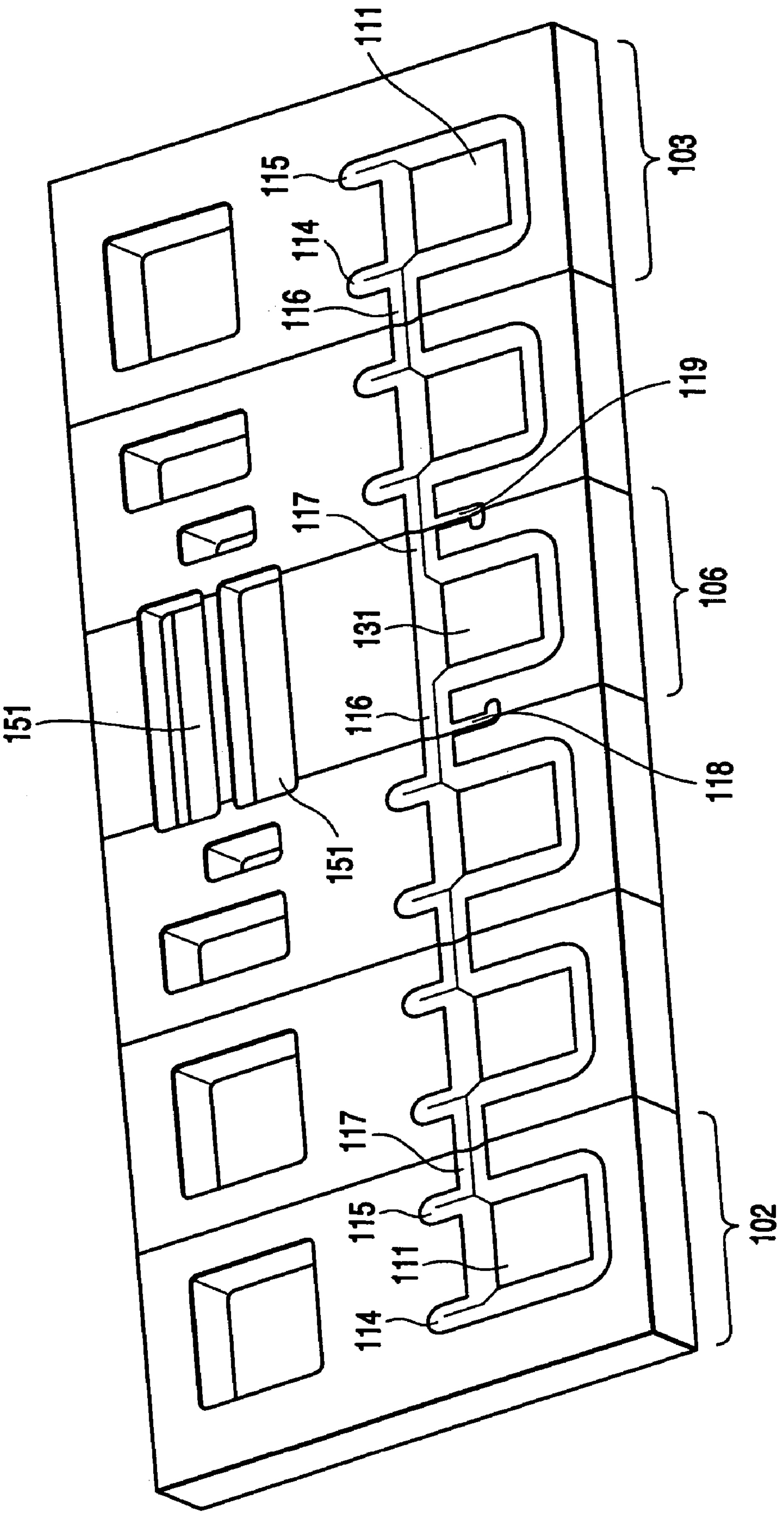
FIG. 4 is an oblique view showing in detail the construction of each of the intermediate section block, the edge section block and the detecting section block shown in FIG. 2.

FIG. 4 is an oblique view showing in detail the constructions of the intermediate section block 101, the edge section blocks 102, 103 and the detecting section block 106.

Like the intermediate section block 101, the edge section block 102 is provided with a substantially rectangular fluid holding channel 111 for holding the fluid. Also, inlet-outlet channels 114 and 115 are connected, respectively, to a channel starting edge section and a channel terminating edge section of the fluid holding channel 111, and a joining channel 117 is further connected to the channel terminating section. Unlike the intermediate section block 101, the edge section block 102 is not provided at the channel starting edge section with a joining channel that is joined to the channel of another block.

The detecting section block 106 is provided with a substantially rectangular retreating channel 131 for retreating the fluid in place of the fluid holding channel 111. The retreating channel 131 has a construction substantially equal to that of the fluid holding channel 111. Joining channels 116 and 117 are connected, respectively, to the channel starting edge section and the channel terminating edge section of the retreating channel 131, and an inlet-outlet channel is not formed in the retreating channel 131. Also, a channel 118 is further connected to the joining channel 116, and a channel 119 is further connected to the joining channel 117. These channels 118 and 119 are connected, respectively, to a left side guide hole 126 (not shown) and a right side guide hole 127 (not shown). A left side guide hole 126 and a right side guide hole 127 are formed to extend to reach the back surface of the detecting section block 106). The detecting channel formed on the back surface of the detecting section block 106 is connected to the channels 118 and 119 via the left side guide hole 126 and the right side guide hole 127 noted above. It follows that the fluid is allowed to be transferred between the retreating channel 131 and the detecting channel.

Like the intermediate section block 101, the edge section block 103 is provided with a substantially rectangular fluid holding channel 111 for holding the fluid. Inlet-outlet channels 114 and 115 are connected, respectively, to the channel starting edge section and channel terminating edge section of the fluid holding channel 111. Further, the joining channel 116 is connected to the channel starting edge section noted above. However, unlike the intermediate section block 101, the edge section block 103 is not provided with a joining channel at the channel terminating edge section.

(2)-3 Main Dimensions and Shapes of Channel:

The dimensions of each of the constituents of the blocks shown in FIGS. 3 and 4 are as follows.

Each of the fluid holding channel 111 and the retreating channel 131 has a depth of about 0.5 mm, a length toward the adjacent channel, i.e., the length between the channel starting edge section and the channel terminating edge section, of about 10 mm, a length in a direction perpendicular to the direction toward the adjacent channel, i.e., the width of the channel, of about 10 mm, and a standard holding inner volume of about 40 μl (micro-liters) to 48 μl. In the construction that the pushing block 4 opens outward, the flexible sheet 2 is capable of expansion outward, with the result that it is possible for each of the fluid holding channel 111 and the retreating channel 131 to keep a holding inner volume that is about 2 to 3 times as large as the standard holding inner volume noted above. Incidentally, the retreating channel 131 is kept shrunk before initiation of the nucleic acid detecting operation so as to have a small inner volume, and the inner volume of the retreating channel 131 can be expanded at the initiating stage of the detecting operation. It should be noted that the difference in the inner volume of the retreating channel 131 between the expanded stage and the shrunk stage is set to a level not smaller than the volume of the fluid loaded in the detecting channel.

Each of the inlet-outlet channels 114 and 115 has a depth of about 0.25 mm, a length toward the fluid holding channel of about 2 to 3 mm, and a length in a direction perpendicular to the direction toward the fluid holding channel, i.e., the width of the channel, of about 2 mm. It is possible to set each of the inlet-outlet channels 114 and 115 in a manner to form a completely closed state such that the inner volume of each of the inlet-outlet channels 114 and 115 is substantially zero.

Each of the joining channels 116 and 117 has a depth of about 0.25 mm, a length toward the adjacent channel of about 2 to 3 mm, and a length in a direction perpendicular to the direction toward the fluid holding channel, i.e., the width of the channel, of about 2 mm. It is possible to set each of the joining channels 116 and 117 in a manner to form a completely closed state such that the inner volume of each of the joining channels 116 and 117 is substantially zero.

It should be noted that the walls defining the channel, which extend from the bottom surface to the side surface of the channel, are smoothly curved so as to make it possible to set up the state that, even when the flexible sheet 2 is flexed, an internal overstress is not generated and the flexible sheet 2 can be brought into a tight contact without fail with the bottom surface of the channel such that the inner volume of the channel can be made substantially zero.

The flexible sheet 2 has a thickness of 0.2 to 0.5 mm, and can be formed of a relatively hard material having a rubber hardness of JIS-A20° to 30° or a relatively soft material having a rubber hardness of Asker C20° to 40°.

(2)-4 Pushing Pad:

FIG. 3 also shows the pushing member, i.e., the pushing block 4 separated from the stationary base plate 1 before the pushing block 4 is bonded to the stationary base plate 1, together with the flexible sheet 2. Incidentally, FIG. 3 shows a pad alone as a part of the pushing block 4 so as to facilitate the description. The flexible sheet 2 and the pushing block 4 are arranged on the other blocks as well as on the intermediate section block 101. It should be also noted, however, that those portions of the flexible sheet 2 and the pushing block 4 which are positioned on the other blocks are omitted from the drawing, and FIG. 3 selectively shows the flexible sheet 2 and the pushing block 4 positioned on the intermediate section block 101. The fluid holding channel 111, the inlet-outlet channels 114, 115, and the joining channels 116 and 117 are arranged in the intermediate section block 101. The flexible sheet 2 covers the opening of each of these channels so as to form a closed channel. Also, a plurality of pads is arranged on the flexible sheet 2.

A central pad 401, a left side pad 402, and a right side pad 403 are arranged on that region of the flexible sheet 2 which is positioned to face the fluid holding channel 111. The left side pad 402 and the right side pad 403 are arranged, respectively, on the upper portions of the channel starting edge section and the channel terminating edge section of the fluid holding channel 111 and in the vicinity of the upper portions noted above. On the other hand, the central pad 401 is arranged to face that region of the fluid holding channel 111 in which the width of the channel is broadened. In addition, the central pad 401 is positioned in contact with the left side pad 402 and the right side pad 403. The upper portion of the fluid holding channel 111 is substantially covered with these pads 401, 402 and 403. In the example of the construction shown in FIG. 3, the left side pad 402 and the right side pad 403 are substantially equal to each other in area, and the central pad 401 is set to have an area substantially equal to the sum of the areas of the left side pad 402 and the right side pad 403.

A left side inlet-outlet pad 404 and a right side inlet-outlet pad 405 are arranged, respectively, above the upper portions of the inlet-outlet channels 114 and 115.

Also, a left side joining pad 406 and a right side joining pad 407 are arranged on the upper portions of the joining channels 116 and 117, respectively.

Each of these pads is shaped to permit the flexible sheet 2 to be brought into a tight contact with the corresponding channel formed in the stationary base plate 1 so as to decrease the inner volume of the channel to substantially zero when the flexible sheet 2 is pushed substantially in the vertical direction from the front surface toward the stationary base plate 1.

Figure 5A:
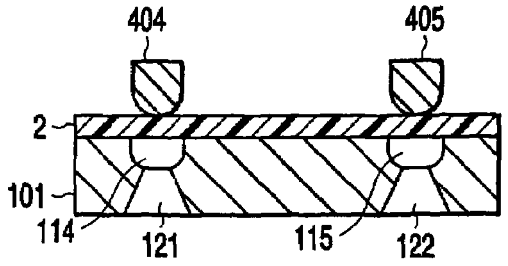
FIGS. 5A and 5B are cross sectional views each showing the construction of the gist portion of the intermediate section block along the line V—V shown in FIG. 3.
Figure 5B:
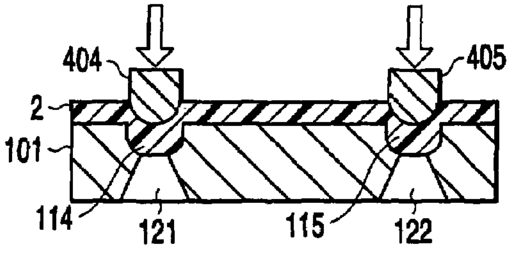

(2)-5 Channel Cross Sectional Mechanism:

FIGS. 5A and 5B are partial cross sectional views of the intermediate section block 101 along the line V—V shown in FIG. 3 and show in detail the construction of the inlet-outlet section for the fluids. To be more specific, FIG. 5A shows the opened state of the channel, and FIG. 5B shows the closed state of the channel. The inlet-outlet channels 114 and 115 are joined to opening portions 121 and 122, respectively, on the side of the bottom surface. The opening portions 121 and 122 are formed to extend to reach the back surface of the stationary base plate 1. It is possible to inject a reagent and sample, etc. from outside into the inlet-outlet channels 114 and 115 through the opening portions 121 and 122, respectively.

As shown in FIG. 5A, under the state that the left side inlet-outlet pad 404 and the right side inlet-outlet pad 405 are not pushed toward the flexible sheet 2, the inlet-outlet channels 114, 115 and the opening portions 121, 122 permit the fluid such as a reagent to be transfer between the outside of the nucleic acid detecting cassette 100 and the inside of the channel. On the other hand, under the state that the left side inlet-outlet pad 404 and the right side inlet-outlet pad 405 are pushed toward the flexible sheet 2 in a direction denoted by an arrow by an external driving force as shown in FIG. 5B, the flexible sheet 2 is deformed so as to close the flow within the inlet-outlet channels 114 and 115, with the result that the transfer of the fluid is broken between the outside of the nucleic acid detecting cassette 100 and the inside of the channel.

Figure 6A:
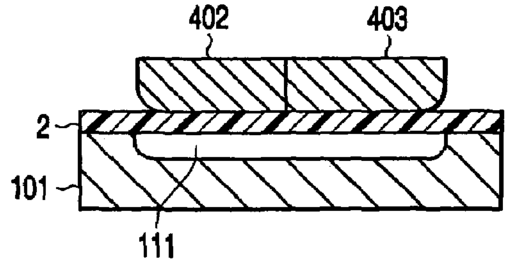
FIGS. 6A, 6B and 6C are cross sectional views each showing the construction of the gist portion of the intermediate section block along the line VI—VI shown in FIG. 3.
Figure 6B:
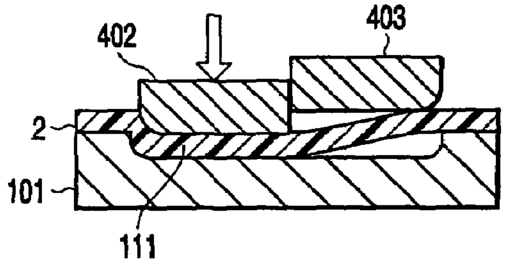
Figure 6C:
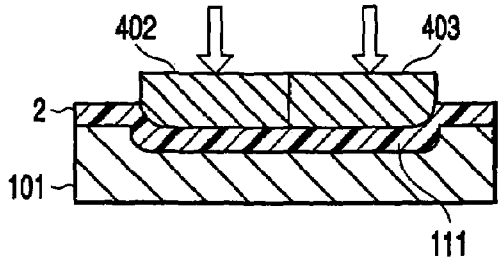

FIGS. 6A to 6C are partial cross sectional views of the intermediate section block 101 along the line VI—VI shown in FIG. 3 and show in detail the construction in the vicinity of the joining channels 116 and 117. To be more specific, FIG. 6A shows the opened state of the channel, FIG. 6B shows the half opened state of the channel, and FIG. 6C shows the closed state of the channel.

As shown in FIG. 6A, under the state that the left side pad 402 and the right side pad 403 are not pushed toward the flexible sheet 2, it is possible for the fluid to be held in the space defined between the bottom surface of the fluid holding channel 111 and the flexible sheet 2. As shown in FIG. 6B, under the state that the left side pad 402 is pushed toward the flexible sheet 2 by an external driving force (not shown) and the right side pad 403 is not pushed into the flexible sheet 2, the flexible sheet 2 is deformed so as to close the channel starting edge section on the left side portion of the fluid holding channel 111. In this case, the inner volume of the channel defined between the bottom surface of the fluid holding channel 111 and the flexible sheet 2 is decreased to about half the inner volume under the state shown in FIG. 6A. Also, under the state that the right side pad 403 alone is pushed toward the flexible sheet 2, the inner volume of the channel noted above is similarly decreased. Further, as shown in FIG. 6C, under the state that both the left side pad 402 and the right side pad 403 are pushed toward the flexible sheet 2 by an external driving force, the flexible sheet 2 is deformed so as to make it possible to close the region in the vicinity of the channel terminating edge section on the right side portion of the fluid holding channel 111. In this case, it is possible to decrease the inner volume of the channel in the vicinity of the joining channels 116 and 117 and defined between the bottom surface of the fluid holding channel 111 and the flexible sheet 2 to substantially zero, and it is possible to decrease the inner volume of entire channel of the fluid holding channel 111 to about ¼.

Figure 7A:
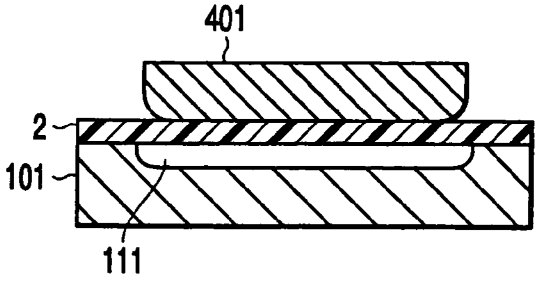
FIGS. 7A and 7B are cross sectional views each showing the construction of the gist portion of the intermediate section block along the line VII—VII shown in FIG. 3.
Figure 7B:
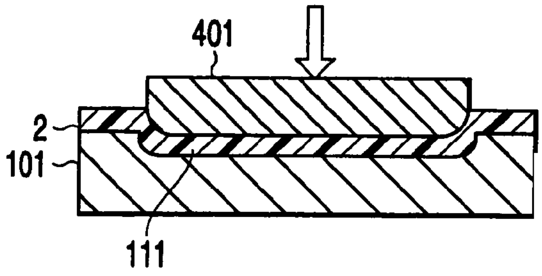

FIGS. 7A and 7B are partial cross sectional views of the intermediate section block 101 along the line VII—VII shown in FIG. 3 and show in detail the construction of the region remote from the joining channels 116 and 117. To be more specific, FIG. 7A shows the opened state of the channel, and FIG. 7B shows the closed state of the channel. As shown in FIG. 7A, under the state that the central pad 401 is not pushed toward the flexible sheet 2, it is possible to hold the fluid within the space defined between the bottom surface of the fluid holding channel 111 and the flexible sheet 2. Also, as shown in FIG. 7B, under the state that the central pad 401 is pushed by an external driving force (not shown) in the direction denoted by an arrow, the flexible sheet 2 is deformed so as to close the fluid holding channel 111. In this case, it is possible to decrease the inner volume of the channel remote from the joining channels 116 and 117 and defined between the bottom surface of the fluid holding channel 111 and the flexible sheet 2 to substantially zero, and it is possible to decrease the inner volume of entire channel of the fluid holding channel 111 to about ¼.

Figure 8A:
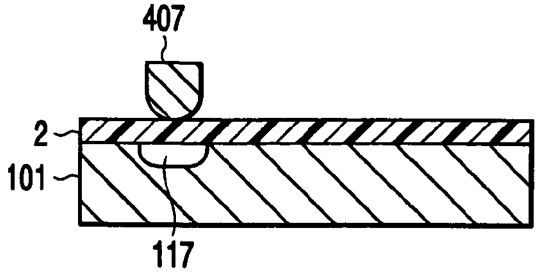
FIGS. 8A and 8B are cross sectional views each showing the construction of the gist portion of the intermediate section block along the line VIII—VIII shown in FIG. 3.
Figure 8B:
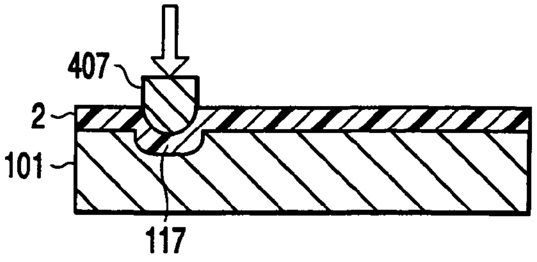

FIGS. 8A and 8B are partial cross sectional views of the intermediate section block 101 along the line VIII—VIII shown in FIG. 3 and show in detail the construction of the joining channel 117. To be more specific, FIG. 8A shows the opened state of the channel, and FIG. 8B shows the closed state of the channel. As shown in FIG. 8A, under the state that the right side joining pad 407 is not pushed toward the flexible sheet 2, it is possible to transfer and hold the fluid in the space defined between the bottom surface of the joining channel 117 and the flexible sheet 2. Also, as shown in FIG. 8B, under the state that the right side joining pad 407 is pushed in the direction denoted by an arrow by an external driving force (not shown), the flexible sheet 2 is deformed so as to close the flow within the joining channel 117. In this case, the inner volume of the channel defined between the bottom surface of the joining channel 117 and the flexible sheet 2 can be decreased to substantially zero. Also, the inner volume of the channel can also be varied similarly in respect of the joining channel 116.

Needless to say, the inner volume of the retreating channel 131 can also be varied similarly like the fluid holding channel 111 described previously with reference to FIGS. 6A to 8B.

(2)-6 Opening-Closing Mechanism of Pushing Block 4:

(2)-6-1 Basic Structure of Pushing Block:

The related motions of the parts of the pushing block 4 and the cover plate 3 shown in FIGS. 1 and 2 will now be described with reference to FIGS. 9 to 28. In the following description, the opening-closing mechanism of the pushing block 4 is described with the intermediate section 101 taken as an example.

Various methods can be applied for the movement and fixation of the pushing pads 401 to 408. In the nucleic acid detecting cassette according to the first embodiment of the present invention, employed is the construction comprising a movable rod having a single fulcrum and a locking section for temporarily fixing the edge section of the movable rod, as described in the following.

FIGS. 9 to 16 are oblique views showing in detail the construction of the pushing block 4 and show different opened and closed states. FIG. 17 is an oblique view schematically showing in a dismantled fashion the constructions of the constituting members of the pushing block 4.

As shown in FIG. 17, a central rod 411, a left side rod 412, a right side rod 413, movable rods 414, 415, and movable rods 416, 417 are arranged as the movable rods in the pushing block 4. A central pad 401, a left side pad 402, a right side pad 403, a left side inlet-outlet pad 404, a right side inlet-outlet pad 405, a left side joining pad 406 and a right side joining pad 407 are formed integrally in the movable rods 411 to 417, respectively.

Figure 9:
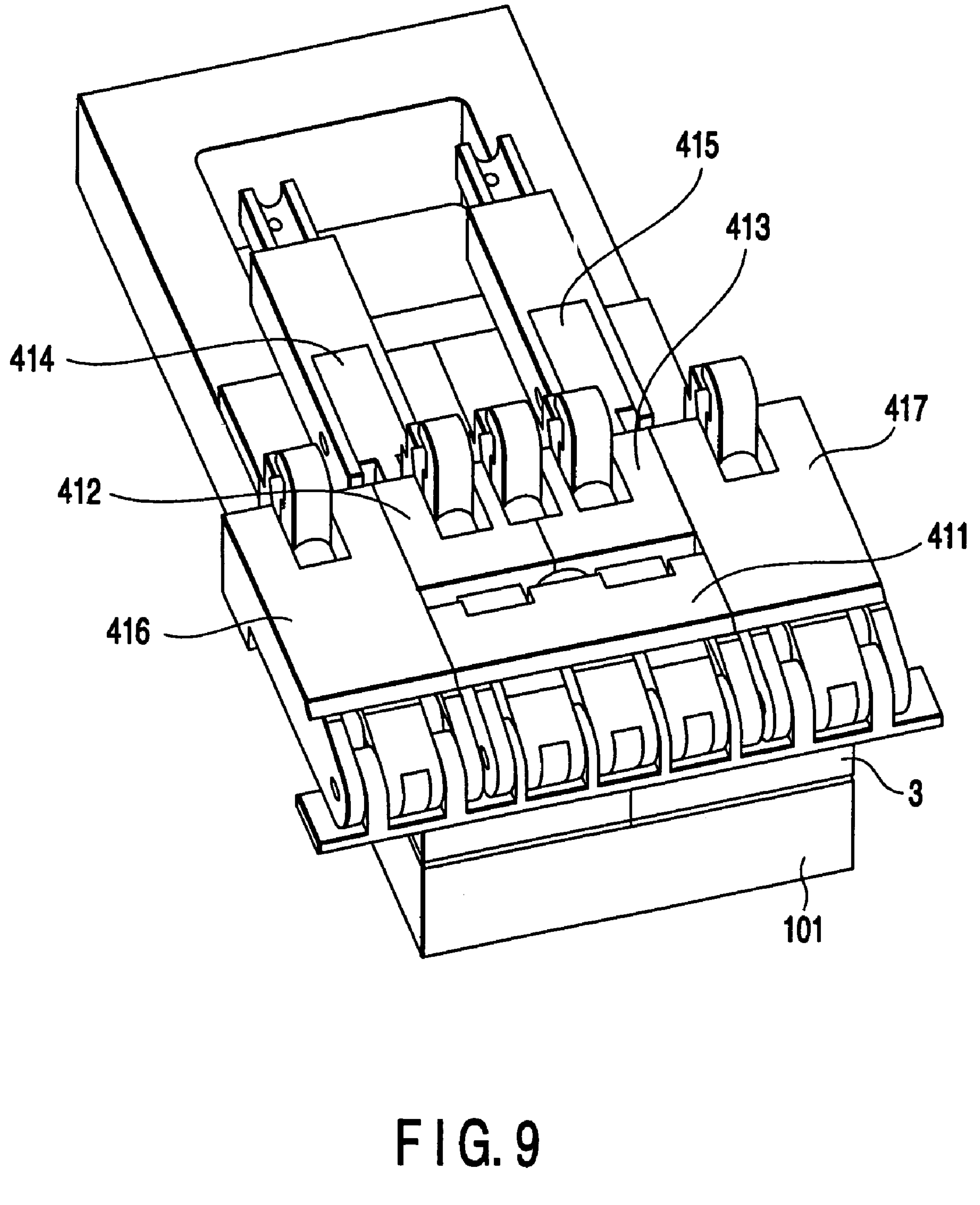
FIG. 9 is an oblique view showing the construction of the intermediate section block under the state that all the rods shown in FIGS. 1 and 2 are closed.
Figure 10:
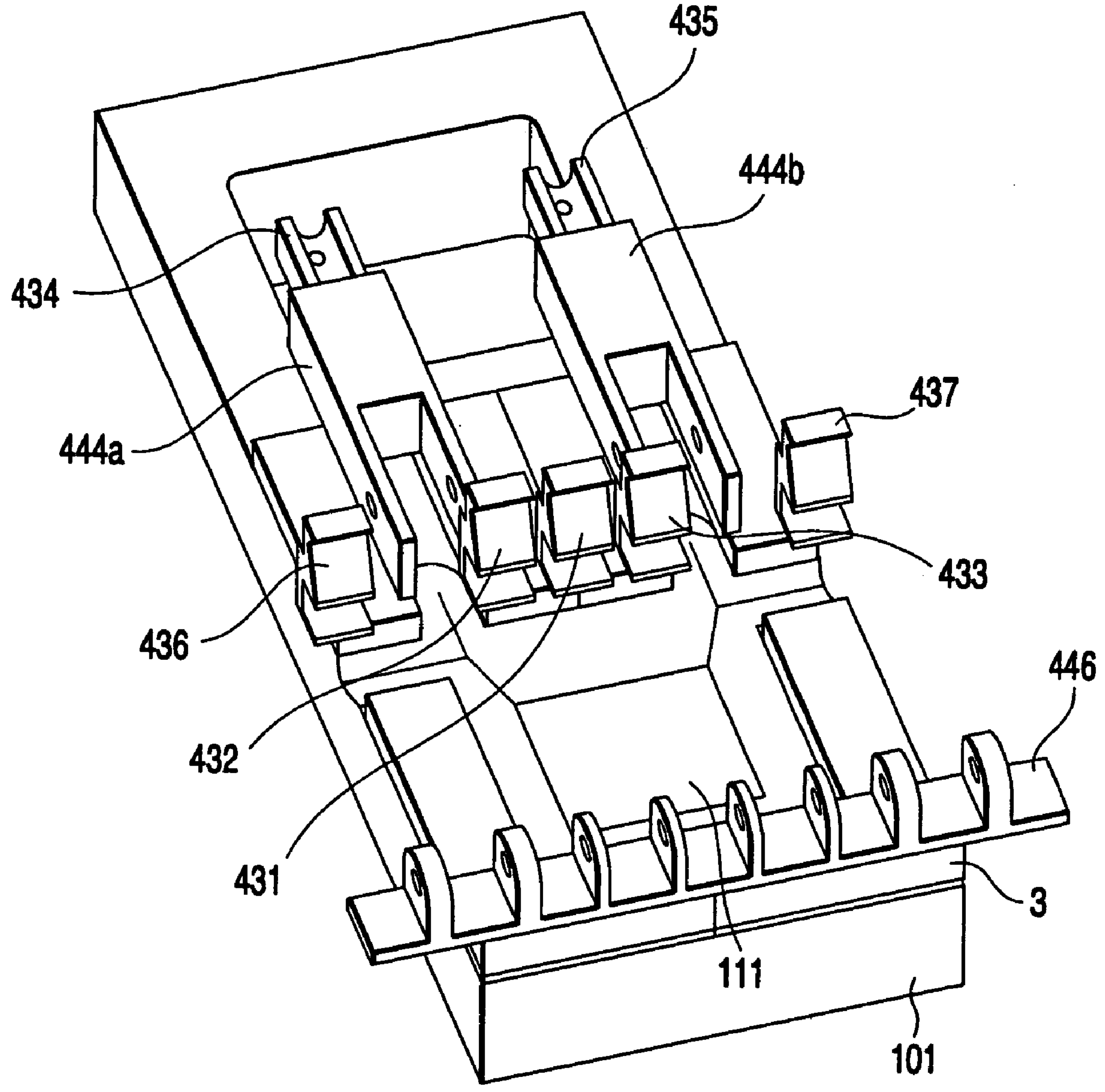
FIG. 10 is an oblique view showing the construction of the intermediate section block under the state that all the rods shown in FIG. 9 are omitted.
Figure 11:
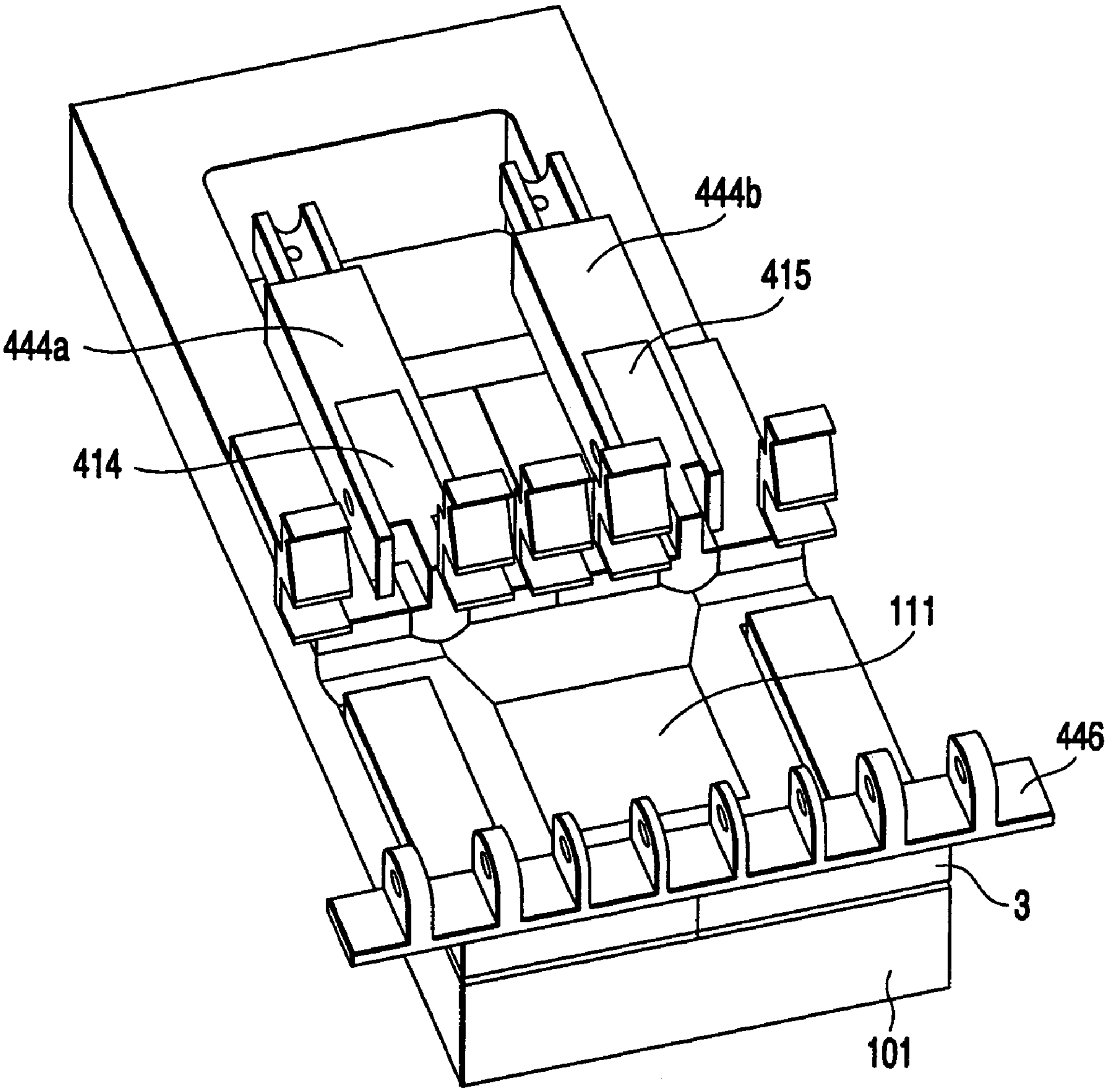
FIG. 11 is an oblique view showing the construction of the intermediate section block under the state that the rods for the inlet-outlet channel shown in FIG. 9 are selectively closed and the other rods are omitted.
Figure 12:
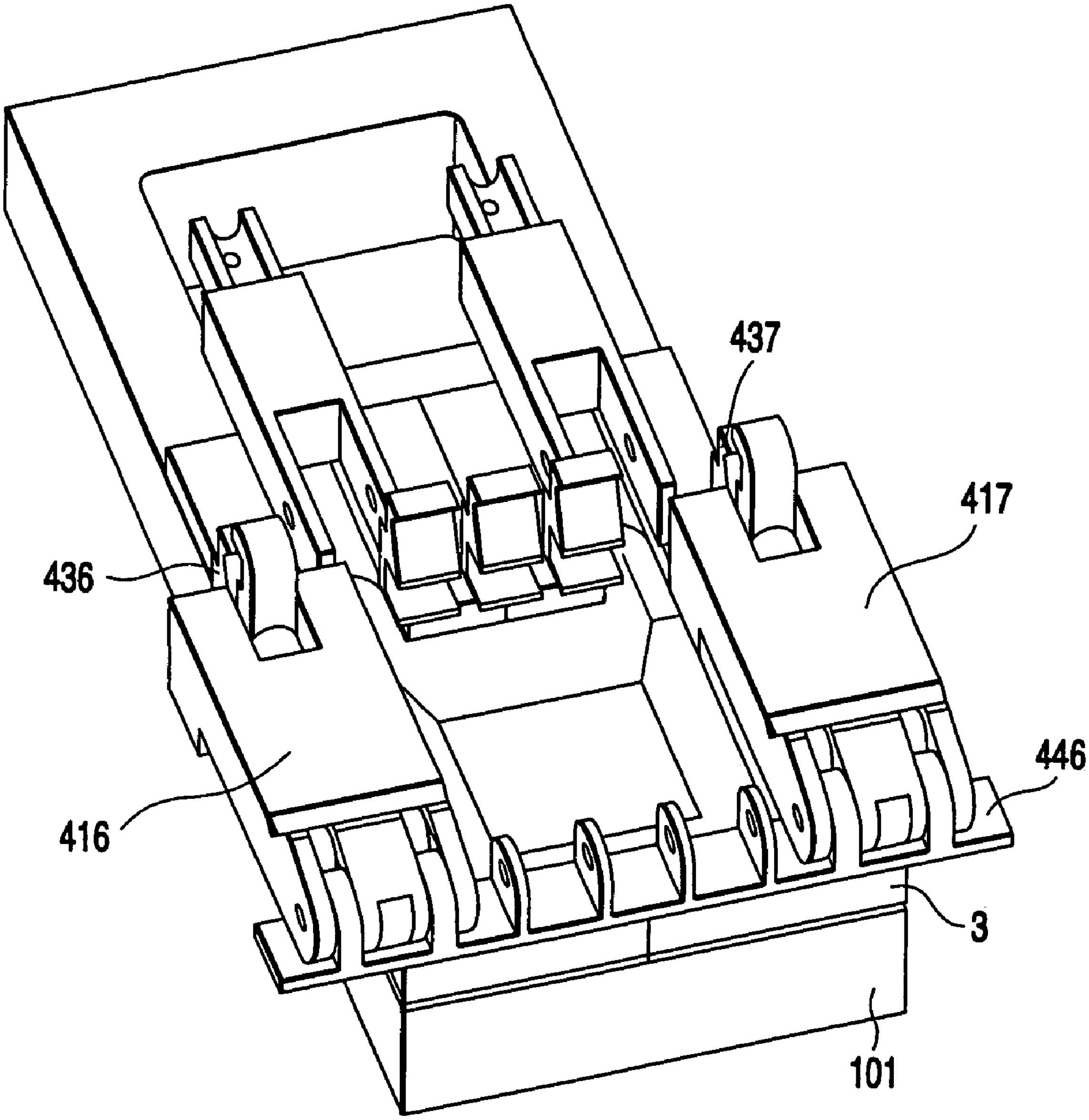
FIG. 12 is an oblique view showing the construction of the intermediate section block under the state that the rods for the joining channel shown in FIG. 9 are selectively closed and the other rods are omitted.
Figure 13:
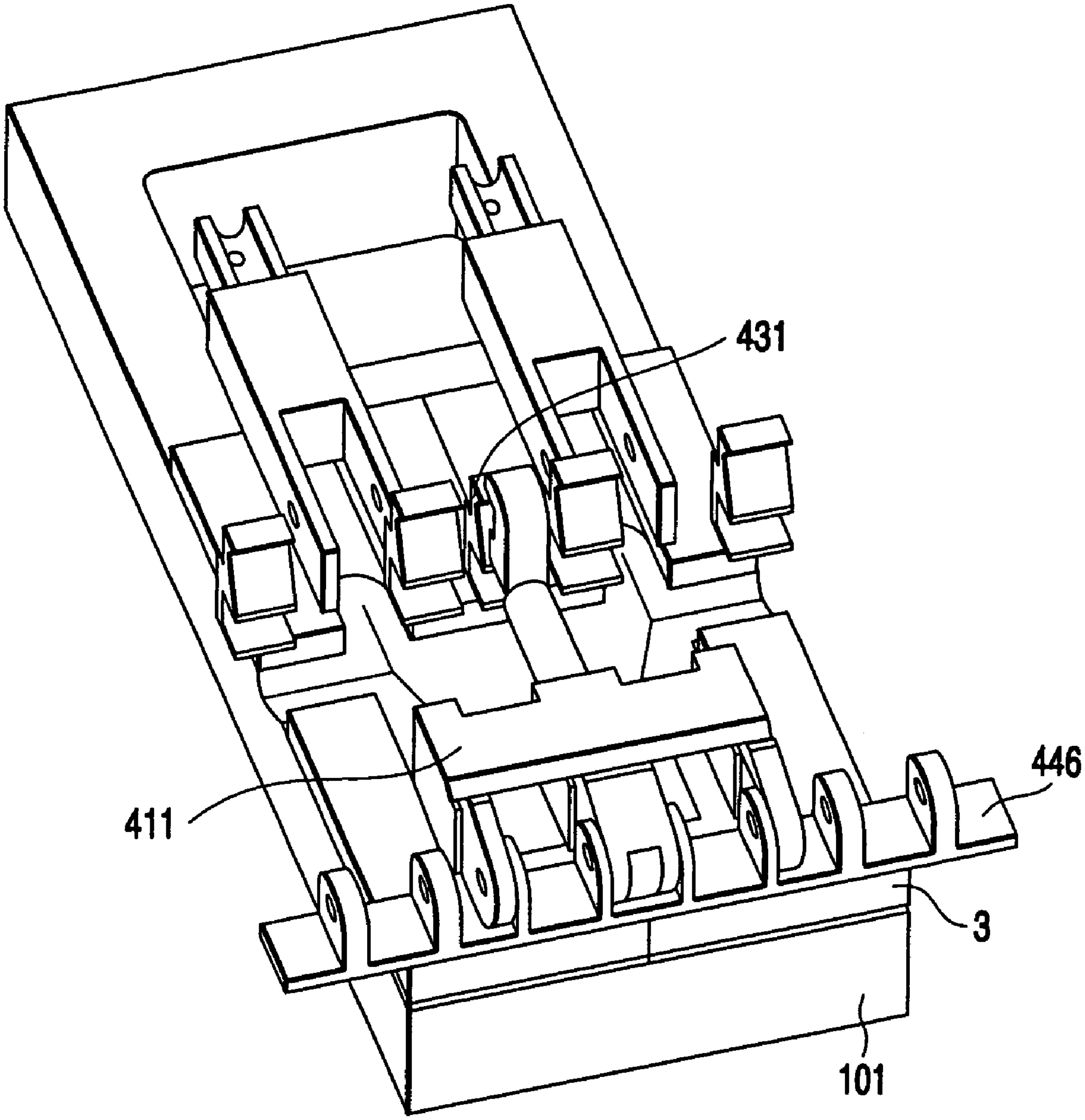
FIG. 13 is an oblique view showing the construction of the intermediate section block under the state that the central rod shown in FIG. 9 is selectively closed and the other rods are omitted.
Figure 14:
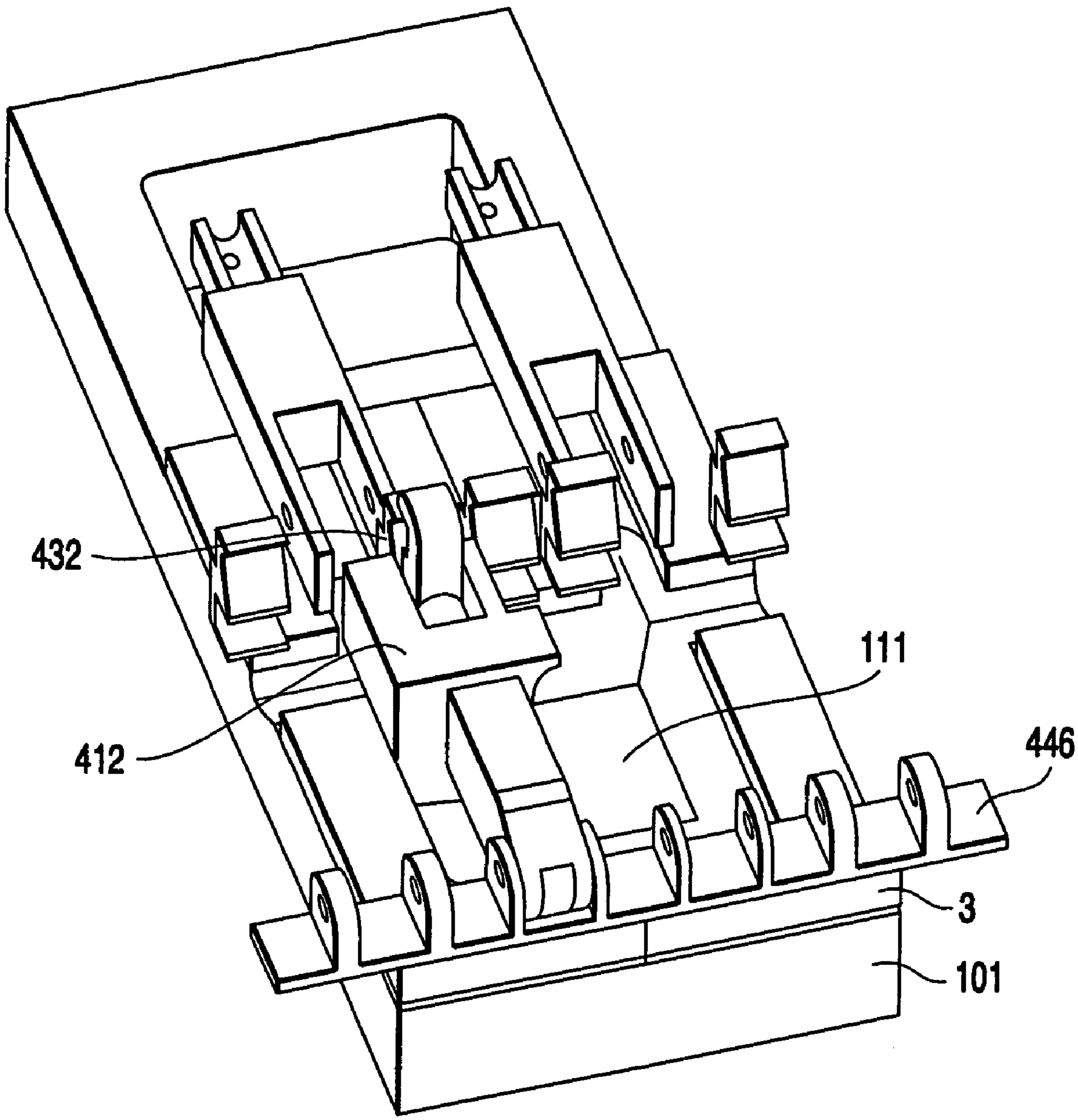
FIG. 14 is an oblique view showing the construction of the intermediate section block under the state that the left side rod shown in FIG. 9 is selectively closed and the other rods are omitted.
Figure 15:
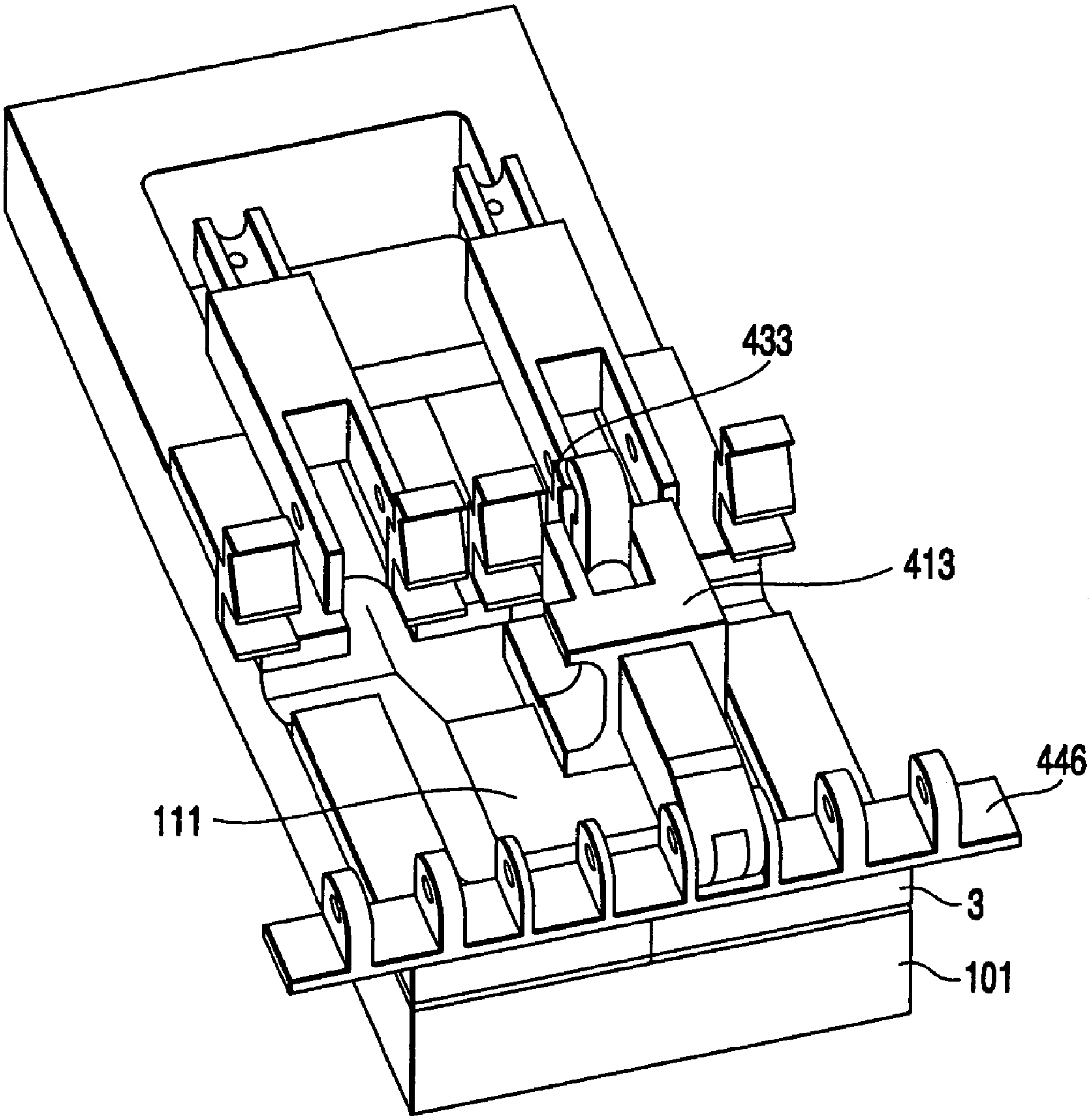
FIG. 15 is an oblique view showing the construction of the intermediate section block under the state that the right side rod shown in FIG. 9 is selectively closed and the other rods are omitted.
Figure 16:
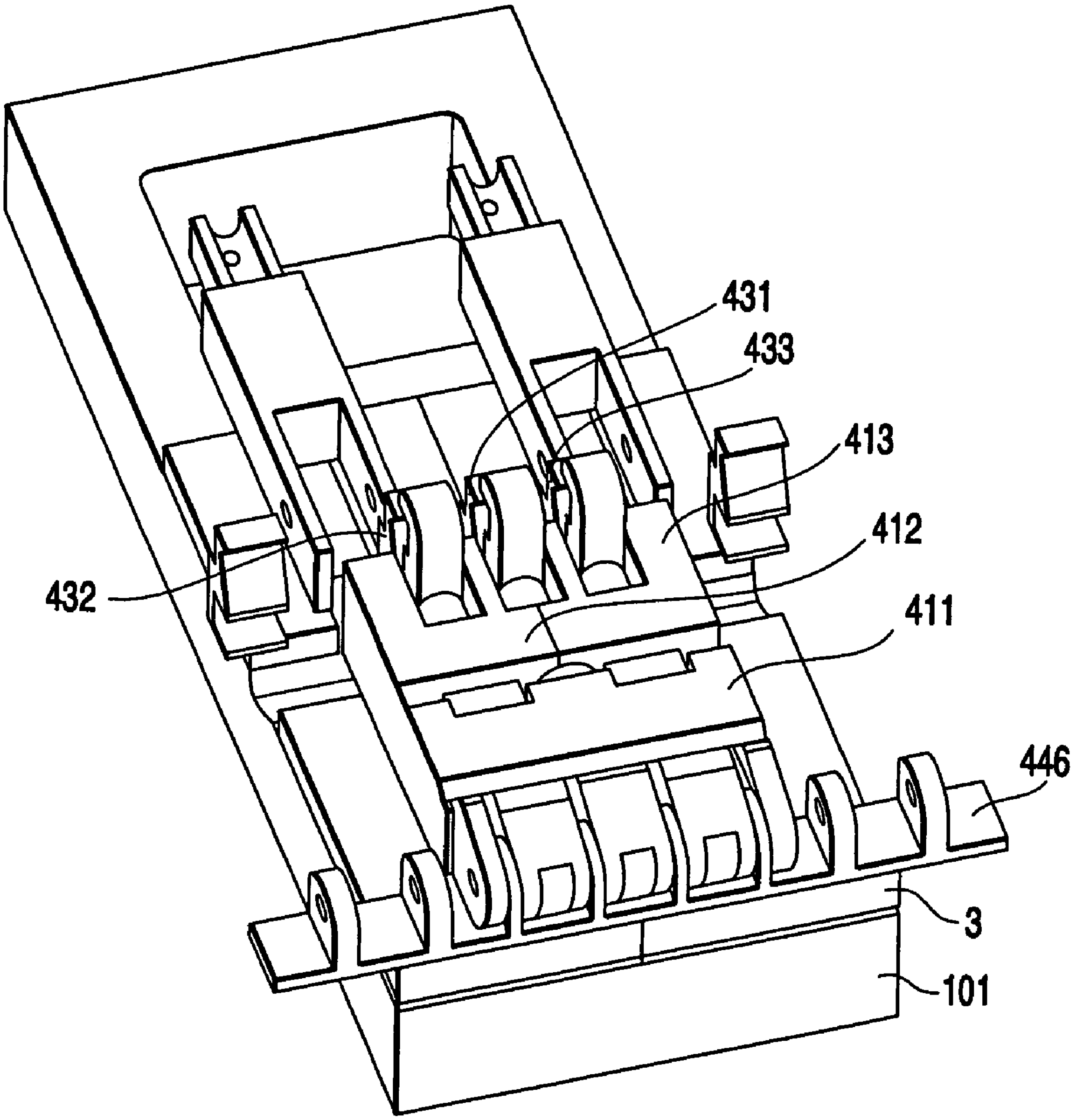
FIG. 16 is an oblique view showing the construction of the intermediate section block under the state that the central rod, the left side rod and the right side rod shown in FIG. 9 are selectively closed and the other rods are omitted.
Figure 17:
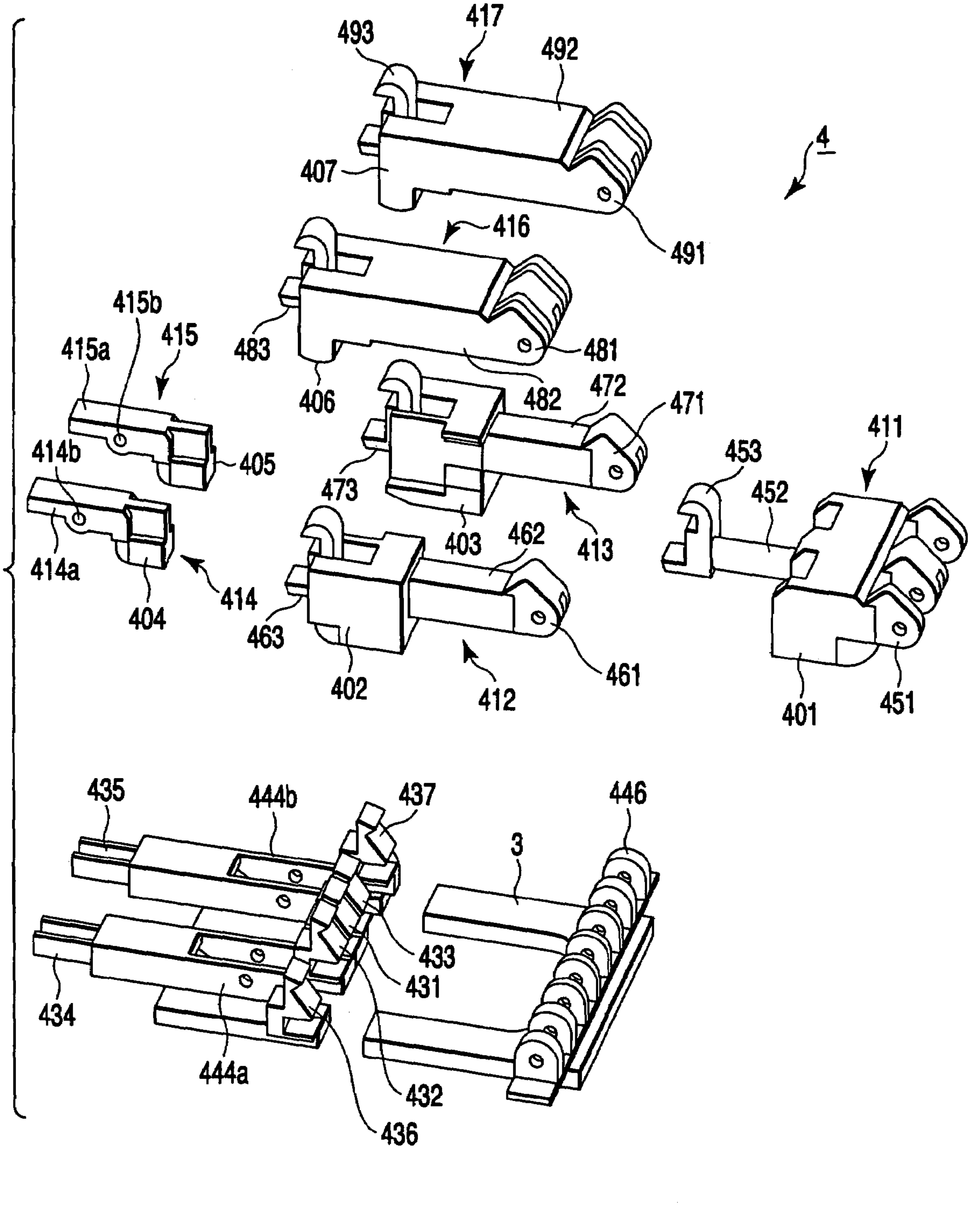
FIG. 17 is an oblique view showing in a dismantled fashion the construction of each of the constituents of the pushing block shown in FIG. 9.

FIGS. 9 to 16 are oblique views of the intermediate section block 101 showing various opened-closed states of the pushing block 4. It should be noted that the pushing block 4 is partly omitted in each of FIGS. 9 to 16. FIG. 9 shows the state that all the rods 411 to 417 are closed. FIG. 10 shows the state that all the rods 411 to 417 are omitted form the intermediate section block 101 shown in FIG. 9. FIG. 11 shows the state that the rods 414 and 415 alone are closed in the intermediate section block 101 shown in FIG. 9 with the other rods 411 to 413, 416 and 417 being omitted from the drawing. FIG. 12 shows the state that the rods 416 and 417 alone are closed in the intermediate section block 101 shown in FIG. 9 with the other rods 411 to 415 being omitted from the drawing. FIG. 13 shows the state that the central rod 411 alone is closed in the intermediate section block 101 shown in FIG. 9 with the other rods 412 to 417 being omitted from the drawing. FIG. 14 shows the state that the left side rod 412 alone is closed in the intermediate section block 101 shown in FIG. 9 with the other rods 411, 413, and 414 to 417 being omitted from the drawing. FIG. 15 shows the state that the right side rod 413 alone is closed in the intermediate section block 101 shown in FIG. 9 with the other rods 411, 412, and 414 to 417 being omitted from the drawing. Further, FIG. 16 shows the state that, the central rod 411, the left side rod 412 and the right side rod 413 alone are closed in the intermediate section block 101 shown in FIG. 9 with the other rods 414 to 417 being omitted from the drawing.

The movable rods 411 to 417 can be fixed by mainly two methods. In one of the two methods, a claw-shaped member for maintaining the pushed and fixed state is fitted in a concave portion formed in the locking section so as to push down and fix the rod. The movable rods 411 to 413, 416 and 417 are fixed by this fixing method. In the other fixing method, the pushed and fixed state is maintained by inserting the locking key into the region between the rod and the cover plate 3 so as to upheave and fix the rod. The movable rods 414 and 415 are upheaved and fixed by this fixing method.

In the movable rod that is fixed by the pushing and fixing method, a fulcrum section, a rod-like member, a claw-shaped member and a pad are formed integral. Also, the locking section comprises a claw-shaped member and a concave section. As shown in FIG. 17, fulcrum holes 451, 461, 471, 481, and 491 are formed in one-side edge portions of the movable rods 411 to 413, 416 and 417, respectively. Rod-like members 452, 462, 472, 482 and 492, which are inclined about the fulcrum holes 451, 461, 471, 481, and 491, respectively, are mounted to these fulcrum holes 451, 461, 471, 481, and 491, respectively. Also, claw-shaped members 453, 463, 473, 483, and 493 are mounted to the tips of the rod-like members 452, 462, 472, 482 and 492, respectively, and the pads 401, 402, 403, 406, and 407 are fixed to the intermediate sections.

The fulcrum holes 451, 461, 471, 481, and 491 are movably mounted, respectively, to a series of rear fulcrum holes 446 fixed to the cover plate 3. To be more specific, the movable rods 411 to 413, 416 and 417 are rotatably supported within a movable range such that the movable rods 411 to 413, 416 and 417 are rendered rotatable about the fulcrum holes 451, 461, 471, 481 and 491, respectively, by allowing a fulcrum bar to extend through each of the holes of the rear fulcrum holes 446 and each of the holes of the fulcrum holes 451, 461, 471, 481 and 491.

It is possible for the locking sections 431, 432, 433, 436 and 437 formed in the cover plate 3 to permit the movable rods 411 to 413, 416 and 417 to maintain the closed state of the corresponding channel portion. To be more specific, if the claw-shaped members 453, 463, 473, 483 and 493 formed in the rods 411 to 413, 416 and 417, respectively, are pushed downward from the outside so as to be fitted in and fixed within the concave sections of the locking sections 431, 432, 433, 436 and 437, the rods 411 to 413, 416 and 417 are held under the pushed down state so as to close the channels corresponding to the pads 401, 402, 403, 406 and 407.

The portions of the claw-shaped members 453, 463, 473, 483 and 493 of the locking sections 431, 432, 433, 436 and 327 are elastically flexed upon receipt of a driving force applied from the outside so as to release the fitting of the claw-shaped members 453, 463, 473, 483 and 493 into the locking sections 431, 432, 433, 436 and 327, with the result that the movable rods 411, 412, 413, 416 and 417 are individually opened. If the movable rods 411, 412, 413, 416 and 417 are opened, the flexible sheet 2 is brought back to the original stage before the flexing by the resilience of the flexible sheet 2 itself so as to open the corresponding channel portion. It should be noted, however, that the opening force of the movable rods 411, 412, 413, 416 and 417 is braked by the driving force applied from the outside so as to make it possible to control the opening speed of the movable rods noted above.

Incidentally, each of the channels of the retreating channel 131 can be closed and opened by the similar mechanism.

The movable rod that can be fixed by the upheaving and fixing method is constructed to include a rod-like member, a fulcrum and a pad which are formed integral. Also, the locking key includes a wedge section. The inlet-outlet pads 404 and 405 are fixed, respectively, to the one-side edges of the rod-like members 414*a* and 415*a* of the movable rods 414 and 415. Also, fulcrum holes 414*b* and 415*b* are mounted, respectively, to the intermediate portions of the rod-like members 414*a* and 415*a*.

The fulcrum holes 414*b* and 415*b* are rotatably mounted to a series of forward fulcrum holes 444*a* and 444*b*, respectively, which are fixed to the cover plate 3. To be more specific, a fulcrum bar (not shown) is allowed to extend through each of the holes of the forward fulcrum holes 444*a*, 44*b* and each of the holes of the fulcrum holes 414*b* and 415*b* so as to permit the movable rods 414 and 415 to be made rotatable within a rotatable range about the fulcrum holes 414*b* and 415*b*, respectively.

The locking keys 434 and 435 arranged on the cover plate 3 permit the movable rods 414 and 415, respectively, to maintain the closed state of the inlet-outlet channels 114 and 115. To be more specific, if the locking key 434 is inserted into the regions between the movable rod 414 and the cover plate 3 so as to upheave and fix the movable rod 414, the inlet-outlet channel 114 is closed by the movable rod 414. The locking keys 434 is withdrawn from the regions between the movable rod 414 and the cover plate 3 by the driving force applied from outside the nucleic acid detecting cassette 100, with the result that the movable rod 414 is opened and, thus, the inlet-outlet channel 114 is opened. In this case, the flexible sheet 2 is brought back to the original state by the resilience of the flexible sheet 2 itself. The closed state of the inlet-outlet channel 115 can also be maintained and opened with the movable rods 415 and the locking keys 435 by the similar mechanism.

(2)-6-2 Fluid Holding Channel 111 and Retreating Channel 131:

The opening-closing operations of the fluid holding channel 111 and the retreating channel 131 will now be described in detail with reference to FIGS. 18A to 24.

Each of the fluid holding channel 111 and the retreating channel 131 is capable of realizing various inner volume patterns of the channel by individually driving the central rod 411, the left side rod 412 and the right side rod 413.

Examples of various patterns ranging between the completely closed state and the completely opened state of the fluid holding channel 111 will now be described with reference to FIGS. 18A to 18D each showing a cross section of the intermediate section block 101 and with reference to FIGS. 19 to 24 each directed to an oblique view showing in a dismantled fashion the construction of the intermediate section block 101.

Figure 18A:
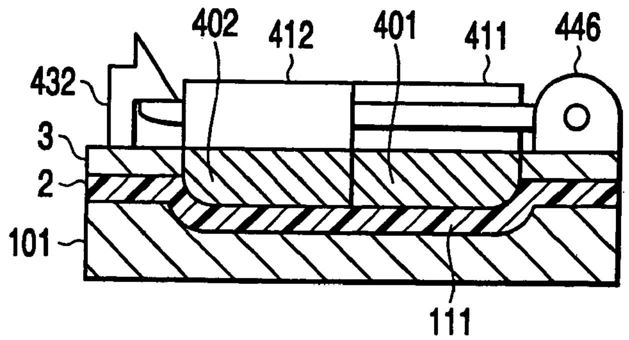
FIGS. 18A to 18D are cross sectional views schematically showing various patterns of the fluid holding channel that can be opened or closed by the pushing block shown in FIG. 9 so as to vary the inner volume of the fluid holding channel.
Figure 18B:
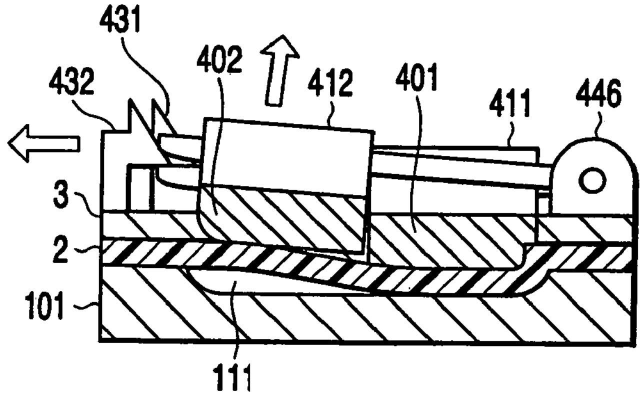
Figure 18C:
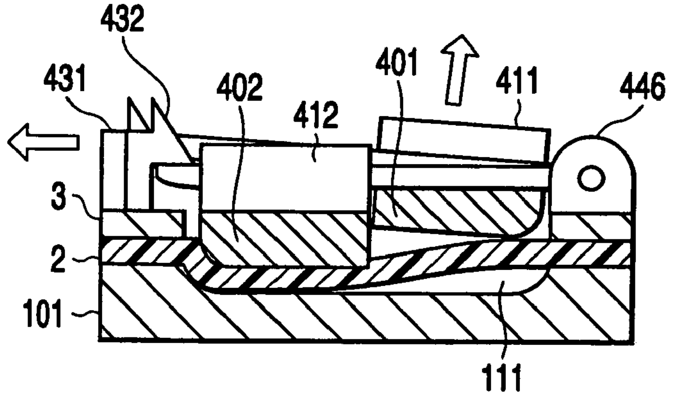
Figure 18D:
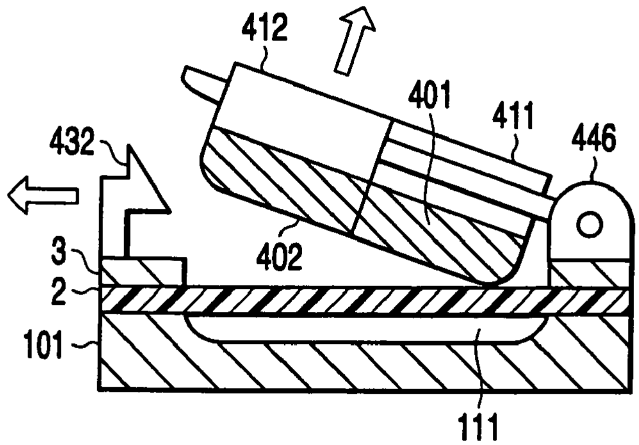
Figure 19:
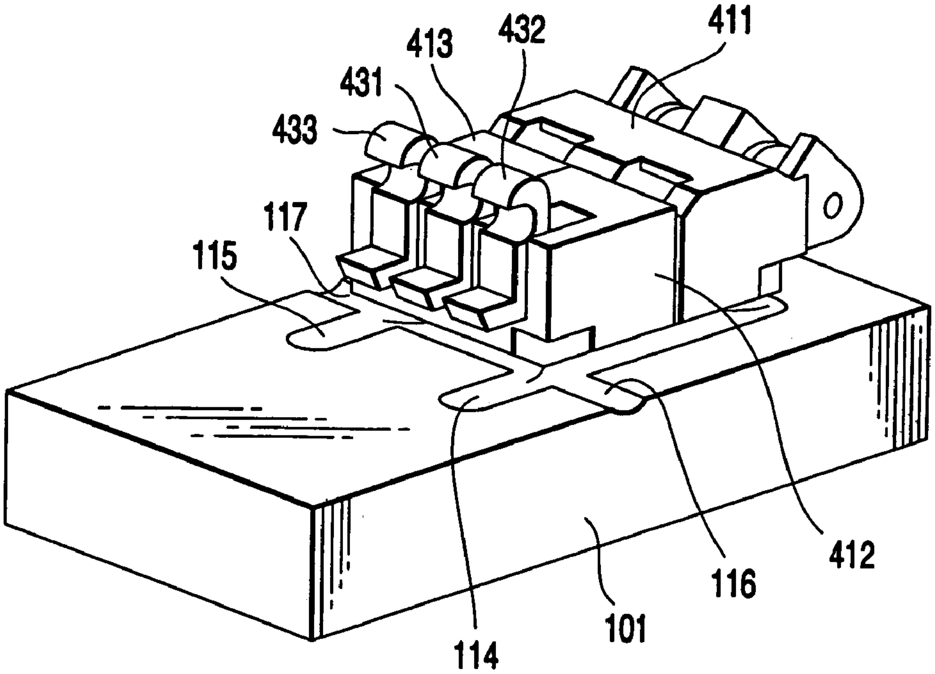
FIG. 19 is an oblique view partially showing the construction of each of the intermediate section block and the pushing block shown in FIG. 9.
Figure 20:
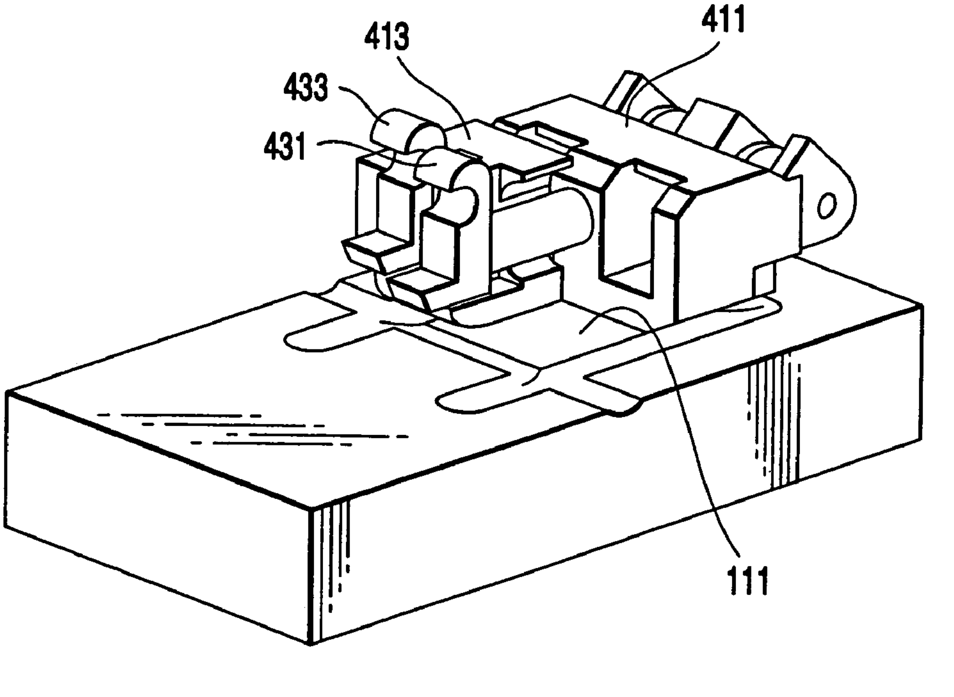
FIG. 20 is an oblique view partially showing the construction of each of the intermediate section block and the pushing block shown in FIG. 9.
Figure 21:
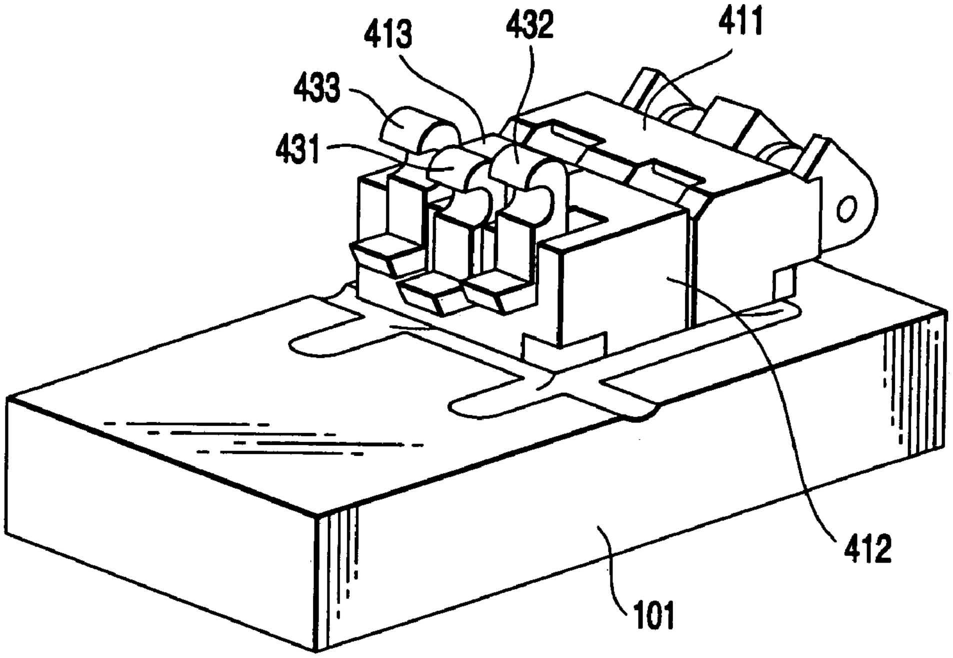
FIG. 21 is an oblique view partially showing the construction of each of the intermediate section block and the pushing block shown in FIG. 9.
Figure 22:
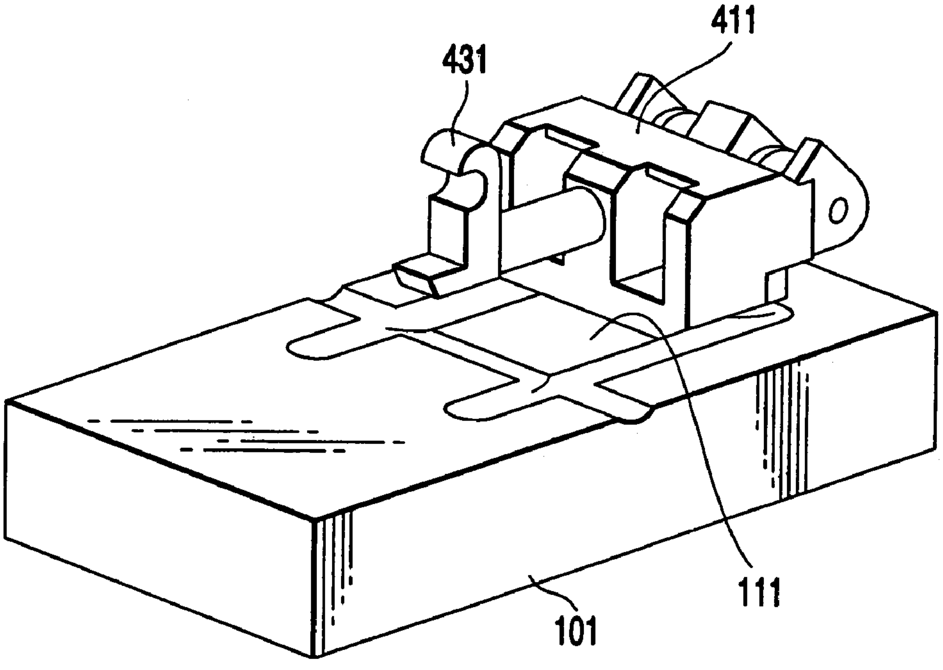
FIG. 22 is an oblique view partially showing the construction of each of the intermediate section block and the pushing block shown in FIG. 9.
Figure 23:
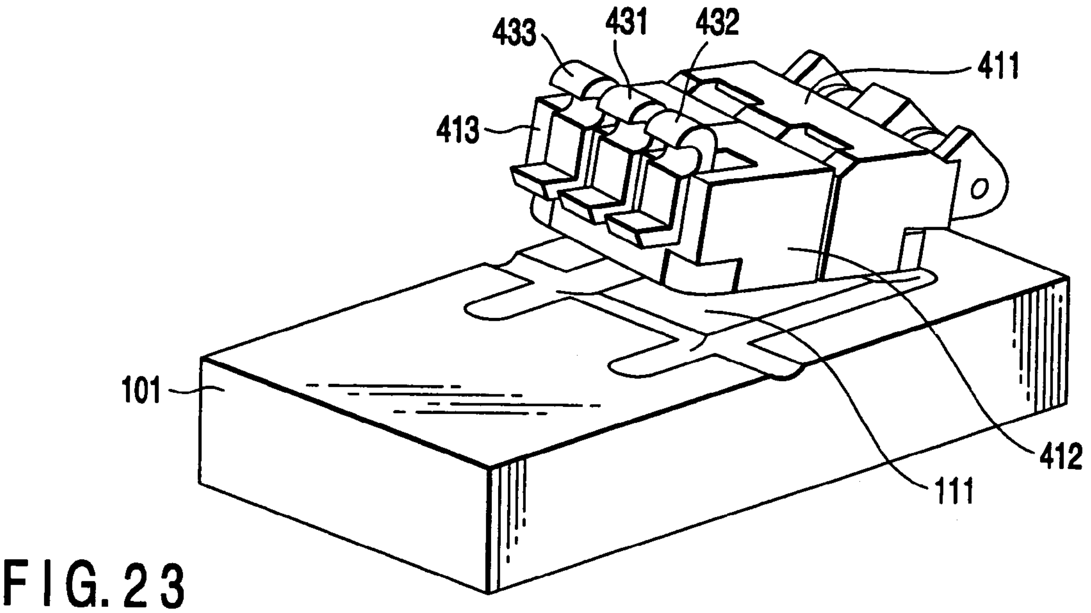
FIG. 23 is an oblique view partially showing the construction of each of the intermediate section block and the pushing block shown in FIG. 9.
Figure 24:
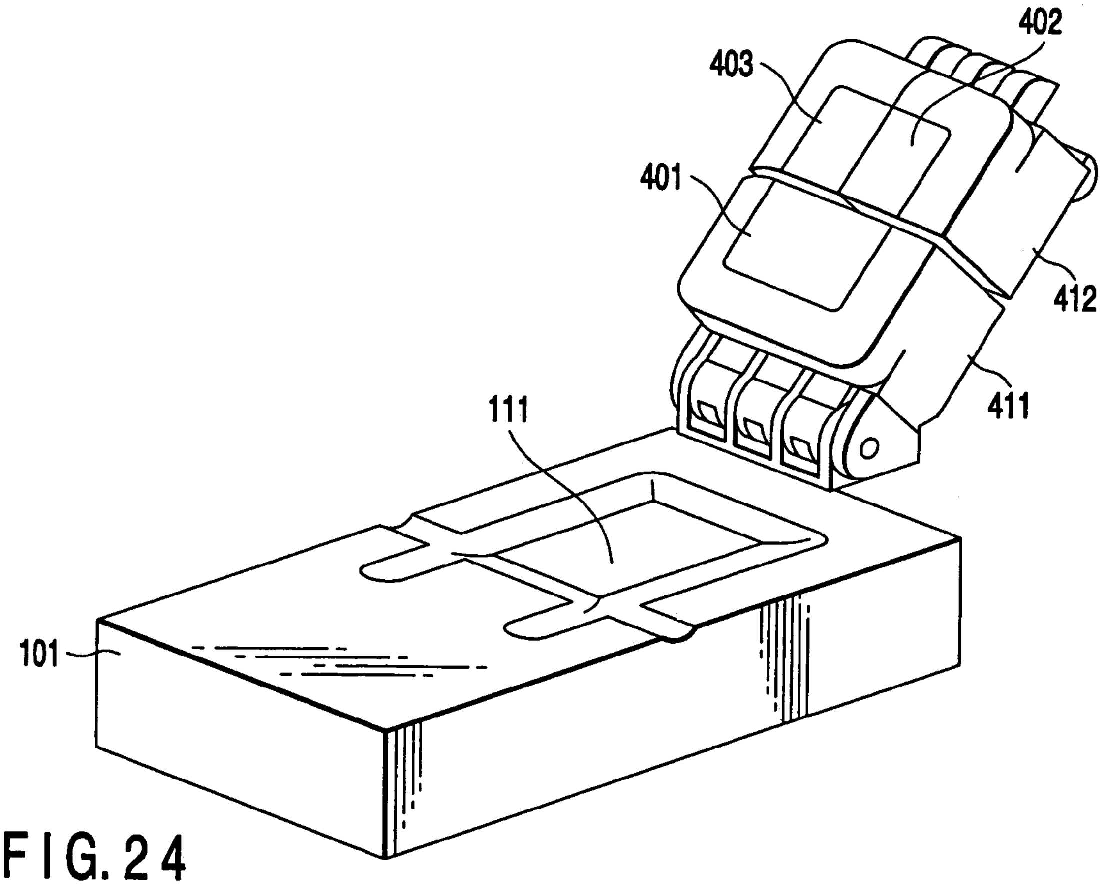
FIG. 24 is an oblique view partially showing the construction of each of the intermediate section block and the pushing block shown in FIG. 9.

As shown in FIGS. 18A and 19, if the central rod 411, the left side rod 412 and the right side rod 413 are locked by the locking sections 431, 432 and 433, respectively, the fluid holding channel 111 is held under the completely closed state. It is possible to convert the completely close state shown in FIG. 19 into the state that the right side rod 413 alone is opened as shown in FIG. 20. In this case, the fluid holding channel 111 is put under a semi-opened state in the vicinity of the channel terminating edge section. Incidentally, the left side rod 412 is omitted in FIG. 20. Further, if both the left side rod 412 and the right side rod 413 are opened as shown in FIGS. 18B and 21, the fluid holding channel 111 is put under a semi-opened state in the front portion, i.e., in a region close to the channel starting edge section and the channel terminating edge section. On the other hand, if the central rod 411 alone is opened as shown in FIGS. 18C and 22, the fluid holding channel 111 is put under a semi-opened state in the rear portion, i.e., in the portion remote from the channel starting edge section and the channel terminating edge section. Incidentally, the left side rod 412 and the right side rod 413 are omitted in FIG. 22. Further, if all of the central rod 411, the left side rod 412 and the right side rod 413 are opened as shown in FIGS. 18D and 23, the completely opened state of the fluid holding channel 111 is maintained. Incidentally, FIG. 24 shows the state that the central rod 411, the left side rod 412 and the right side rod 413 are further opened so as to permit the surfaces of the pads 401,402 and 403 to be exposed to the outside.

The description given above is directed to the opened state and the closed state of the fluid holding channel 111. Since the retreating channel 131 is also opened or closed like the fluid holding channel 111, the description is omitted in respect of the opening and the closing of the retreating channel 131.

Figure 25A:
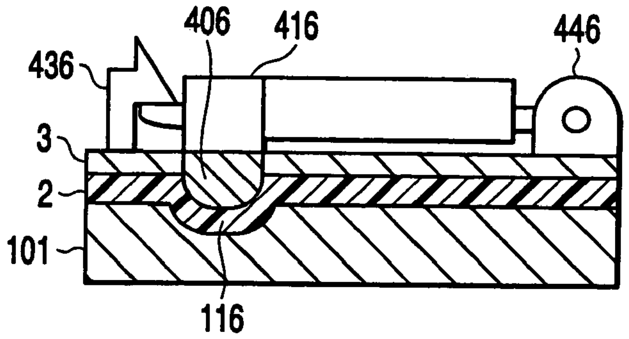
FIGS. 25A and 25B are cross sectional views schematically showing the construction of the joining channel that is opened or closed by the pushing block shown in FIG. 9.
Figure 25B:
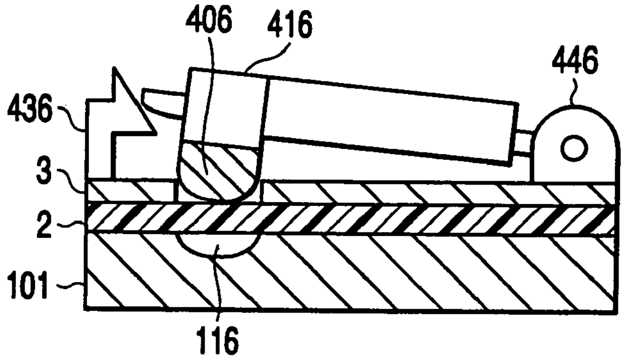

(2)-6-3 Joining Channels 116 and 117:

The opening-closing operations of the joining channels 116 and 117 will now be described with reference to FIGS. 25A and 25B. As shown in FIG. 25A, if the movable rod 416 is locked by the locking section 436, the completely closed state of the joining channel 116 is maintained. If the locking is released under this state, the joining channel 116 is put under the completely opened state as shown in FIG. 25B. To be more specific, if the locking section 436 is deformed by an external driving force so as to permit the movable rod 416 to be released from the locking section 436 as shown in FIG. 25B, the completely opened state of the joining channel 112 is maintained.

Incidentally, the opening-closing of the joining channel 117 is also controlled like the joining channel 116 and, thus, the description is omitted in respect of the joining channel 117.

Figure 26A:
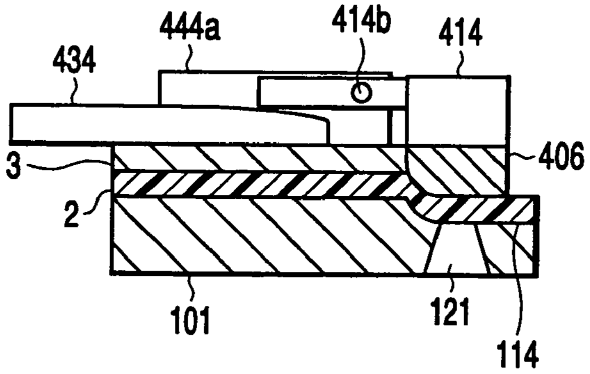
FIGS. 26A and 26B are cross sectional views schematically showing the construction of the intermediate section block in which is formed an inlet-outlet channel that can be opened or closed by the pushing block shown in FIG. 9.

(2)-6-4 Inlet-Outlet Channels 114 and 115:

The opening-closing operation of the inlet-outlet channels 114 and 115 will now be described with reference to FIGS. 26A and 26B. If the movable rod 414 is locked by the locking key 434 as shown in FIG. 26A, the completely closed state of the inlet-outlet channel 114 is maintained. To be more specific, the locking key 434 is inserted into the region between the movable rod 414 and the cover plate 3 so as to bring the wedge section of the locking key 434 into contact with the edge section of the movable rod 414. As a result, the movable rod 414 is rotated about the fulcrum hole 414*b* so as to push up the portion on the side opposite to the side on which the pad is formed. It follows that the left side inlet-outlet pad 404 is pushed down with the fulcrum hole 414*b* acting as the rotary axis, with the result that the completely closed state is maintained.

Figure 26B:
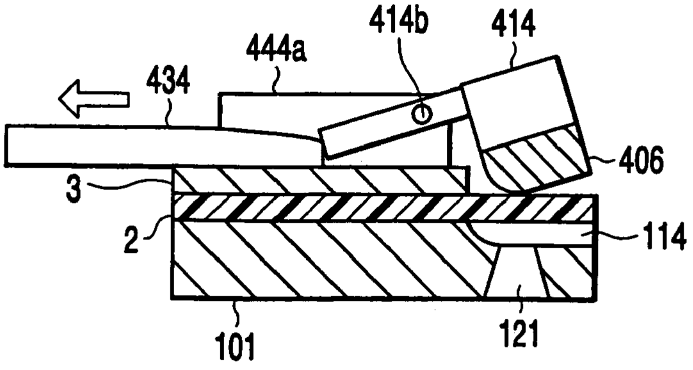

Also, if the locking key 434 is withdrawn by an external driving force so as to release the movable rod 414 from the locking key 434 as shown in FIG. 26B, the completely opened state of the inlet-outlet channel 115 is maintained. Concerning the withdrawing of the locking key 434, the force for pushing up the movable rod 414 is eliminated if the locking key 434 is withdrawn in, for example, the direction denoted by an arrow in FIG. 26. It follows that the left side inlet-outlet pad 404 is pushed up with the fulcrum hole 414*b* acting as the rotary axis, with the result that the completely opened state is maintained by the resilience of the flexible sheet 2.

Incidentally, the opening-closing of the inlet-outlet channel 115 can also be controlled like the inlet-outlet channel 114 and, thus, the description in conjunction with the inlet-outlet channel 115 is omitted.

(3) Method of Controlling Fluid Movement:

The control method of the fluid moving within the channel will now be described. Used in this control method is the pushing mechanism described above, which permits varying the channel and the inner volume thereof.

(3)-1 Injection of Reagent and Sample:

(3)-1-1 Injection of Reagent Solution:

The reagent is injected into the fluid holding channel 111 by utilizing the opening portions 121 and 122 formed in the back surface of the nucleic acid detecting cassette 100, i.e., inlet-outlet port. The process of injecting the reagent solution into the fluid holding channel 111 will now be described with reference to FIGS. 27A to 27E, FIGS. 28A to 28D and FIGS. 29A to 29B.

Specifically, FIGS. 27A to 27E schematically show collectively the process of injecting a reagent solution with reference to the schematic drawing of the fluid holding channel 111 of the type that the inner volume thereof can be varied. On the other hand, FIGS. 28A to 28D are cross sectional views schematically showing the state of the fluid holding channel 111 in line with the process of injecting the reagent solution.

FIGS. 27A to 27E show inlet-outlet valves 314 and 315. The inlet-outlet valve 314 is formed by combining the inlet-outlet channel 114, the inlet-outlet pad 404 and the flexible sheet 2. Likewise, the inlet-outlet valve 315 is formed by combining the inlet-outlet channel 115, the inlet-outlet pad 405 and the flexible sheet 2. In other words, the valve mechanisms achieved by the combination of the inlet-outlet channels 114, 115, the inlet-outlet pads 404, 405 and the flexible sheet 2 are equivalently represented by the inlet-outlet valves 314 and 315 in FIGS. 27A to 27E.

On the other hand, the valve mechanisms achieved by the combination of the joining channels 116, 117, the joining pads 406, 407 and the flexible sheet 2 are equivalently represented by joining valves 316 and 317 in FIGS. 27A to 27E.

Figures 27A, 27B, 27C, 27D, 27E:
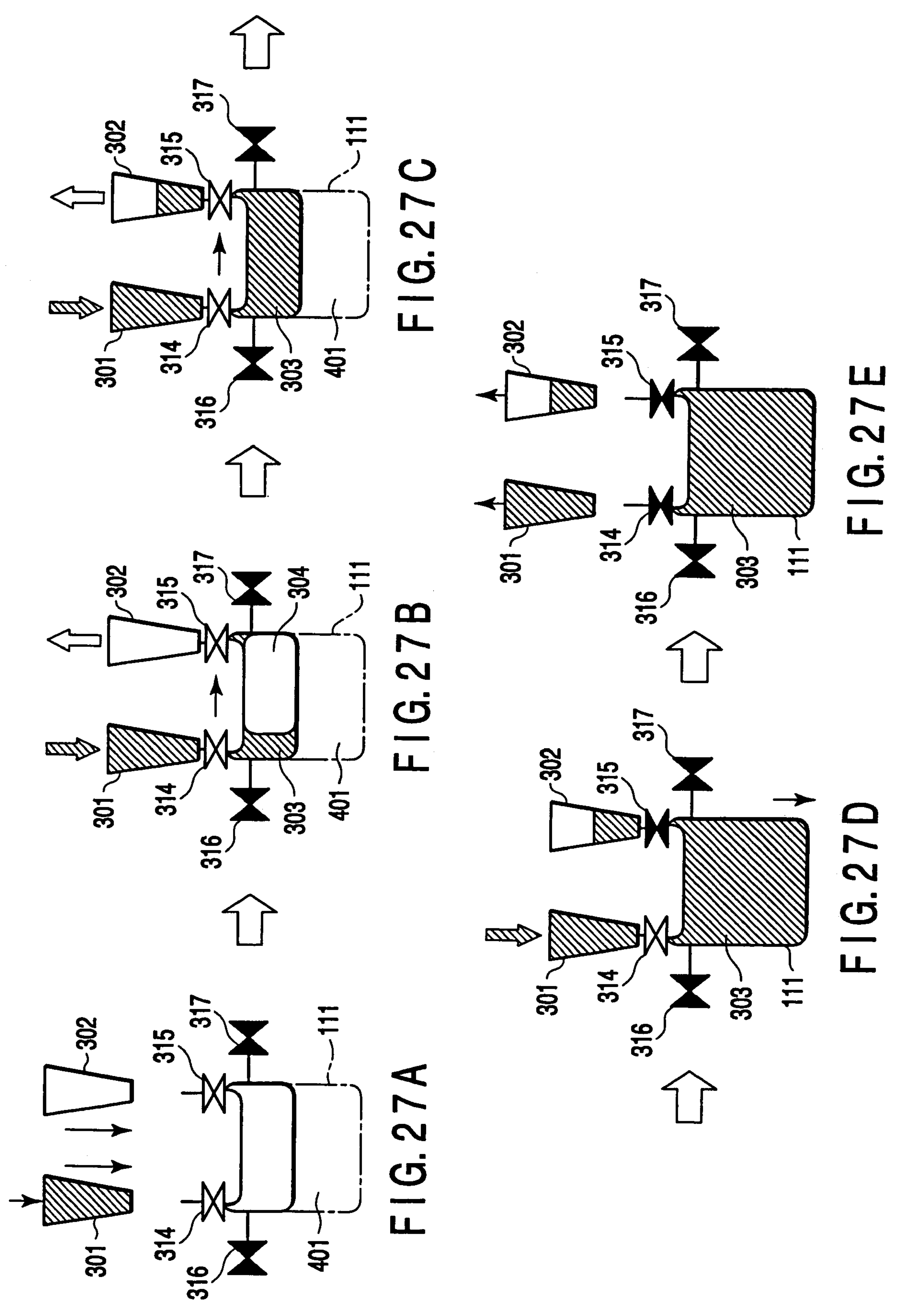
FIGS. 27A to 27E schematically show collectively the process of transferring a reagent in the fluid holding channel shown in FIG. 2.
Figure 28A:
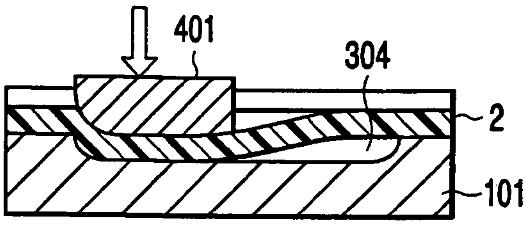
FIGS. 28A to 28D are partial cross sectional views schematically showing the construction of the intermediate section block in which is formed the fluid holding channel included in the reagent transfer mechanism shown in FIG. 2.
Figure 29A:
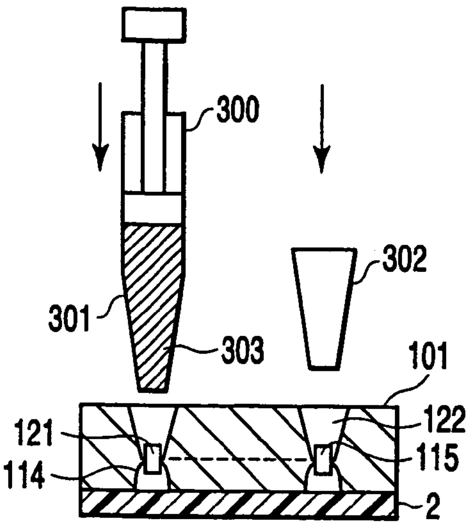
FIGS. 29A and 29B are partial cross sectional views schematically showing the construction of the intermediate section block in which is formed the opening section shown in FIG. 2.
Figure 29B:
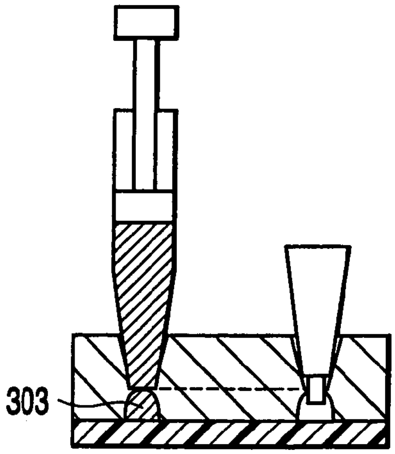

Concerning the fluid holding channel 111 capable of varying the inner volume, the planar shape of the inner volume is schematically shown in FIGS. 27A to 27E. Incidentally, the retreating channel 131, which is not shown in FIGS. 27A to 27E, is also capable of varying the inner volume like the fluid holding channel 111 and, thus, the description of the retreating channel 131 with reference to the drawings is omitted.

a. Setting of Initial Inner Volume of Channel:

In the first step, the inlet-outlet valves 314 and 315 are opened with the joining valves 316 and 317 kept closed as shown in FIG. 27A. Then, the central pad 401 is pushed in so as to decrease the width of the fluid holding channel 111, thereby setting the inner volume of the channel at the value required for the initial state. In this stage, a gas 304 inside the fluid holding channel 111 flows through the inlet-outlet valves 314 and 315 so as to be discharged from the opening portions 121 and 122 to the outside of the fluid holding channel 111. In other words, the fluid (gas) is discharged to the outside of the fluid holding channel 111 in an amount corresponding to the inner volume varied by the fluid holding channel 111, as shown in FIG. 28A.

b. Start-Up of Reagent Injection:

If the initial inner volume of the fluid holding channel 111 is determined in the process (a) given above, i.e., the process of setting the initial inner volume of the channel, the injection of the reagent solution is started. FIGS. 29A and 29B are cross sectional views of the intermediate section block 101 having the opening portions 121 and 122 formed therein for the injection of the reagent solution. To be more specific, FIG. 29A is a cross sectional view showing the state before the reagent is injected into the intermediate section block 101. On the other hand, FIG. 29B is a cross sectional view showing the intermediate section block 101 under the state that a tip 301 of a pipette 300 and another tip 302 are inserted into the opening portions 121 and 122, respectively. As shown in FIG. 29A, the nucleic acid detecting cassette 100 is held such that the opening portions 121 and 122 are positioned on the upper side relative to the fluid holding channel 111. Then, the pipette 300 loaded with the reagent in an amount slightly larger than the volume of the reagent 303 to be injected is prepared, and the tip 301 of the pipette 300 is inserted into the opening portion 121. At the same time, the tip 302 that is not loaded with the reagent and open to the outside is also prepared and inserted into the opening portion 122 on the side opposite to the opening portion 121 into which the pipette 300 loaded with the reagent has been inserted.

Figure 28B:
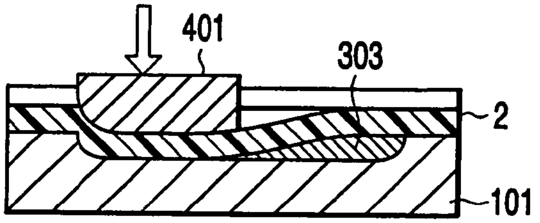
Figure 28C:
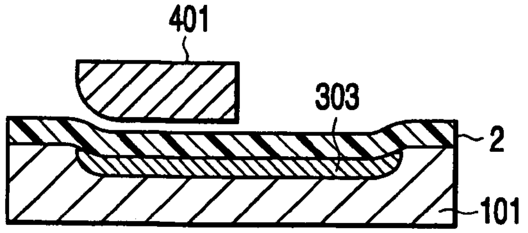
Figure 28D:
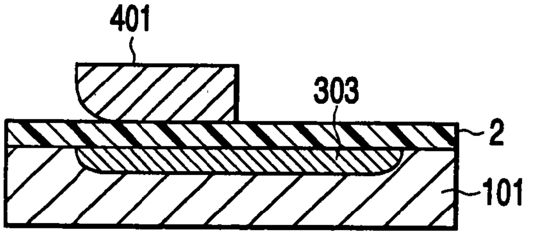

In the next step, the reagent 303 is injected from the tip 301 as shown in FIG. 27B. It should be noted that the fluid holding channel 111 has a sufficiently small width. Therefore, in this stage, the interface between the reagent 303, which is a liquid, and the gas 304 filling the inner space of the channel retains a curved plane because of the surface tension so as to make it possible to separate the reagent 303 from the gas 304 without mixing. In other words, the reagent 303 can be loaded in the fluid holding channel 111 without mixing while preventing the gas 304 from being involved in the reagent solution as air bubbles.

c. Termination in Injection of Reagent Solution:

The reagent solution 303 is injected until the reagent solution 303 flows into the tip 302 on the outlet side of the gas, as shown in FIGS. 27C and 28B. If a desired amount of the reagent solution 303 has been injected into the fluid holding channel 111, the injection of the reagent solution 303 is finished, and the operation proceeds to the process of "closure of the inlet-outlet valve", which is to be described herein later. Also, where the reagent solution is further injected in an amount equal to the maximum inner volume of the fluid holding channel 111 as shown in FIG. 28D, the operation proceeds to the process of "injection of replenishing reagent solution" described herein later after completion in the injection of the reagent solution.

d. Injection of Replenishing Reagent Solution:

As shown in FIG. 27D, the valve 315 on the outlet side of the gas is closed, and the central pad 401 is opened so as to inject further the reagent solution 303. When the central pad 401 is opened, the inner pressure of the fluid holding channel 111 is rendered slightly negative, as shown in FIG. 28C. However, since the reagent solution is contained in the pipette 300 in a sufficiently large amount, it is impossible for the gas to be involved in the reagent solution as air bubbles.

The reagent solution is further injected until the reagent 303 remains slightly within the tip 301 on the inlet side of the reagent solution, and the reagent 303 is pushed in until the inner region of the fluid holding channel 111 is slightly pressurized. Then, the pressure within the opening portion of the tip 301 and the pressure inside the fluid holding channel 111 are rendered substantially equal to the atmospheric pressure so as to confirm that the amount of the reagent solution 303 within the tip 301 is slightly increased. In this case, if the reagent 303 remains inside the tip 301, the gas is not involved in the reagent solution, even if the pressure inside the fluid holding channel is negative so as to cause the reagent 303 within the tip 301 to be slightly sucked into the fluid holding channel 111.

e. Closure of Inlet-Outlet Valve:

Finally, the inlet-outlet valves 314 and 315 are closed, and the tips 301 and 302 are detached from the opening portions 121 and 122, respectively, as shown in FIG. 27E.

By the process steps described above, it is possible to inject the reagent solution into the fluid holding channel 111 under the two-stage of set amounts while preventing the gas from being involved in the reagent solution as air bubbles. In the stage of injecting the reagent solution, the pressure inside the flexible sheet 2 is equal to the pressure outside the flexible sheet 2, with the result that the flexible sheet 2 is allowed to retain a prescribed shape so as to maintain constant the loaded amount of the reagent solution. Further, since an extremely high negative pressure or positive pressure is not applied to the reagent solution, the gas is unlikely to enter the fluid holding channel 111 from the outside or the reagent solution is unlikely to leak from within the channel. In addition, since a gaseous portion is not included inside the channel, it is possible to prevent the gas from being dissolved in the reagent solution during the storage over a long period of time.

Figure 30A:
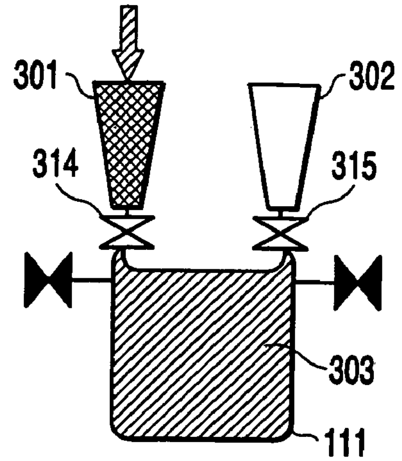
FIGS. 30A to 30C schematically show collectively the process of injecting a sample into the fluid holding channel shown in FIG. 2.
Figure 30B:
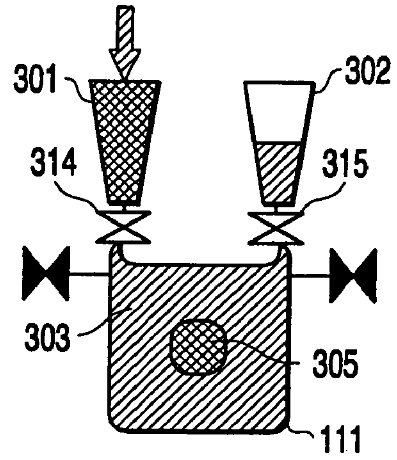
Figure 30C:
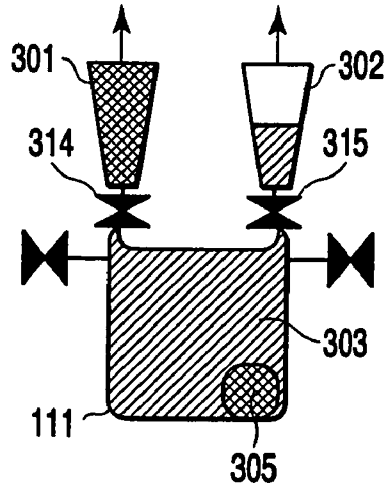

(3)-1-2 Injection of Sample:

The method of injecting a liquid sample 305 containing a nucleic acid material, which is to be newly inspected, into the fluid holding channel 111 loaded in advance with a prescribed amount of the reagent solution will now be described with reference to FIGS. 30A to 30C schematically showing the sample injecting process.

a. Initiation of Sample Injection:

As shown in FIG. 30A, the inlet-outlet valves 314 and 315 are opened with the joining valves 316 and 317 kept closed.

In the next step, the nucleic acid detecting cassette 100 is held such that the opening portions 121 and 122 are positioned on the upper side. Under this condition, the tip 301 of the pipette 300 loaded with the sample 305 to be injected is inserted into the opening portion 121. At the same time, the tip 302 open to the outside is inserted into the opening portion 122 on the opposite side of the opening portion 121. By the mounting of these tips 301 and 302, the setting of the cassette is finished, and the injection of the sample 305 from the tip 301 is started.

b. Termination of Sample Injection:

As shown in FIG. 30B, the sample 305 is injected until the reagent solution 303 is pushed into the tip 302 on the outlet side.

c. Closure of Inlet-Outlet Valve:

Finally, the inlet-outlet valves 314 and 315 are closed, and the tips 301 and 302 are detached from the opening portions 121 and 122, respectively, as shown in FIG. 30C.

Where the sample 305 has a specific gravity larger than that of the reagent 303 and also has a diffusion coefficient smaller than that of the reagent 303, and where the direction of the gravity of the sample 305 is on the side opposite to the side of the inlet-outlet valves 314 and 315 as viewed from the center of the fluid holding channel 111 as denoted by an arrow in FIG. 30C, the sample 305 is positioned by sedimentation on the side right under the fluid holding channel 111, as shown in FIG. 30C.

By the process steps described above, it is possible to inject the nucleic acid material to be inspected into the fluid holding channel 111 that is loaded in advance with a prescribed amount of the reagent while preventing the gas from being involved in the sample and the reagent as air bubbles.

(3)-2 Fluid Transfer:

The method of transferring the fluid among a plurality of fluid holding channels 111 having the reagent injected thereinto by the fluid injecting process will now be described. The fluid transfer method described in the following covers a case where a prescribed amount of the fluid is transferred and another case where the maximum holding amount of the fluid is transferred. Also, the following description covers the case where the fluid is transferred between the fluid holding channel 111*a* and the fluid holding channel 111*b*.

(3)-2-1 Transfer of Prescribed Amount of Fluid:

In the transfer of a prescribed amount of the fluid, a prescribed amount of the fluid is transferred from the fluid holding channel 111*a* holding the maximum amount of the fluid into the fluid holding channel 111*b* holding the minimum amount of the fluid so as to increase the amount of the fluid held in the fluid holding channel 111*b* to reach the maximum holding amount. The minimum holding amount denotes the inner volume in the case where the left side pad 402 and the right side pad 403 shown in FIG. 27 are in the opened state and the central pad 401 shown in FIG. 27 is in the closed state. On the other hand, the maximum holding amount denotes the inner volume in the case where all of the left side pad 402, the right side pad 403 and the central pad 401 are in the opened state.

Figure 31A:
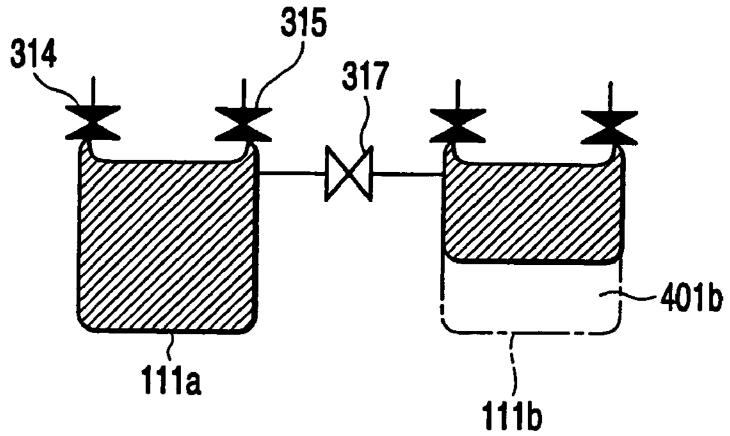
FIGS. 31A to 31C schematically show collectively the process of transferring a prescribed amount of the solution in the fluid holding channel shown in FIG. 2.

The process of transferring a prescribed amount of the fluid will now be described in detail.

a. Opening of Joining Valve:

As shown in FIG. 31A, the joining valve 317 between the fluid holding channel 111*a* and the fluid holding channel 111*b* is put under the opened state. On the other hand, the other joining valves and inlet-outlet valves are kept under the closed state.

Figure 31B:
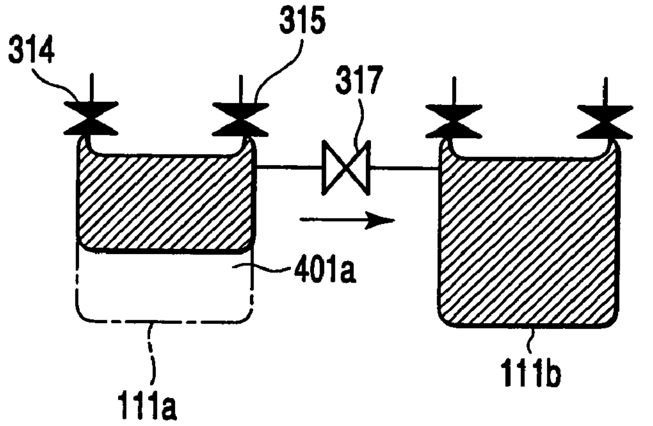

In the next step, the central pad 401*a* of the fluid holding channel 111*a* is slightly pushed in so as to pressurize the fluid such that the joining valve 317 is completely opened. It should be noted that, before the pressurizing step, the flexible sheet 2 constituting the joining valve 317 is pushed against the bottom surface of the joining channel 117 in a manner to eliminate completely the clearance between the flexible sheet 2 and the bottom surface of the joining channel 117. It follows that, even if the locking section 437 of the movable rod 417 for locking the joining channel 117 is released, the flexible sheet 2 in that portion is pushed against the bottom surface by the atmospheric pressure in the case where the resilience of the flexible sheet 2 is weak. Such being the situation, it is possible for the joining valve 317 to fail to be opened completely. However, a restoring force is imparted to the flexible sheet 2 by pressurizing the fluid holding channel 111*a* so as to cause the joining valve 317 to be opened without fail.

b. Start-Up of Fluid Transfer:

As shown in FIG. 31B, the central pad 401*a* of the fluid holding channel 111*a* is pushed in immediately after the central pad 401 of the fluid holding channel 111*b* is opened so as to start up the transfer operation of the fluid.

In this case, it is possible to start the fluid transfer such that the pressure of the fluid holding channel 111*b* is rendered equal to the pressure of the fluid holding channel 111*a* before the central pad 401*a* of the fluid holding channel 111*a* is pushed in.

Figure 31C:
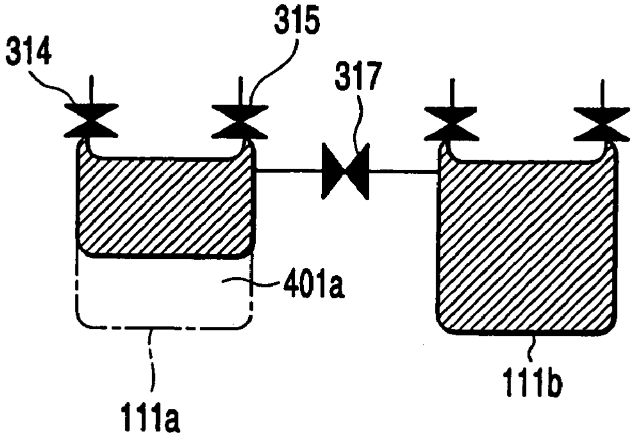

It is possible to put the central pad 401*b* of the fluid holding channel 111*b* under the opened state before the joining channel 117 is opened. In this case, however, a negative pressure is set up within the fluid holding channel 111*b*, with the result that it is possible for the joining channel 117 to fail to be opened smoothly.

c. Termination of Fluid Transfer and Closure of Joining Valve:

As shown in FIG. 31C, the central pad 401*a* of the fluid holding channel 111*a* is set at the completely closed state, followed by setting the joining channel 117 at the completely closed state. In this case, a small amount of the liquid material remaining inside the joining channel 117 is transferred into the fluid holding channel 111*a* and the fluid holding channel 111*b*, with the result that the liquid material inside the joining channel 117 is discharged completely.

In the process of transferring a prescribed amount of the fluid described above, the volume Vt of the fluid that is transferred meets approximately the relationship of Vt=Vmax−Vmin, where Vmax denotes the maximum holding amount of the fluid holding channel, and Vmin denotes the minimum holding amount of the fluid holding channel, in the case where the locking mechanism of the fluid holding channel is of a single stage structure.

(3)-2-2 Fluid Transfer in Maximum Holding Amount:

In the fluid transfer operation in the maximum holding amount, a fluid in the maximum holding amount is transferred from the fluid holding channel 111*a* holding the maximum holding amount to the fluid holding channel 111*b* under the completely closed state, and the amount of the fluid in the fluid holding channel 111*b* is set at the maximum holding amount of the fluid holding channel.

The inner volume under the completely closed state corresponds to the inner volume under the state that all of the central pad 401, the left side pad 402 and the right side pad 403 are closed. Unless the rubber hardness of the flexible sheet 2 is large and unless the seams between the fluid holding channel 111 and each of the inlet-outlet channels 114, 115, and the joining channels 116, 117 are processed smoothly, it is possible for a clearance to be generated within the fluid holding channel 111 even under the completely closed state. However, since a liquid material or fluid in an amount intermediate between the minimum holding amount and the maximum holding amount is injected initially into the fluid holding channel 111, the clearance noted above is filled with a residual liquid material or a residual fluid, with the result that it is impossible for air bubbles to be contained in the fluid holding channel 111.

Figure 32A:
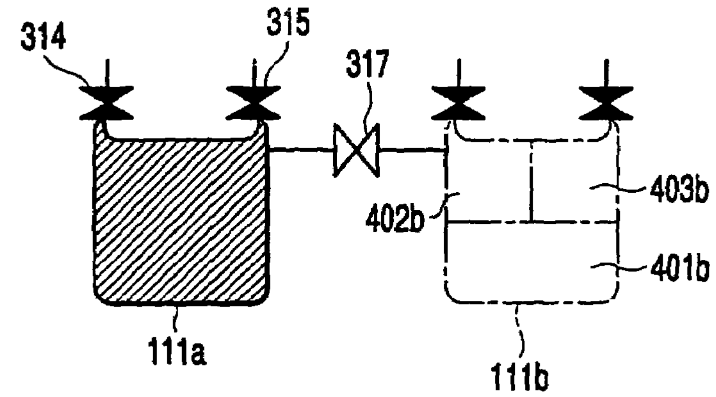
FIGS. 32A to 32D schematically show collectively the process of transferring the maximum holding amount of the solution in the fluid holding channel shown in FIG. 2.

The process of transferring the fluid in the maximum holding amount will now be described.

a. Opening of Joining Valve:

As shown in FIG. 32A, the joining valve interposed between the fluid holding channel 111*a* and the fluid holding channel 111*b* is put under the opened state, with the other joining valves and inlet-outlet valves left under the closed state.

Figure 32B:
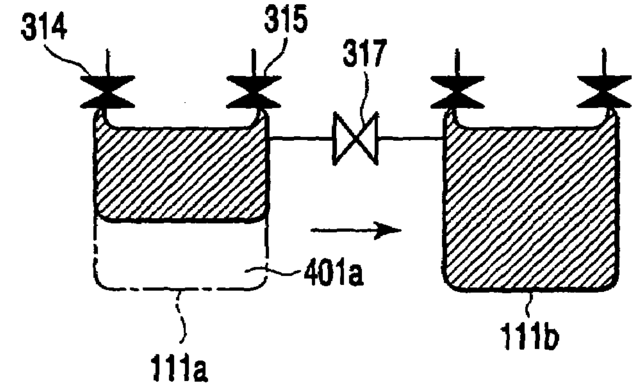
Figure 32C:
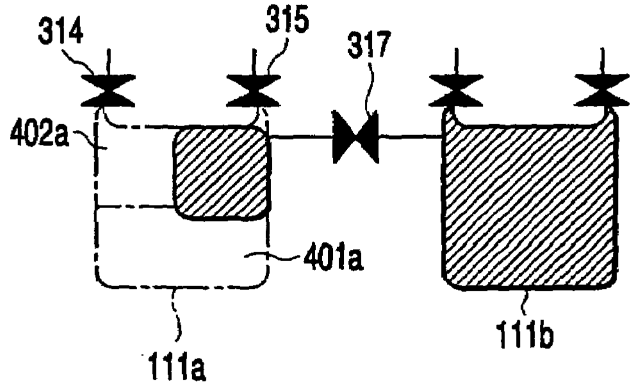
Figure 32D:
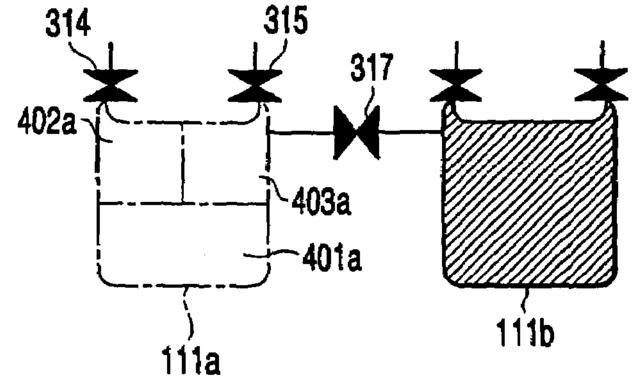

In the next step, the central pad 401*a* of the fluid holding channel 111*a* is slightly pushed in so as to achieve the pressurization such that the joining valve 317 is completely opened.

b. Start-Up of Fluid Transfer:

As shown in FIG. 32B, the central pad 401 of the fluid holding channel 111*a* is pushed in immediately after the central pad 401*a* of the fluid holding channel 111*b* and the left side pad 402*b* are put under the opened state so as to start up the transfer operation of the fluid.

c. Intermediate Stage of Fluid Transfer:

As shown in FIG. 32C, the right side pad 403*b* of the fluid holding channel 111*b* is put under the opened state after the central pad 401*a* of the fluid holding channel 111*a* is put under the completely closed state. Then, the push-in operation of the left side pad 402*a* of the fluid holding channel 111*a* is started. By this intermediate stage of the fluid transfer operation, the fluid within the fluid holding channel 111*a* is directed smoothly toward the joining valve 317. Where the left side pad 402*a* and the right side pad 403*a* of the fluid holding channel 111*a* are pushed in simultaneously, it is possible for the right side pad 403*a* to be put first under the completely closed state because of the processing accuracy and the positional accuracy of the external driving force. In this case, it is possible for a small amount of the liquid material positioned below the left side pad 402*a* to be rendered incapable of transfer toward the joining valve 317.

d. Termination of Fluid Transfer and Closure of Joining Valve:

As shown in FIG. 32D, the further push-in operation of the right side pad 403*a* is started after the left side pad 402*a* is put under the completely closed state so as to bring about finally the situation that the right side pad 403*a* is also put under the completely closed state. By these series of operations, all the pushing pads of the fluid holding channel 111*a* are put under the completely closed state and, thus, the joining channel 117 is put under the completely closed state in the next stage.

It should be noted that the maximum holding amount Vmax of the fluid holding channel 111*b* meets the relationship of Vmax=Vi−Vr, where Vi denotes the total inflow amount into the fluid holding channel, and Vr denotes the amount of the residue in the fluid holding channel.

(3)-2-3 Effects of Fluid Transfer:

The fluid transfer method described above makes it possible to obtain the effect given below:

a. It is possible to transfer the fluid in the equal volume under a small pressure difference.

The inner volume of each channel is variable. However, the inner volume of the entire channel is substantially constant. Also, the pressure difference required for the fluid transfer is generated by varying the inner volume of the variable-volume channel itself. As a result, it is possible to diminish the pressure difference among the channels and the pressure difference between the inner region of the channel and the outside, compared with the fluid transfer system in which pressure is applied to the both edges of the entire channel. It follows that the sealing of the liquid material and the control of the fluid transfer can be performed without fail.

The fluid transfer method described above also makes it possible to produce the effect given below:

b. It is possible to achieve the related motion fluid transfer.

It is possible to drive the system by related moving the pressurizing pads of the fluid holding channels on the fluid transferring side and on the fluid receiving side. In this case, the pushing velocity of the pressurizing pad on the fluid transferring side is made substantially equal to the releasing velocity of the pressurizing pad on the fluid receiving side. It follows that it is possible to diminish further the pressure difference among the channels and the pressure difference between the inner region of the channel and the outside.

(3)-2-4 Air Bubble-Free Closure of the Joining Channel:

In order to ensure the air bubble-free closure of the joining channel, it is possible to introduce a small amount of the reagent into the joining channel so as to load even a small clearance with the liquid material when the liquid material is injected into the fluid holding channel or before the injecting stage of the liquid material. In this case, it is necessary to use a liquid material that does not give adverse effects to the reactions on the fluid holding channels on both sides of the joining channel.

(3)-3 Mixing:

A plurality of reactions are required in the steps of continuously performing the required processing throughout the entire system including the putting of the sample containing nucleic acid, the nucleic acid amplification and other required treatments, and the detection of the target nucleic acid. In the channel system according to the first embodiment of the present invention, various reactions are consecutively carried out by the steps of, for example:

a. Transferring the reaction product within the preceding fluid holding channel into the succeeding fluid holding channel;

b. Mixing the reagent loaded in advance within the succeeding channel with the reaction product transferred into the succeeding channel; and c. Transferring a new reaction product into the succeeding fluid holding channel.

In this fashion, it is possible to realize a consecutive processing. The mixing method of the reagent required for the consecutive processing described above will now be classified into (1) the fluid transfer under the pressurized state within a single channel, (2) the isobaric fluid transfer within a single channel, and (3) the reciprocating fluid transfer between two channels, and will now be described in the classified fashion.

Figure 33A:
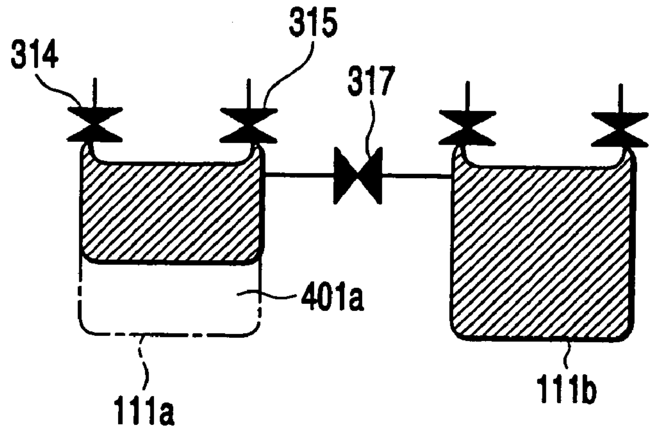
FIGS. 33A and 33B schematically show collectively the process of fluid transfer with pressurizing within the fluid holding channel acting as one of the channels shown in FIG. 2.

(3)-3-1 Fluid Transfer Under Pressurized State within Single Channel:

FIG. 33A schematically shows the channel system in the case where a prescribed amount of the fluid is transferred from the fluid holding channel 111*a* into the fluid holding channel 111*b* so as to put the central pad 401*a* of the fluid holding channel 111*a* under the completely closed state, followed by putting the joining valve 317 under the completely closed state. The amount of the transferred liquid material is about 36 μl in the case where the dimension of the channel system conforms with the dimension according to the example described above.

Under the state that the central pad 401*a* is under the completely closed state and the joining valve 317 is also under the completely closed state as shown in FIG. 33A, the reagent loaded in advance in the fluid holding channel 111*b* is already mixed with the reaction product transferred from the fluid holding channel 111*a*. However, it is possible for the mixture not to be homogeneous. Such being the situation, the fluid transfer under the pressurized state within a single channel is carried out as described in the following.

Figure 33B:
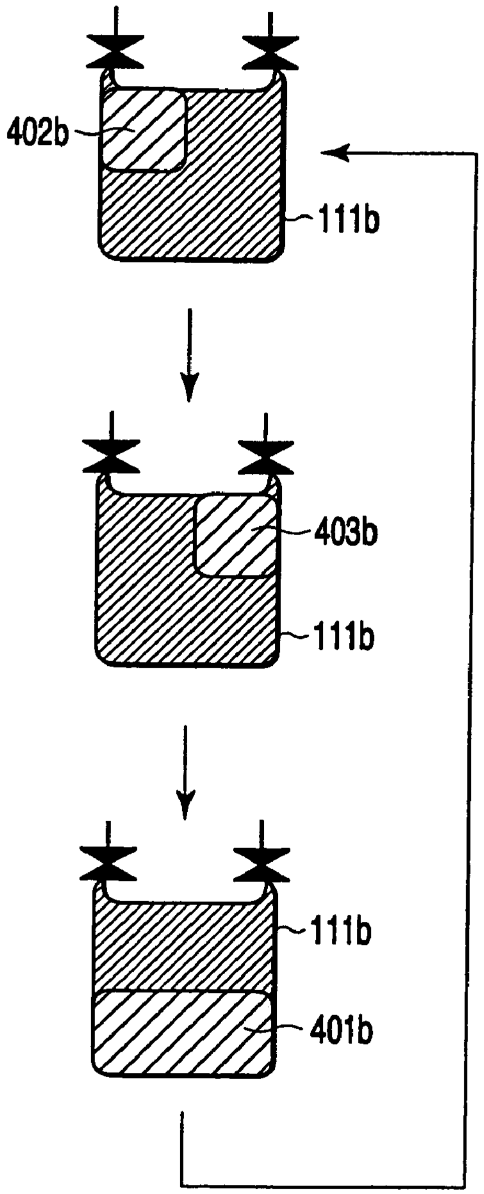

As shown in FIG. 33B, the left side pad 402*b*, the right side pad 403*b* and the central pad 401*b* of the fluid holding channel 111*b* serve to successively push in a prescribed amount of the fluid in the order of the left side pad 402*b*, the right side pad 403*b* and the central pad 401*b* so as to bring about the transfer of the fluid within the fluid holding channel 111*b*. Further, the reaction products can be mixed homogeneously into the reagent within the fluid holding channel 111*b* by changing, for example, the pushing order of the pushing pads, the pushing velocity of the pushing rods, and the value of cycles/sec.

In this mixing method, the fluid holding channel 111*b* holds the fluid up to the maximum holding amount. Therefore, if the pushing amounts of the pushing pads 401*b*, 402*b* and 403*b* are large, the internal pressure of the fluid holding channel 111*b* is increased resulting in the fluid leakage. Such being the situation, it is necessary to control the pushing amounts of the pushing pads 401*b*, 402*b* and 403*b*. The transfer method in which the fluid is pressurized within a single channel corresponding to the fluid holding channel 11*b* so as to bring about the transfer of the fluid within the single channel as shown in FIG. 33B is called the fluid transfer under the pressurized state within a single channel.

Figure 34A:
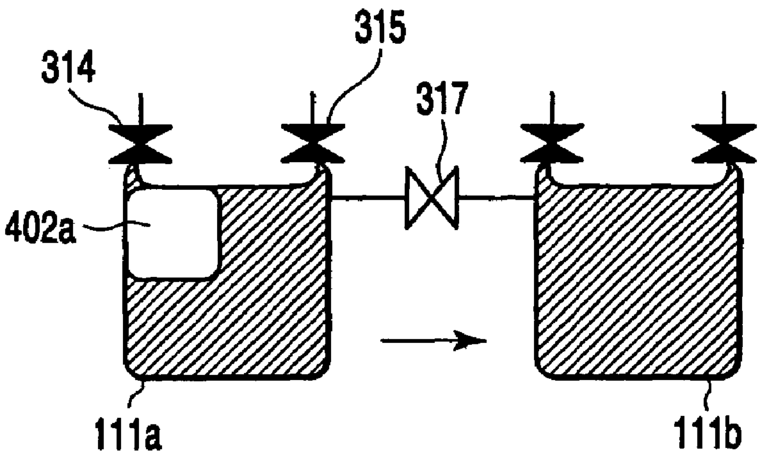
FIGS. 34A and 34B schematically show collectively the process of fluid transfer under an isobaric state within the fluid holding channel acting as one of the channels shown in FIG. 2.

(3)-3-2 Isobaric Fluid Transfer within Single Channel:

It is possible to increase the transfer amount of the fluid inside the fluid holding channel 111*b* without excessively increasing the internal pressure of the fluid holding channel. In this case, a sufficiently large amount of the fluid is supplied into the fluid holding channel 111*b* in the two-stage transfer of the fluid employed in the process of the isobaric transfer within a single channel, which is described herein later, so as to transfer the fluid in an isobaric fashion within the single channel.

a. Initial Fluid Transfer:

As shown in FIG. 34A, the left side pad 402 alone of the fluid holding channel 111*a* is depressed for the initial transfer of the fluid so as to transfer the fluid in an amount of about 24 μl.

b. Initial Mixing:

After about 24 μl of the fluid has been transferred, the joining valve 317 is put under the completely closed state. Under this condition, the left side pad 402*a*, the right side pad 403*b*, and the central pad 401*b* are consecutively pushed down in a prescribed amount as shown consecutively in FIG. 33B. As a result, the transfer of the fluid is brought about inside the fluid holding channel 111*b* so as to achieve the initial mixing of the fluid.

Figure 34B:
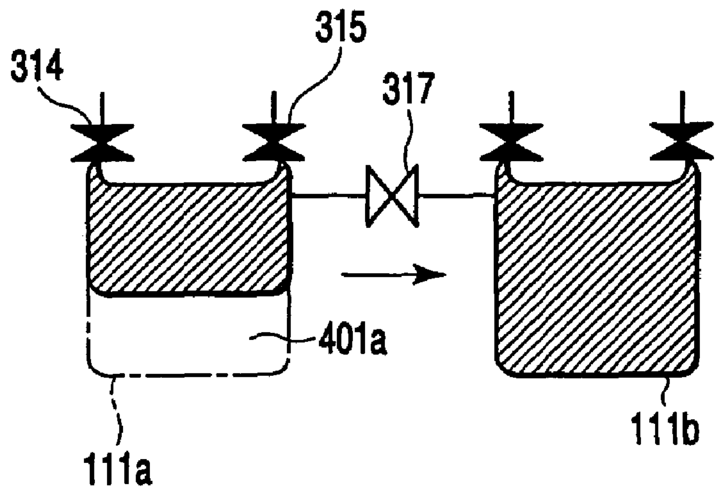

In the example described above, about 24 μl of the fluid is transferred. Since the maximum holding amount of about 48 μl has a sufficient allowance relative to about 24 μl of the transferred fluid, the inner pressure of the fluid holding channel 111*b* is not increased to exceed the external pressure even if the depressing amount of the pushing pad is set relatively large. It follows that it is unnecessary to worry about the fluid leakage. Under this state, it is possible to bring about the transfer of the fluid inside the fluid holding channel 111*b* in an amount that is sufficient for the mixing.

c. Latter Stage Fluid Transfer:

As shown in FIG. 34B, the joining valve 317 is put under the completely opened state, followed by setting the left side pad 402*a* of the fluid holding channel 111*a* at the completely opened state. Under the conditions given above, the latter stage fluid transfer, i.e., setting the central pad 401*a* of the fluid holding channel 111*a* at the completely closed state, is carried out. In this latter stage transfer of the fluid, about 12 μl of the remaining fluid is transferred. It follows that about 36 μl in total of the fluid is transferred in the initial fluid transfer operation and the latter stage fluid transfer operation.

d. Latter Stage Mixing:

The latter stage mixing is carried out under the state that about 36 μl of the fluid noted above has been transferred. After the latter stage fluid transfer, the fluid holding channel

111*a* is under the state equal to the state shown in FIG. 33A. Then, the mixing is carried out under the pressurized state that is consecutively shown in FIGS. 33B, 33C and 33D.

In the latter stage mixing, more than half the amount of the fluid is already mixed. As a result, a sufficient mixing can be achieved even if the depressing amount of each pad is not excessively increased.

In the example described above, the operation is controlled by the amount of the transferred fluid that is regulated by the pad. However, it is possible for the pushing pad to be held at an optional position, for the joining valve 317 to be put under the completely closed state, and for the mixing of the fluid to be carried out within the fluid holding channel 111*b* under an optional transfer amount of the fluid.

(3)-3-3 Reciprocating Fluid Transfer Between Two Channels:

Where a prescribed amount of the fluid is transferred from the fluid holding channel 111*a* into the fluid holding channel 111*b*, it is possible in some cases to employ the intermediate stage of allowing the fluid to flow backward from the fluid holding channel 111*b* into the fluid holding channel 111*a*. In this case, it is possible for the fluid to be reciprocated between the two channels.

Figure 35A:
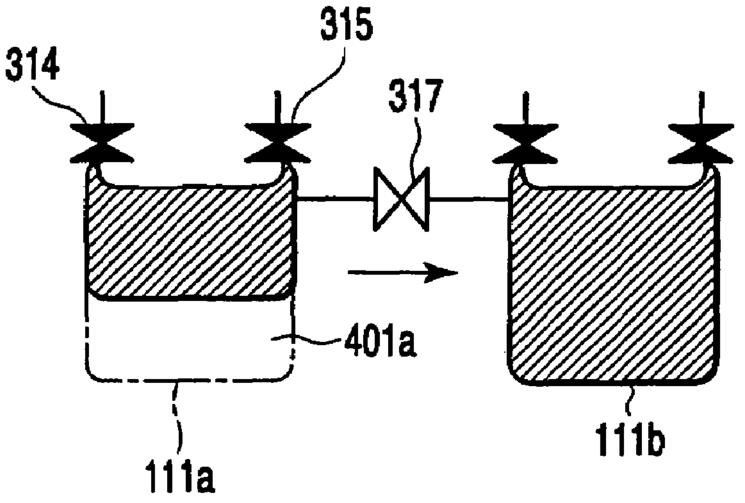
FIGS. 35A and 35B schematically show collectively the process of reciprocating fluid transfer between the fluid holding channels acting as the two channels shown in FIG. 2.
Figure 35A:
Figure 35B:
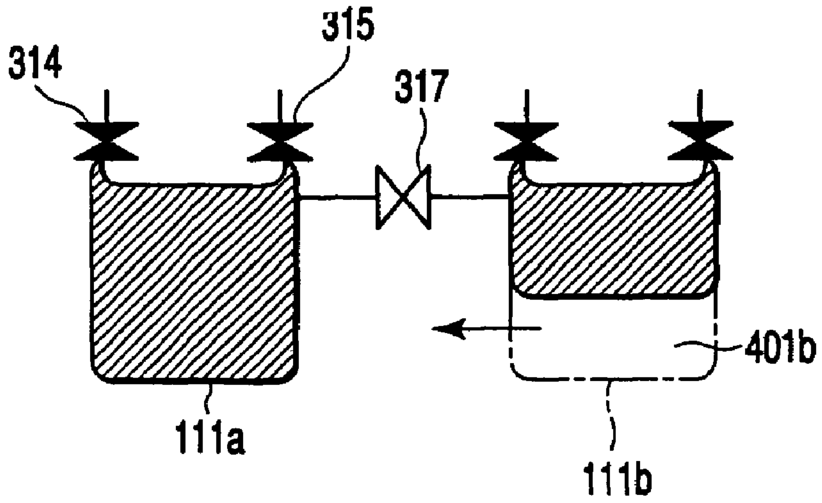

FIGS. 35A and 35B schematically show the situation as to how the fluid is reciprocated between the two channels. In the first step, the fluid is transferred from the fluid holding channel 111*a* into the fluid holding channel 111*b* by the depression of the central pad 401*a* of the fluid holding channel 111*a*, as shown in FIG. 35A. Then, the fluid is transferred from the fluid holding channel 111*b* back into the fluid holding channel 111*a* by the depression of the central pad 401*b* of the fluid holding channel 111*b*, as shown in FIG. 35B. Since the operations shown in FIGS. 35A and 35B are alternately carried out, the fluid can be mixed homogeneously within the fluid holding channel 111*a* and the fluid holding channel 111*b*.

(3)-3-4 Difference in Mixing Ratio:

In the mixing methods of the fluid described above, the case A where it is possible to perform the backward transfer of the fluid between the fluid holding channel 111*a* and the fluid holding channel 111*b* differs from the case B where it is impossible to perform the backward transfer of the fluid noted above. To be more specific, the cases A and B given above differ from each other in the mixing ratio between the reagent and the reaction product. For example, the mixing ratio of the reagent:reaction product is B0:A1 in the case B where the backward transfer cannot be performed, and the mixing ratio of the reagent:reaction product is B0:A0 in the case A where the backward transfer can be performed, where A0 denotes the amount of the reaction product within the fluid holding channel 111*a*, A1 denotes the amount of the reaction product transferred into the fluid holding channel 111*b*, and B0 denotes the amount of the reagent inside the fluid holding channel 111*b*.

Also, the case where the reaction product is partly allowed to remain inside the fluid holding channel 111*a*, from which the fluid is transferred, as a residue that is harmful to the reaction carried out inside the fluid holding channel 111*b* corresponds to the case where it is impossible to perform the backward transfer of the fluid in this mixing method.

(3)-3-5 Effect of Mixing:

Where a plurality of reactions are carried out successively in the gas-liquid two layer system, it was customary in the past to supply the required reagent every time the reaction was carried out in a single reaction chamber. In the method, the amount of the fluid inside the reaction chamber is increased in the every reactions so that a waste liquid chamber is needed, causing a complex channel system. Also, if the amount of the reagent is decreased, it is difficult to control the transfer of the fluid, with the result that a small amount of the reagent remains particularly in inside the long channel. It follows that the waste of the reagent and the nonuniformity in the transfer amount of the fluid are brought about as problems to be solved.

In the fine channel system, it is difficult to stir the fluid within the channel in mixing the different streams of the fluid. Even in the case of using, for example, a combined channel in which different streams of the fluid are combined, it is said to be difficult to achieve a homogenous mixing.

On the other hand, according to the embodiment described above, a relatively large amount of the reaction product itself is transferred, though the amount of the reagent that is transferred is relatively small. Such being the situation, both the transfer and the mixing of the fluid can be controlled easily.

It should also be noted that, in mixing the fluid, it is possible to employ various patterns conforming with the fluid and with the conditions of the reaction. Further, the mixing can be performed under the air bubble-free state. It follows that it is unnecessary to employ a centrifugal separating apparatus for separating the fluid into the gas-liquid two layers.

(3)-4 Modifications:

It is possible to carry out the transfer and mixing of the fluid under more kinds of the volume of the fluid that is held, more kinds of the transfer amount of the fluid, more kinds of the transfer method of the fluid, and more kinds of the mixing method of the fluid by dividing the pushing pad into a larger number of sections and/or forming the locking system for fixing the pushing pad in a manner to have a multi-stage structure in the steps of injecting, transferring and mixing the reagent and the sample. It follows that it is possible to allow the operation in the present invention to conform easily with various fluids and the reacting conditions.

(4) Fluid Transfer Pattern and Order of Fluid Transfer Steps:

(4)-1 Detecting Channel:

(4)-1-1 Detecting Method of Nucleic Acid:

It is possible to use, for example, a known optical system or electrochemical system as the detecting method of the target nucleic acid in the case of using a nucleic acid probe of a single stranded nucleic acid, which has a base sequence complementary to that of the target nucleic acid that is to be detected and which is immobilized inside the detecting channel.

The electrochemical detecting method disclosed in the registered Japanese Patent No. 2,573,443 can be applied basically to the detecting method according to this embodiment of the present invention. Also, it is possible to employ an optical method by using a light transmitting material for forming the stationary base plate 1.

(4)-1-2 Nucleic Acid Detecting Chip:

It is possible to use a detecting base plate 500*a* consisting of a stationary member as the nucleic acid detecting chip 500 acting as a detecting sensor. To be more specific, used is a nucleic acid detecting sensor as disclosed in Japanese Patent Disclosure (Kokai) No. 2002-195997. The detecting sensor used in the present invention employs, for example, the same detecting method, and has the same material used, and the same electrode structure, though the construction disclosed as a prior art in the patent document quoted above is employed in the present invention as the construction of the detecting base plate 500*a*.

Figure 36:
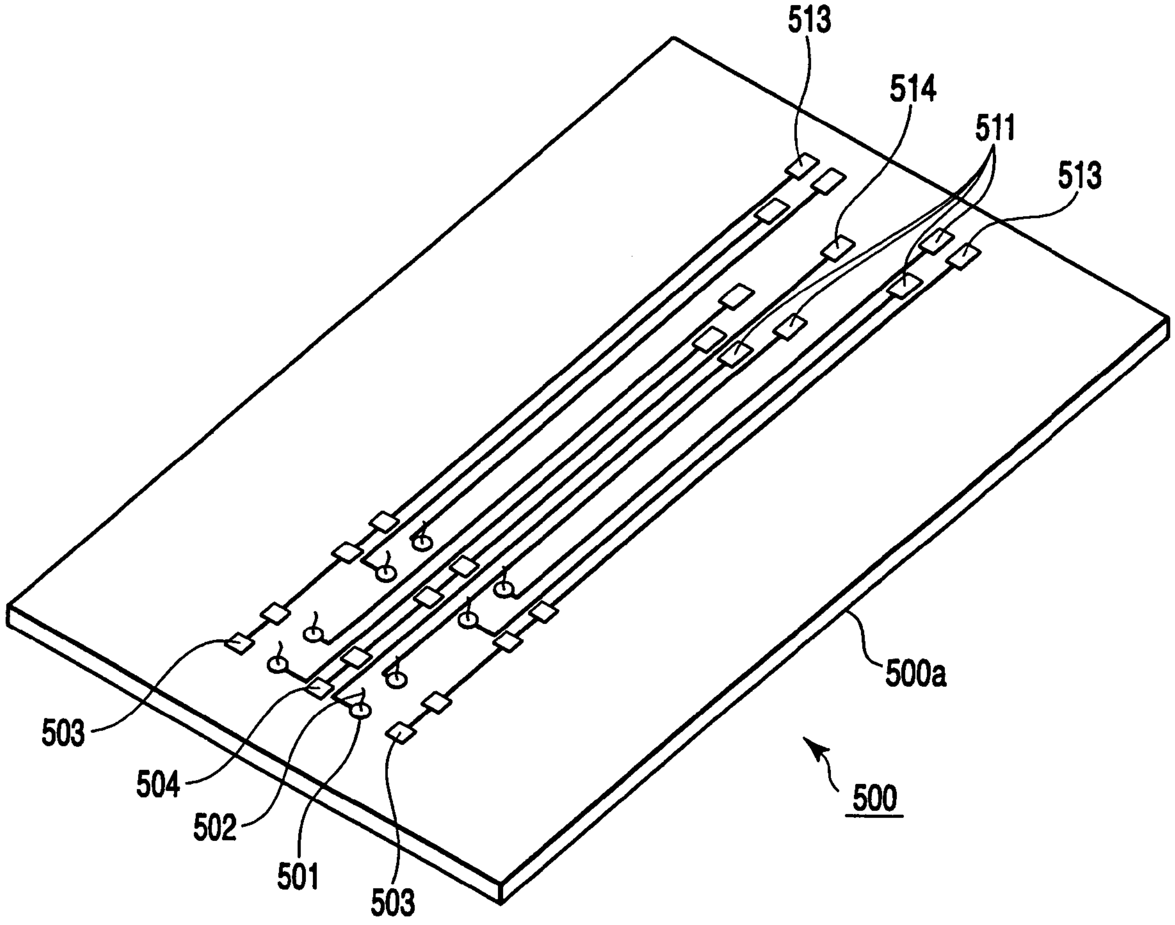
FIG. 36 is an oblique view schematically showing in a magnified fashion the construction of the nucleic acid detecting chip shown in FIG. 2.

FIG. 36 schematically shows the construction of the nucleic acid detecting chip 500. A nucleic acid immobilizing electrode 501, a counter electrode 503 and a reference electrode 504 are formed as disclosed in Japanese Patent Disclosure No. 2002-195997 quoted above on a glass detecting base plate 500*a*. Further, a electric contact 511 for the nucleic acid immobilizing electrode, a electric contact 513 for the counter electrode, and a electric contact 514 for the reference electrode are formed on the glass detecting base plate 500*a* as electric contacts for the exchange of electric signals between these electrodes 501, 503, 504 and the detecting system.

Also, a nucleic acid probe 502 of a single stranded nucleic acid having a base sequence complementary to that of the target nucleic acid to be detected is immobilized on the nucleic acid immobilizing electrode 501 by the method disclosed in Japanese Patent Disclosure No. 2002-195997 quoted above.

Figure 37:
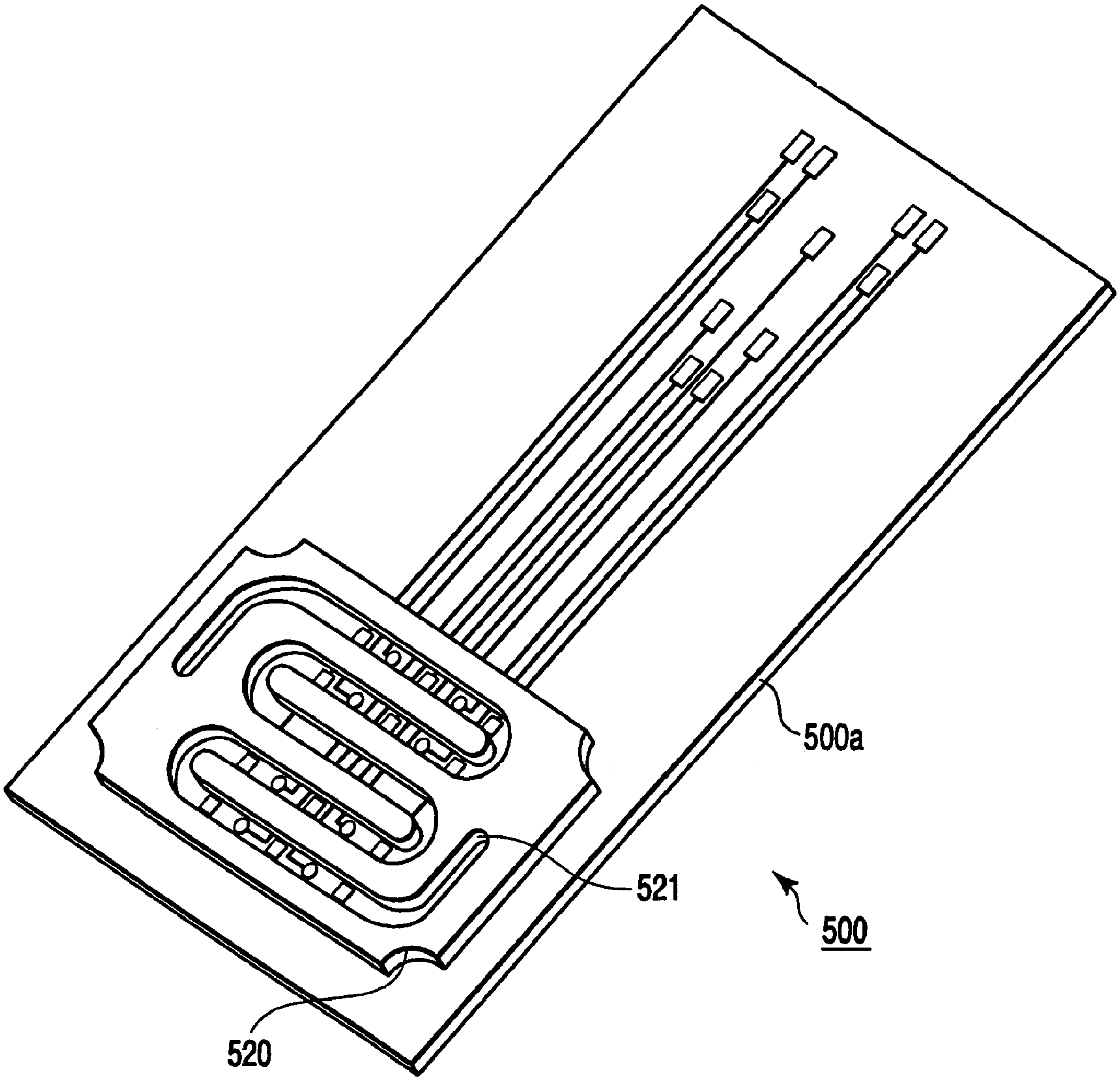
FIG. 37 is an oblique view schematically showing the construction of the nucleic acid detecting chip, shown in FIG. 36, attached a detecting channel seal.

(4)-1-3 Construction of Detecting Channel:

FIG. 37 shows the construction that a detecting channel seal 520 is disposed in a determined position on the nucleic acid detecting chip 500. The detecting channel seal 520, which is a flexible member, can be formed by using a material equal to that of the flexible sheet 2. However, since the detecting channel seal 520 is not locally deformed by the pushing pad, it is also possible to use a material having a relatively high rubber hardness for forming the detecting channel seal 520. As shown in FIG. 37, the detecting channel seal 520 has a zigzag channel opening 521. All of the nucleic acid immobilizing electrode 501, the counter electrode 503 and the reference electrode 504 are positioned inside the channel opening 521. Also, each of the electrodes 501, 503 and 504 is positioned not to be concealed by the detecting channel seal 520, and the nucleic acid detecting chip 500 is arranged in contact with the detecting channel seal 520.

Figure 38:
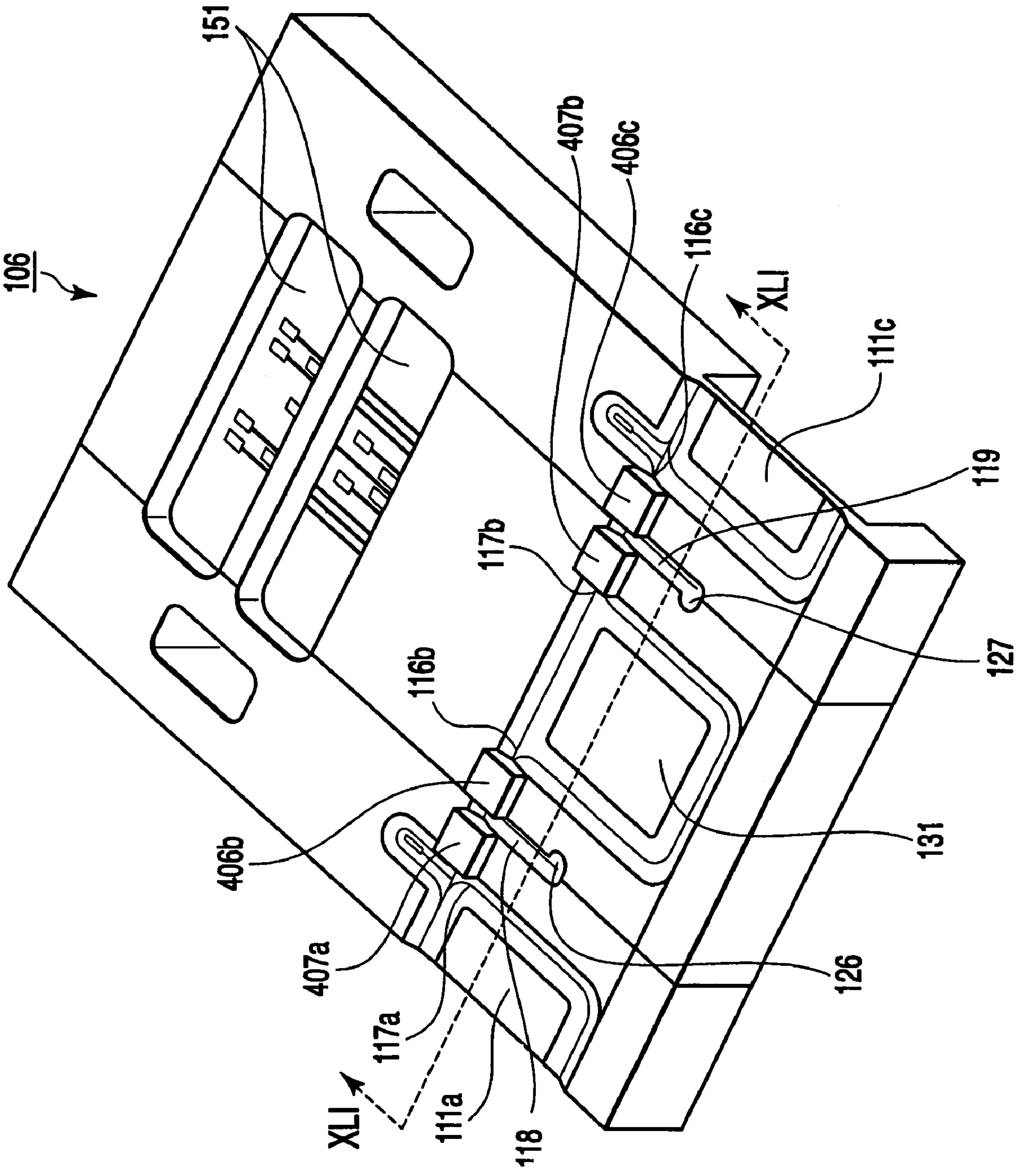
FIG. 38 is an oblique view schematically showing the construction of the detecting section block as viewed from the front side, the detecting section block including the channel base plate shown in FIG. 2.
Figure 39:
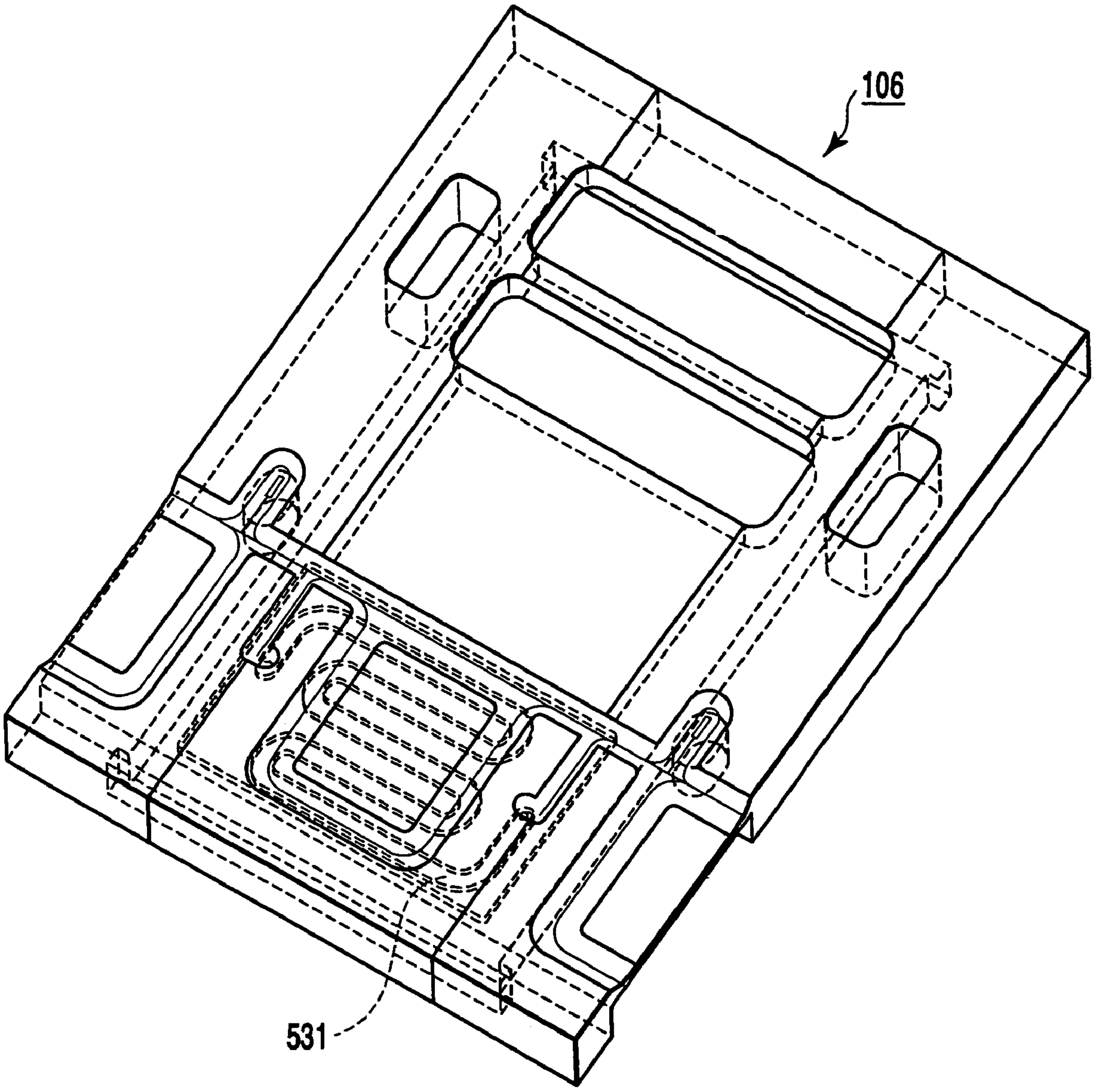
FIG. 39 is an oblique view schematically showing in a perspective fashion the detecting section block shown in FIG. 38 as viewed from the front side.

(4)-1-4 Bonding of Detecting Channel to Base Plate:

FIG. 38 is an oblique view showing the construction of a detecting section block 106 as viewed from the front surface side, FIG. 39 is an oblique view showing in a perspective fashion the detecting section block 106 shown in FIG. 38 as viewed from the front surface side, and FIG. 40 is an oblique view showing the construction of the detecting section block 106 shown in FIG. 38 as viewed from the back surface side. A chip recess 128 having a depth equal to the thickness of the nucleic acid detecting chip 500 and having an area substantially equal to that of the nucleic acid detecting chip 500 is formed on the back surface of the detecting section block 106. Contact point openings 151 are formed in a part of the chip recess 128 in a manner to extend through the detecting section block 106.

A seal recess 125 having a depth substantially equal to the thickness of the detecting channel seal 520, which further extends from the bottom surface of the chip recess 128, is further formed in a part of the chip recess 128. The detecting channel seal 520 is incorporated in contact with the plane of the deepest portion of the seal recess 125. Further, the nucleic acid detecting chip 500 is incorporated in contact with the plane of the deepest portion of the chip recess 128 such that the nucleic acid detecting chip 500 is in contact with the detecting channel seal 520.

Because of the construction described above, formed is a detecting channel 531 isolated from the outside and consisting of the nucleic acid detecting chip 500, the detecting channel seal 520 and the detecting section block 106. It is possible for the nucleic acid detecting chip 500, the detecting channel seal 520 and the detecting section block 106 to be bonded or welded or adhered to each other. Also, the nucleic acid detecting chip 500, the detecting channel seal 520 and the detecting section block 106 are integrally bonded to each other by using a fastening member or a fastening portion so as to form the nucleic acid detecting closed cassette 100.

(4)-1-5 Relationship Between Retreating Channel and Detecting Channel:

The detecting section block 106 shown in FIG. 38 is a block including the retreating channel 131, and the detecting channel 531 is arranged in a lower portion of the retreating channel 131. A left side guide hole 126 and a right side guide hole 127, which are formed to extend through the detecting section block 106, and the detecting channel edge portions 118 and 119, which are formed on the upper surface of the detecting section block 106, are included in the detecting channel 531 so as to form a single channel.

FIG. 39 is an oblique view showing the construction of the detecting section block 106 as viewed from the front surface side like FIG. 38. The positional relationship among the detecting channel 531, each of the recesses, etc., which are formed on the back surface, is denoted by broken lines in FIG. 39.

FIG. 41 is a cross sectional view of the detecting section block 106 along the line XLI—XLI shown in FIG. 38. As shown in FIGS. 38 and 41, the detecting channel 531 is joined to the joining channels 116 and 117 via the edge portions of two channels, i.e., the detecting channel edge portions 118 and 119 arranged in the left side guide hole 126 and the right side guide hole 127.

To be more specific, the left side of the detecting channel edge portion 118 is joined to the fluid holding channel 111*a* via the joining channel 117*a*, and the right side of the detecting channel edge portion 118 is joined to the retreating channel 131 via the joining channel 116*b*. These joining channels can be opened or closed by the corresponding joining pads 407*a* and 406*b*.

Similarly, the left side of the joining channel edge portion 119 is joined to the retreating channel 131 via the joining channel 117*b*, and the right side of the joining channel edge portion 119 is joined to the fluid holding channel 111*c* via the joining channel 116*c*. These joining channels can be opened or closed by the corresponding joining pads 407*b* and 406*c*.

(4)-1-6 Contact Point Opening:

As shown in FIG. 38, the contact point opening 151 for connecting the electric contact 511 for the nucleic acid immobilizing electrode, the electric contact 513 for the counter electrode, and the electric contact 514 for the reference electrode, which are formed on the nucleic acid detecting chip 500, to the detecting system outside the cassette is formed in the detecting section block 106. The position of the nucleic acid detecting chip 500 is determined and he nucleic acid detecting chip 500 is fixed in a manner to permit the contacts 511, 513, 514 to be arranged within the contact point opening 151.

Figure 42:
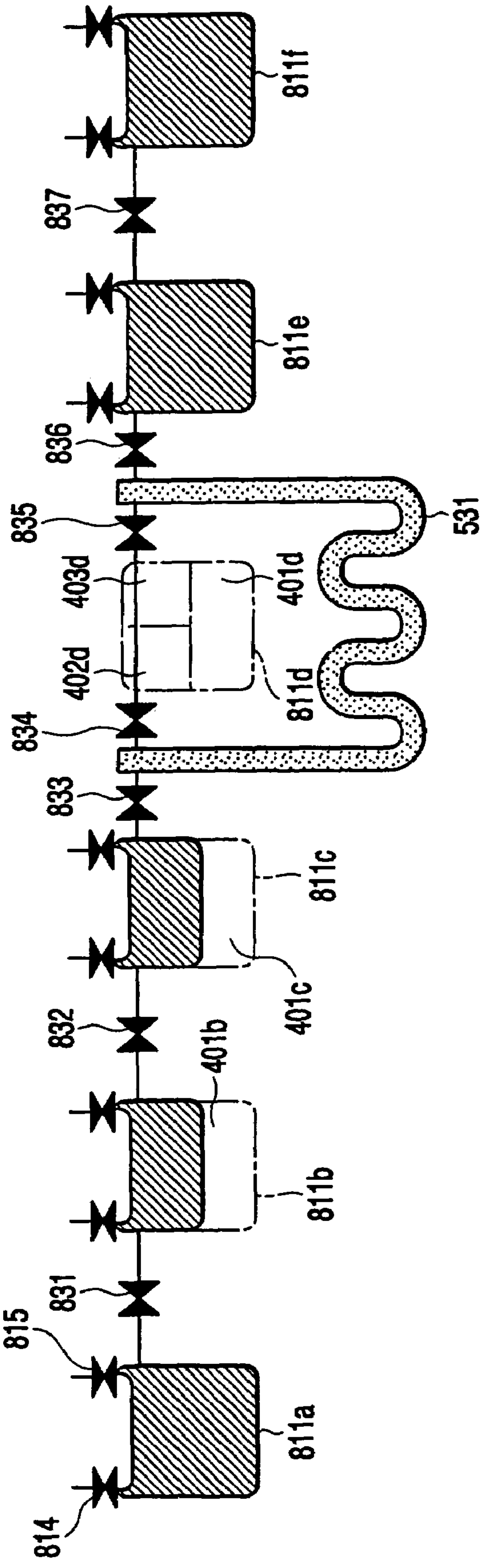
FIG. 42 schematically shows the construction of the channel system, into which all necessary reagents has been initially injected, the channel system being included in the nucleic acid detecting cassette shown in FIG. 2.

(4)-2 Initial Injection:

FIG. 42 schematically shows the channel system of the nucleic acid detecting cassette 100 used in this embodiment of the present invention.

Like FIG. 1, FIG. 42 shows the channel system in which the edge section block 102, the two intermediate section blocks 101, the detecting section block 106, the intermediate section 101, and the edge section block 103 are arranged in the order mentioned as viewed from the left side in the drawing. The edge section block 102 includes a fluid holding channel 811*a*, the first intermediate section block 101 positioned adjacent to the edge section block 102 includes a fluid holding channel 811*b*, and the second intermediate section block 101 positioned adjacent to the first intermediate section block 101 includes a fluid holding channel 811*c*. The detecting section block 106 positioned adjacent to the second intermediate section block 101 includes a retreating channel 811*d* and a detecting channel 531 arranged to bypass the retreating channel 811*d*. The intermediate section block 101 positioned adjacent to the detecting section block 106 on the right side in the drawing includes a fluid holding channel 811*e*. Further, the edge section block 103 on the right side edge in the drawing includes a fluid holding channel 811*f*. The adjacent channels are joined to each other via a joining channel, and a valve is mounted to each of the joining channels so as to make it possible to open or close the joining channels.

The method disclosed in the registered Japanese Patent No. 2,573,443 and Japanese Patent Disclosure No. 2002-195997 can be applied in each of the process steps unless otherwise specified and, thus, attentions should be paid to these patent documents in respect of each of the process steps. First of all, described is the initial state under which all the required reagents are injected for making the nucleic acid detecting system ready for delivery to the market. Also disclosed is the reaction process using each of the reagents.

(4)-2-1 Nucleic Acid Amplification:

In the fluid holding channel 811*a*, reactions such as a polymerase chain reaction (PCR) are carried out from the sample containing nucleic acid so as to amplify nucleic acid within the sample. The amplifying method of nucleic acid is not particularly limited. It is possible to employ various nucleic acid amplifying methods including the method accompanied by the change in temperature such as the polymerase chain reaction (PCR) method and the isothermal amplifying method. It is possible to use, for example, the living body samples such as blood, serum, urine, saliva and a mucous membrane of the mouth as the samples containing nucleic acid. In, for example, the PCR method, a thermal circulation is applied as follows so as to amplify nucleic acid continuously.

a. Heating is applied at 92 to 95° C. for about 10 to 15 seconds so as to denature the double stranded nucleic acid, followed by loosening and separating the double stranded nucleic acid so as to form nucleic acid of a single stranded nucleic acid.

b. Then, nucleic acid is cooled and retained at 55 to 65° C. for about 10 to 15 seconds so as to anneal the primer, thereby allowing the two kinds of the primer to be coupled with the separated single stranded nucleic acid so as to form partially a double stranded nucleic acid.

c. Further, nucleic acid is retained at 70 to 72° C. for about 10 to 15 seconds so as to elongate an additional nucleic acid chain having complementarity with the two kinds of the primer used as the starting point of the nucleic acid synthesis.

For carrying out the PCR method, a buffer solution containing dNTP, primer, polymerase, and other reagents required for the PCR method is injected into the fluid holding channel 811*a*. It is also possible to add, as required, a reagent effective for eliminating the effect of the substance inhibiting the amplification of nucleic acid to the sample solution. For example, it is possible to add “Ampdirect” manufactured by Shimazu Seikakusho K.K. to the sample solution. The reagent effective for eliminating the effect of the substance inhibiting the amplification of nucleic acid is a reagent that permits taking out nucleic acid directly from blood for carrying out the PCR method. The total amount of the reagents injected into the fluid holding channel 811*a* is about 48 μl.

(4)-2-2 Producing Single Stranded Nucleic Acid:

In the fluid holding channel 811*b*, the double stranded nucleic acid, which is amplified in the nucleic acid amplifying process carried out in the fluid holding channel 811*a*, is produced the single stranded nucleic acid by, for example, λexonuclease method. In this stage, the sample is retained at 35 to 39° C. for about 30 minutes to 3 hours in order to maintain the enzyme reaction. Finally, the sample is heated at 92 to 95° C. for about 3 to 6 minutes for deactivating the enzyme. The total amount of about 12 μl of exonuclease and the reagents contained in the buffer solution, which are used in this stage, are injected into the fluid holding channel 811*b*.

(4)-2-3 Impartation of Protective Chain:

In the fluid holding channel 811*c*, the protective chain nucleic acid chain complementary to the sequence of the portion of amplified single stranded nucleic acid sample that is not complementary to the nucleic acid probe 502 is added to the amplified single stranded nucleic acid sample used by the method disclosed in Japanese Patent Disclosure No. 6-70799. As a result, the self-hybridization of the amplified nucleic acid sample can be prevented so as to improve the detection sensitivity. In this stage, the hybridization reaction is carried out, if required, between the protective chain and the nucleic acid sample by retaining the nucleic acid sample at 95 to 98° C. for about 1 to 5 minutes so as to thermally denature nucleic acid, followed by moderately cooling the nucleic acid sample to 25° C. at a cooling rate of 2° C./min. The total amount of about 12 μl of the reagents used in this process are injected into the fluid holding channel 811*b*.

(4)-2-4 Hybridization:

In the detecting channel 531, the nucleic acid sample that was amplified and pretreated and the nucleic acid probe 502 on the nucleic acid immobilizing electrode 501 are retained at a prescribed reaction temperature (e.g., 20 to 40° C. for 30 to 60 minutes) so as to carry out the hybridization reaction. It is possible to dry the nucleic acid probe 502 for the preservation, and cleaned and sterilized gaseous materials such as nitrogen and the air are loaded in the detecting channel 531. In the stage of the hybridization reaction, the detecting channel 531 is loaded with a fluid containing the nucleic acid sample. In the nucleic acid detecting cassette of the closed system, it is impossible to discharge the gaseous material that is initially loaded to the outside. Therefore, the retreating channel 811*d* has an inner volume that permits retreating the gaseous material noted above. The inner volume of the retreating channel 811*d* in the initial state is substantially zero, and the retreating channel 811*d* is closed completely. Alternatively, it is possible to load a fluid such as a buffer solution or a physiological saline in the detecting channel 531 in place of the gaseous material.

(4)-2-5 Washing:

In the detecting channel 531, the nucleic acid immobilizing electrode 501 is washed after completion of the hybridization reaction, and the nucleic acid sample that was not involved in the hybridizing reaction is removed from the surface of the nucleic acid immobilizing electrode 501. In this process, a buffer solution is used as the washing solution. The washing solution used in this process is injected into the fluid holding channel 811*e* and is transferred into the detecting channel 531 when the washing solution is used. The total amount of about 48 μl of all the reagents are injected into the fluid holding channel 811*e*.

(4)-2-6 Electrochemical Measurement:

In the detecting channel 531, an intercalating agent (intercalator), which is a double stranded nucleic acid recognizing body that is selectively coupled with the hybridized the portion of double stranded nucleic acid is allowed to act on the hybridized nucleic acid sample after the washing stage so as to perform the electrochemical measurement. In this electrochemical measurement, a potential higher than the potential at which the intercalating agent carries out the electrochemical reaction is applied so as to measure the reaction current value derived from the intercalating agent. In this stage, the potential is swept at a constant rate. The detection of the target nucleic acid is judged on the basis of the current value thus obtained. Also, the temperature is maintained at, for example, 20 to 25° C. during the measuring process. The intercalating agent used is injected into the fluid holding channel 811*f* and is transferred into the detecting channel 531 when the intercalating agent is used. The total amount of about 48 μl of all the reagents are injected into the fluid holding channel 811*f*.

(4)-3 Fluid Transfer Order:

The nucleic acid detecting cassette 100 for the inspection is supplied to the user under the state that the required reagents are loaded therein as schematically shown in FIG. 42.

(4)-3-1 Nucleic Acid Amplification:

In the first step, the sample containing nucleic acid is injected by opening the inlet-outlet vales 814 and 815. After injection of the sample, the inlet-outlet valves 814 and 815 are closed. Then, as shown in FIG. 42, a prescribed temperature cycle is imparted from a heat transfer means (not shown) to the fluid holding channel 811*a* under the state that the joining valve 831 is closed so as to amplify nucleic acid.

Figure 43:
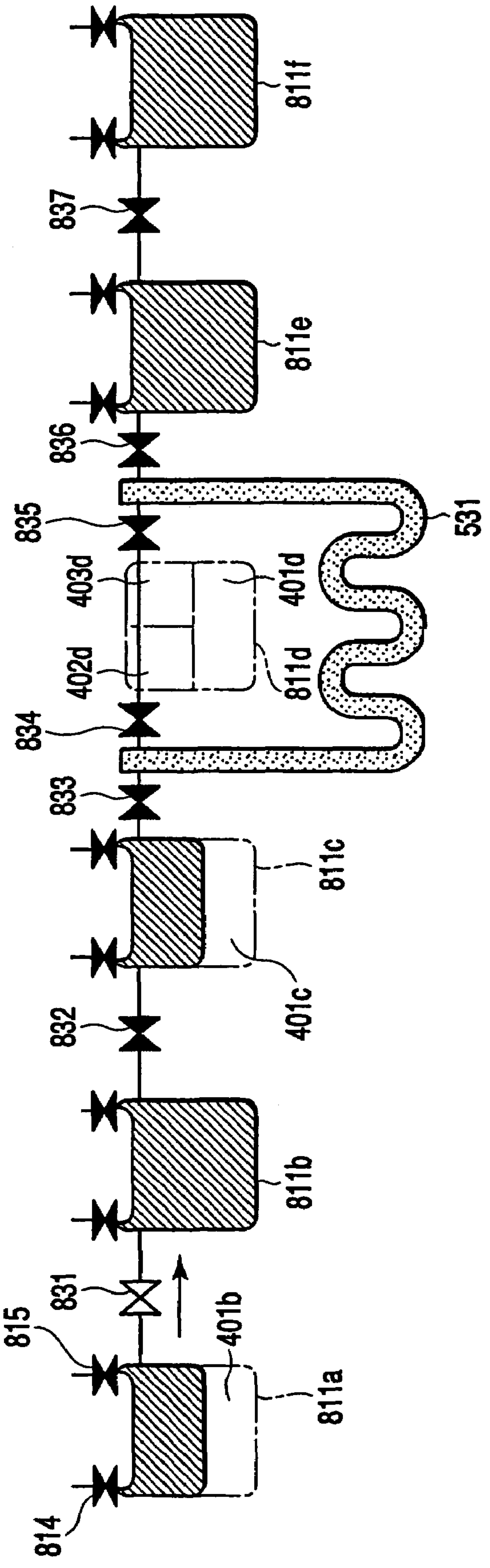
FIG. 43 schematically shows the construction of the channel system included in the nucleic acid detecting cassette shown in FIG. 2 in the reaction process for forming a single stranded nucleic acid.

(4)-3-2 Producing Single Stranded Nucleic Acid:

As shown in FIG. 43, the joining valve 831 is opened after completion of the amplification of nucleic acid so as to push in the central pad 401*a* of the fluid holding channel 811*a*. As a result, the amplified nucleic acid sample, which is the formed product after the reaction, is transferred from the fluid holding channel 811*a* into the fluid holding channel 811*b* in an amount of about 36 μl. In this stage, the reaction product transferred into the fluid holding channel 811*b* is sufficiently mixed with the reagent loaded in the fluid holding channel 811*b*. After completion of the mixing, the joining valve 831 is closed. Then, a prescribed temperature is imparted to the fluid holding channel 811*b* so as to start the reaction for producing the single stranded nucleic acid.

Figure 44:
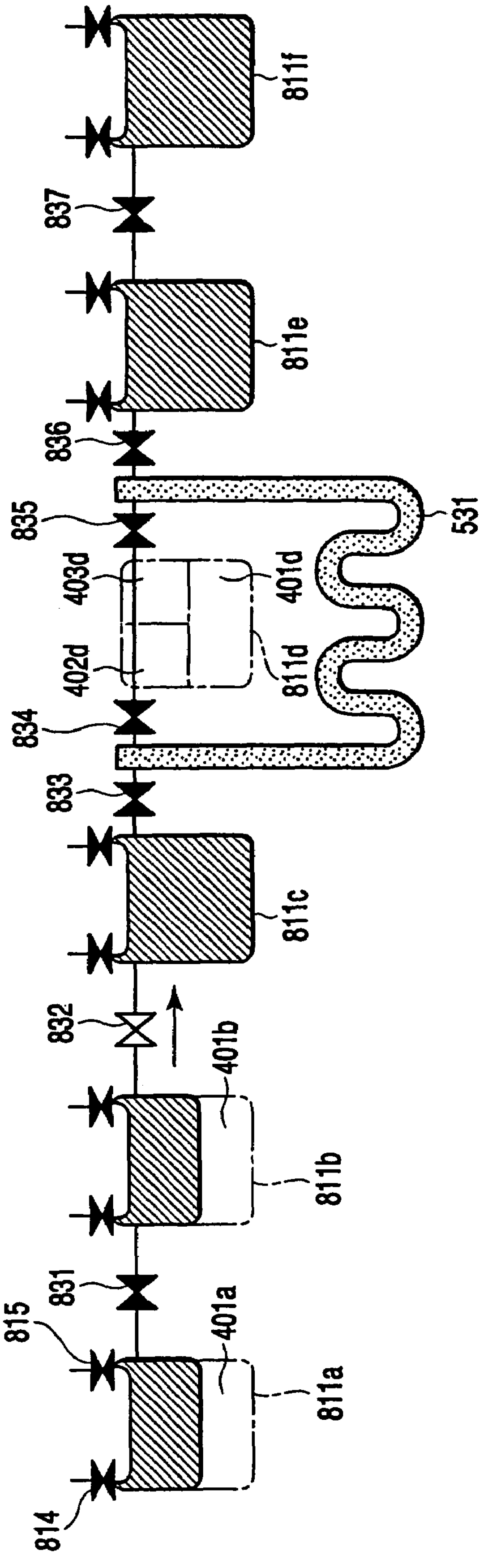
FIG. 44 schematically shows the construction of the channel system included in the nucleic acid detecting cassette shown in FIG. 2 in the reaction process for imparting a protective chain.

(4)-3-3 Impartation of Protective Chain:

As shown in FIG. 44, a joining valve 832 is opened after completion of the reaction for producing the single stranded nucleic acid, and the central pad 401*b* of the fluid holding channel 811*b* is pushed in so as to permit the nucleic acid sample, which is the reaction product that has been converted into the single stranded nucleic acid, to be transferred from the fluid holding channel 811*b* into the fluid holding channel 811*c* in an amount of about 36 μl. In this stage, the reaction product transferred into the fluid holding channel 811*c* is sufficiently mixed with the reagent loaded in the fluid holding channel 811*c*. After completion of the mixing, the joining valve 832 is closed. Then, a prescribed temperature is imparted, as required, so as to start the reaction for imparting a protective chain.

(4)-3-4 Hybridization:

The hybridization process comprises (4a) hybridization, (4b) purging with air, part 1, (4c) transfer of the used reaction product, part 1, and (4d) transfer of the used reaction product, part 2.

Figure 45:
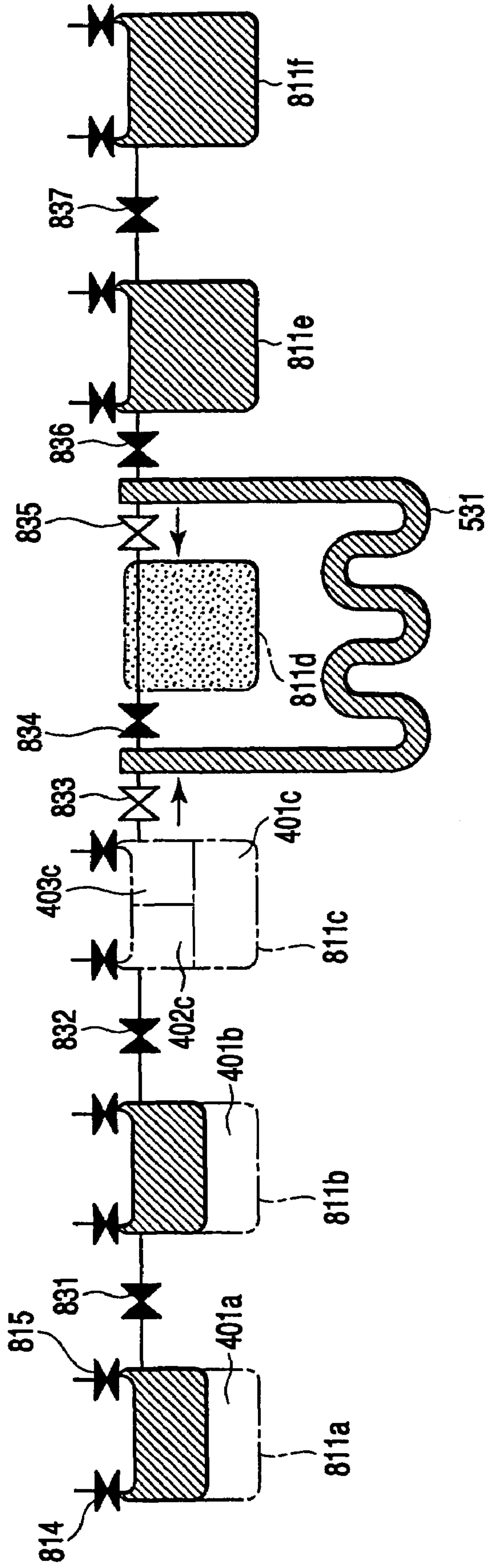
FIG. 45 schematically shows the construction of the channel system included in the nucleic acid detecting cassette shown in FIG. 2 in the hybridization process.

(4)-3-4a Hybridization:

As shown in FIG. 45, the joining valves 833 and 835 are opened after completion of the reaction for imparting the protective chain. Then, the central pad 401*c*, the left side pad 402*c* and the right side pad 403*c* of the fluid holding channel 811*c* are pushed in so as to permit the reaction product of the nucleic acid sample having the protective chain imparted thereto to be transferred from the fluid holding channel 811*c* into the detecting channel 531 in an amount of about 48 μl. At the same time, the locking sections corresponding to the central pad 401*d*, the left side pad 402*d* and the right side pad 403*d* of the retreating channel 811*d* are released so as to cause the loaded gas within the detecting channel 531 to be retreated into the retreating channel 811*d* in an amount of about 48 μl.

In order to permit the nucleic acid probe 502 immobilized within the detecting channel 531 to be rendered sufficiently compatible with the nucleic acid sample transferred into the detecting channel 531 or in order to make the concentration of the nucleic acid sample uniform over the entire region of the detecting channel 531 in the stage of transferring the nucleic acid sample, it is possible to transfer the nucleic acid sample in the reciprocating fashion or in the pulse-wise transferring fashion in addition to the transfer of the nucleic acid sample at a constant fluid transfer velocity. In the case of employing the particular transfer method of the nucleic acid sample, it is possible to suppress the nonuniformity in the measured values of the current. In the reciprocating fashion of transfer the nucleic acid sample, the nucleic acid sample can be transferred from the detecting channel 531 toward the fluid holding channel 811*c* by pushing in the pushing pads of the retreating channel 811*d*, i.e., the central pad 401*d*, the left side pad 402*d* and the right side pad 403*d*. After completion of the transfer of the nucleic acid sample, the joining valves 833 and 835 are closed. Further, after the joining valves 833 and 835 are closed, the detecting channel 531 is maintained at a prescribed temperature so as to start up the hybridization reaction.

Figure 46:
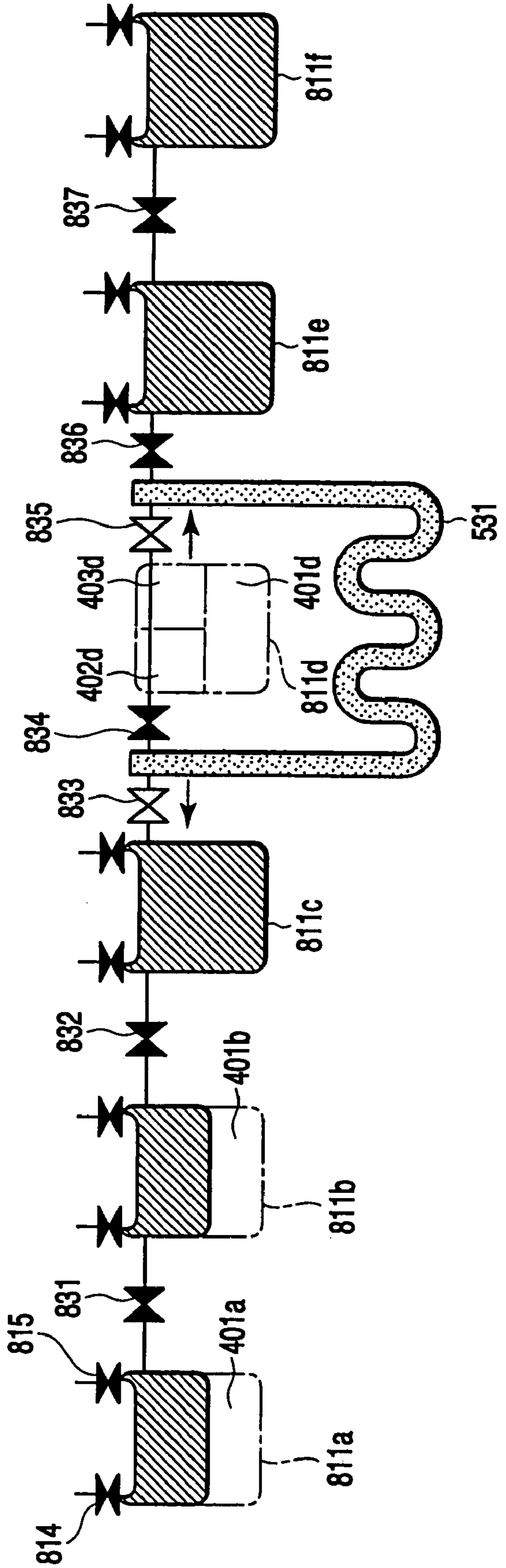
FIG. 46 schematically shows the construction of the channel system included in the nucleic acid detecting cassette shown in FIG. 2 in the process of part 1 for purging with air.

(4)-3-4b Purging with Air, Part 1:

As shown in FIG. 46, the joining valves 835 and 833 are opened after completion of the hybridization reaction. Then, the central pad 401*d*, the left side pad 402*d* and the right side pad 403*d* of the retreating channel 811*d* are pushed in so as to permit the loaded gaseous material in the retreating channel 811*d* to be re-loaded in the detecting channel 531 in an amount of about 48 μl. In this stage, the locking sections corresponding to the central pad 401*c*, the left side pad 402*c* and the right side pad 403*c* of the fluid holding channel 811*c* are released simultaneously so as to permit the nucleic acid sample after completion of the hybridization reaction to be transferred from the detecting channel 531 into the fluid holding channel 811*c* in an amount of about 48 μl. After completion of the transfer of the nucleic acid sample, the joining valves 833 and 835 are closed so as to finish the purging with air, part 1.

Figure 47:
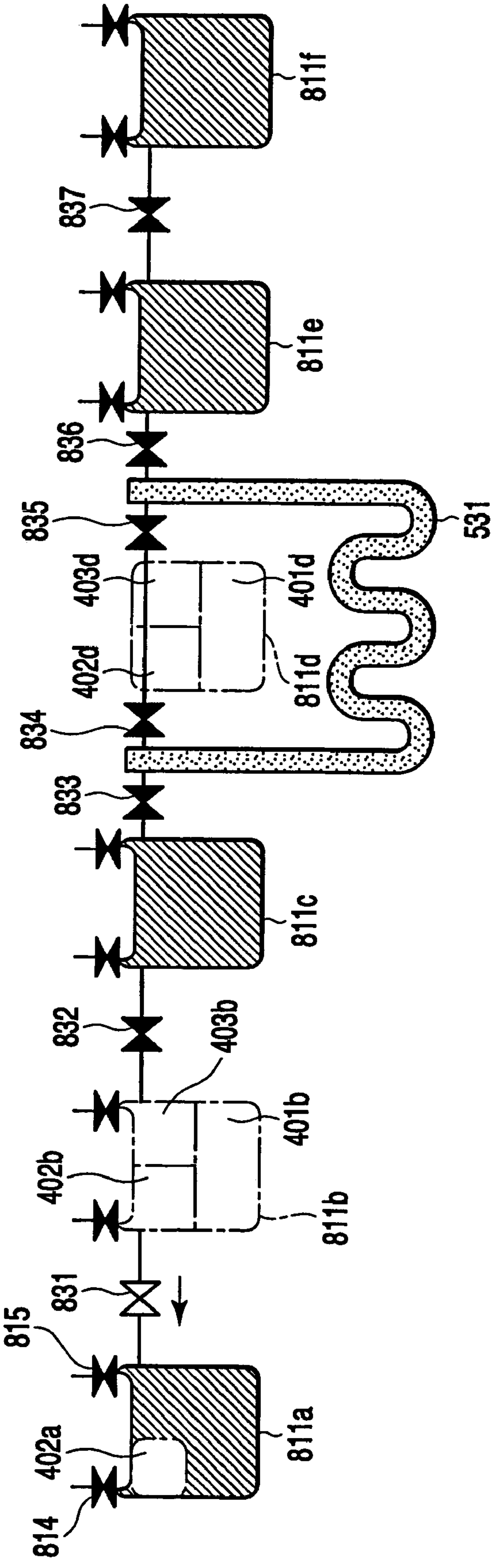
FIG. 47 schematically shows the construction of the channel system included in the nucleic acid detecting cassette shown in FIG. 2 in the process of part 1 for fluidly transferring the used reaction product.

(4)-3-4c Transfer of Used Reaction Product, Part 1:

As shown in FIG. 47, the joining valve 831 is opened after completion of the purging with air, part 1, of the detecting channel 531. Then, the left side pad 402*b* and the right side pad 403*b* of the fluid holding channel 811*b* are further pushed in so as to form a completely closed state. As a result, the residual liquid material inside the fluid holding channel 811*b* is transferred into the fluid holding channel 811*a* in an amount of about 12 μl. In this stage, the fluid holding channel 811*a* is under the state that the left side pad 402 alone is closed, and the inner volume of the fluid holding channel 811*a* is maintained at about 24 μl. As a result, a negative pressure is not set up in the fluid holding channel 811*a*. After completion of the transfer of the residual liquid material, the joining valve 831 is closed.

Figure 48:
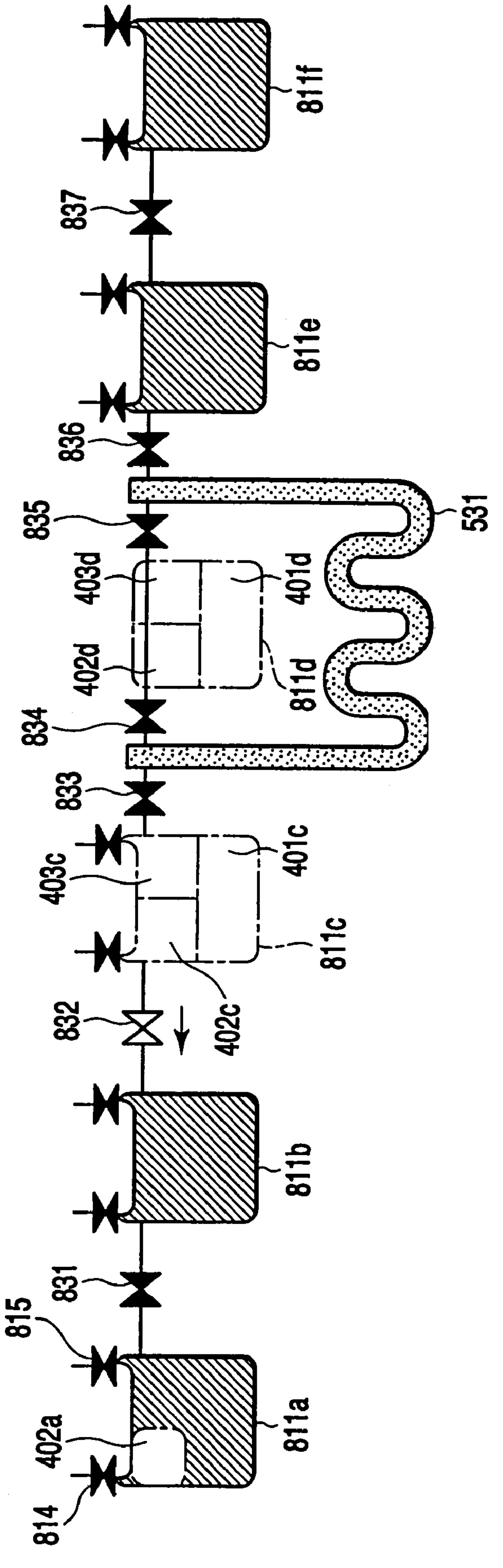
FIG. 48 schematically shows the construction of the channel system included in the nucleic acid detecting cassette shown in FIG. 2 in the process of part 2 for fluidly transferring the used reaction product.

(4)-3-4d Transfer of Used Reaction Product, Part 2:

As shown in FIG. 48, the joining valve 832 is opened after transfer of the residual liquid material inside the fluid holding channel 811*b* and, then, the central pad 401*c*, the left side pad 402*c* and the right side pad 403*c* of the fluid holding channel 811*c* are pushed in. As a result, the nucleic acid sample after completion of the hybridization reaction is transferred further from the fluid holding channel 811*c* into the fluid holding channel 811*b* in an amount of about 48 μl. In this stage, the locking sections of the central pad 401*b*, the left side pad 402*b* and the right side pad 403*b* of the fluid holding channel 811*b* are under the opened state. After completion of transfer of the nucleic acid sample, the joining valve 832 is closed.

(4)-3-5 Washing:

The washing process includes (5a) washing and (5b) purging with air, part 2.

Figure 49:
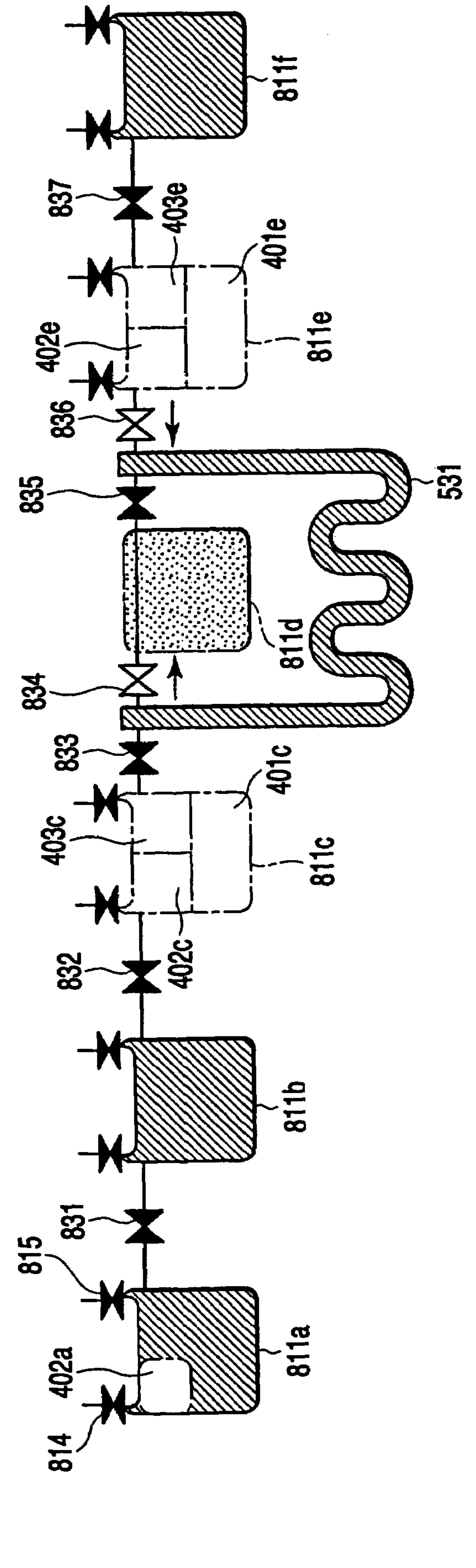
FIG. 49 schematically shows the construction of the channel system included in the nucleic acid detecting cassette shown in FIG. 2 in the washing process.

(4)-3-5a Washing:

As shown in FIG. 49, the joining valves 834 and 836 are opened after transfer of the residual liquid material inside the fluid holding channel 811*c*. Then, the central pad 401*e*, the left side pad 402*e*, and the right side pad 403*e* of the fluid holding channel 811*e* are pushed in so as to permit the washing solution to be transferred from the fluid holding channel 811*e* into the detecting channel 531 in an amount of about 48 μl. At the same time, the locking sections of the central pad 401*d*, the left side pad 402*d* and the right side pad 403*d* of the retreating channel 811*d* are opened so as to permit the loaded gaseous material inside the detecting channel 531 to retreat into the retreating channel 811*d* in an amount of about 48 μl.

In order to remove without fail the nucleic acid sample that was not hybridized with the nucleic acid probe 502 from the surface of the nucleic acid immobilizing electrode 501 in the stage of transferring the washing solution, it is possible to transfer the washing solution in a reciprocating fashion or in a pulse-wise transfer fashion in addition to the transfer fashion at the constant fluid transfer velocity of the washing solution. In this case, it is possible to suppress the nonuniformity in the measured values of the current.

In the reciprocating fashion of transfer the washing solution, the washing solution can be transferred from the detecting channel 531 toward the fluid holding channel 811*e* by pushing in the pushing pad of the retreating channel 811*d*. After completion of the transfer of the washing solution, the joining valves 834 and 836 are closed.

Figure 50:
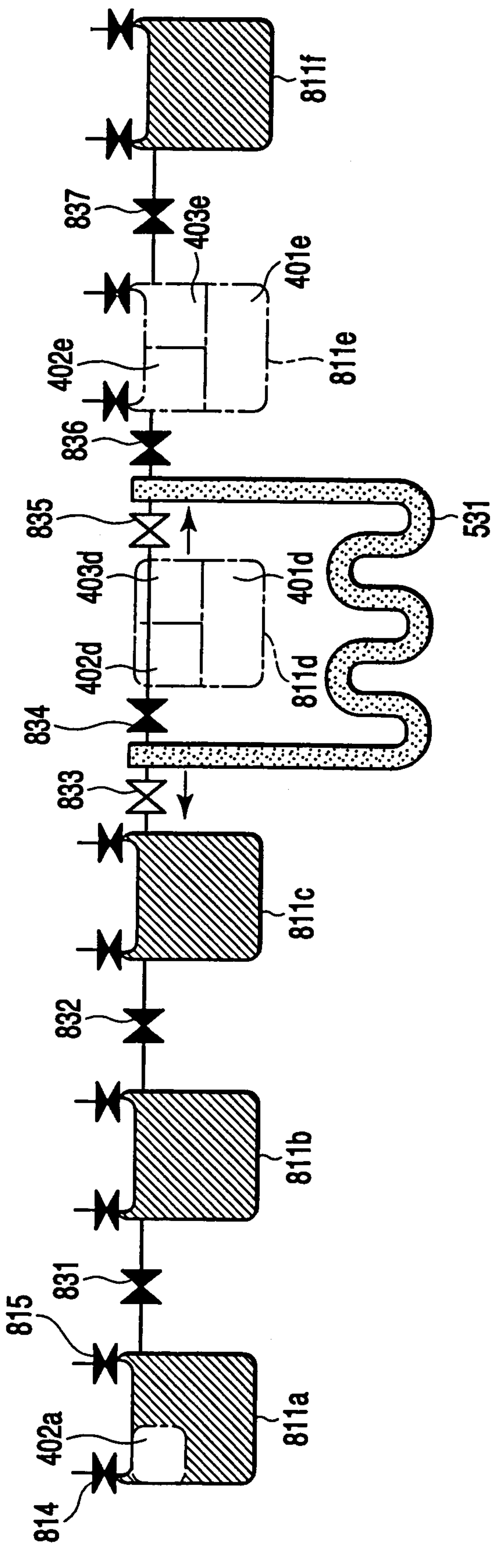
FIG. 50 schematically shows the construction of the channel system included in the nucleic acid detecting cassette shown in FIG. 2 in the process of part 2 for purging with air.

(4)-3-5b Purging with Air, Part 2:

As shown in FIG. 50, the joining valves 835 and 833 are opened after completion of the washing treatment, and the central pad 401*d*, the left side pad 402*d* and the right side pad 403*d* of the retreating channel 811*d* are pushed in. As a result, the gaseous material loaded in the retreating channel 811*d* is re-loaded in the detecting channel 531 in an amount of about 48 μl. At the same time, the locking sections of the central pad 401*c*, the left side pad 402*c* and the right side pad 403*c* of the fluid holding channel 811*c* are opened so as to permit the washing solution after completion of the washing treatment to be transferred from the detecting channel 531 into the fluid holding channel 811*c* in an amount of about 48 μl. After completion of the transfer of the washing solution, the joining valves 833 and 835 are closed, thereby finishing the purging with air, part 2, of the detecting channel 531.

(4)-3-6 Electrochemical Measurement:

The electrochemical measurement includes (6a) transfer of the intercalating agent, and (6b) transfer of the intercalating agent and electrochemical measurement.

Figure 51:
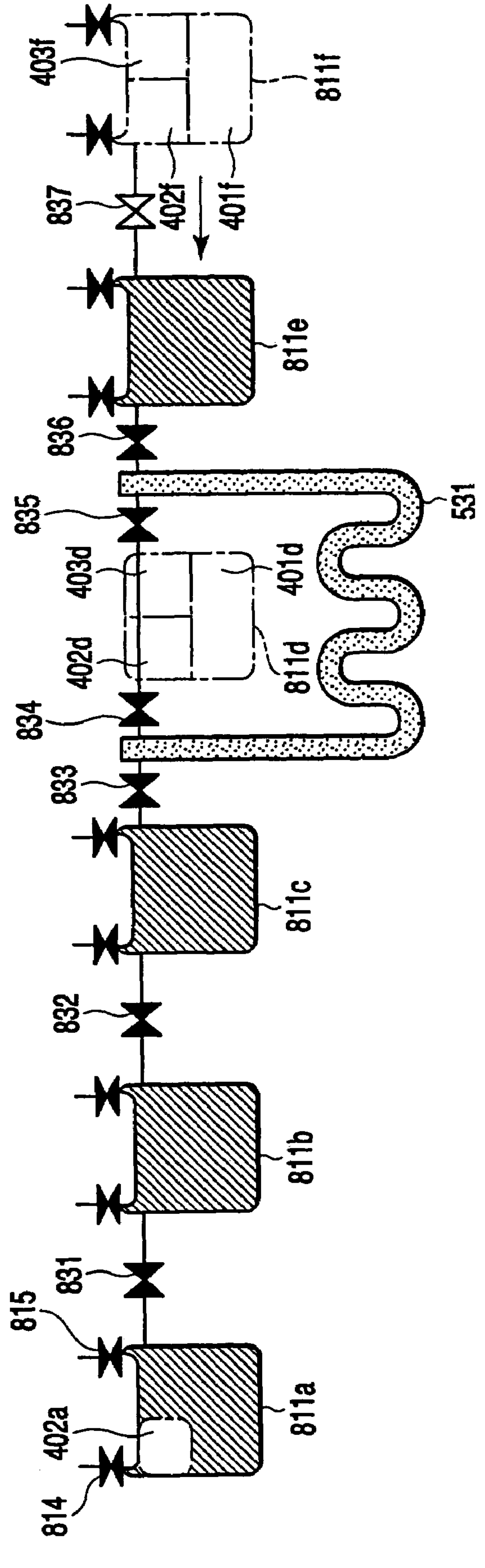
FIG. 51 schematically shows the construction of the channel system included in the nucleic acid detecting cassette shown in FIG. 2 in the process of fluidly transferring the intercalating agent.

(4)-3-6a Transfer of Intercalating Agent:

As shown in FIG. 51, the joining valve 837 is opened after the purging with air, part 2, and the central pad 401*f*, the left side pad 402*f*, and the right side pad 403*f* of the fluid holding channel 811*f* are pushed in so as to permit the intercalating agent to be transferred from the fluid holding channel 811*f* into the fluid holding channel 811*e* in an amount of about 48 μl. In this stage, the locking sections of the central pad 401*e*, the left side pad 402*e* and the right side pad 403*e* of the fluid holding channel 811*e* are under the opened state. After completion of the transfer of the intercalating agent, the joining valve 837 is closed.

Figure 52:
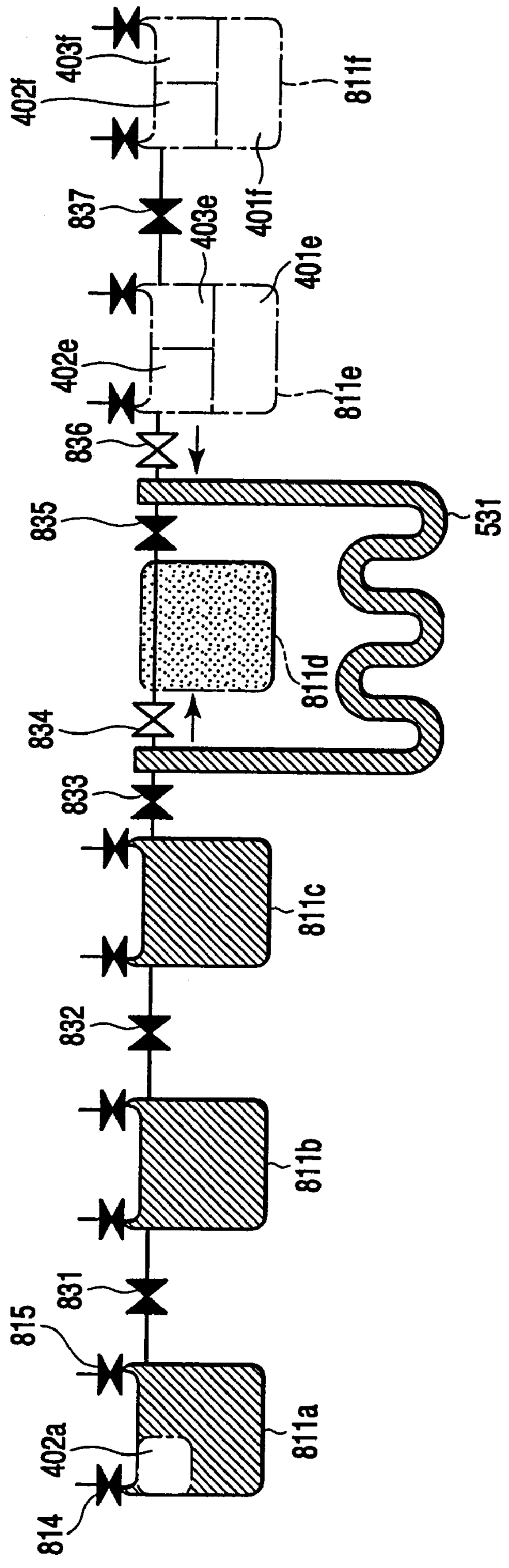
FIG. 52 schematically shows the construction of the channel system included in the nucleic acid detecting cassette shown in FIG. 2 in the fluidly transferring process of the intercalating agent and in the electrochemical measuring process.

(4)-3-6b Transfer of Intercalating Agent and Electrochemical Measurement:

As shown in FIG. 52, the joining valves 834 and 836 are opened after the transfer of the intercalating agent, and the central pad 401*e*, the left side pad 402*e* and the right side pad 403*e* of the fluid holding channel 811*e* are pushed in. As a result, the intercalating agent is transferred from the fluid holding channel 811*e* into the detecting channel 531 in an amount of about 48 μl. At the same time, the locking sections corresponding to the central pad 401*d*, the left side pad 402*d* and the right side pad 403*d* of the retreating channel 811*d* are released so as to permit the gaseous material loaded in the detecting channel 531 to be retreated into the retreating channel 811*d* in an amount of about 48 μl.

In order to allow the intercalating agent to act sufficiently on the hybridized nucleic acid probe 502 immobilized within the detecting channel 531, or in order to make uniform the concentration of the intercalating agent over the entire region of the detecting channel 531, it is possible to transfer the intercalating agent in a reciprocating fashion or in a pulse-wise transfer fashion in addition to the transfer fashion at a constant transfer rate. In this case, it is possible to suppress the nonuniformity in the measured values of the current.

In the reciprocating fashion of transfer the intercalating agent, the intercalating agent can be transferred from the detecting channel 531 toward the fluid holding channel 811*e* by pushing in the pushing pad of the retreating channel 811*d*. After completion of the transfer of the intercalating agent, the joining valves 834 and 836 are closed. After the joining valves 834 and 836 are closed, the detecting channel 531 is maintained at a prescribed temperature so as to start the electrochemical measurement.

(4)-3-7 Effect Produced by Consecutive Reaction Operation:

As described above, the a nucleic acid detecting closed cassette 100 having a variable-volume channel structure produces prominent effects as summarized below:

a. The reagent can be injected without causing a harmful air bubble to be involved in the reaction and in the transfer of the liquid material.

b. Since the joining channel can be arranged with the minimum length, the free space and the residual liquid material are scarcely held in the joining channel.

c. Since there is no pressure difference between the inside and the outside of the reagent fluid holding channel, the fluid leakage need not be worried about during storage of the reagent over a long period of time.

d. The fluid leakage need not be worried about during the transfer stage of the liquid material because there is no pressure difference in pressure between the inside and the outside of the reagent fluid holding channel.

e. The reagent and the reaction product can be mixed each other easily, and a satisfactory reaction can be carried out.

f. A complex pattern in the transfer of the liquid material can be employed in the hybridization process, the washing process and the reaction process with the intercalating agent so as to make it possible to suppress the final nonuniformity in the measured values of the current.

(5) Heat Transfer Unit:

The construction of the heat transfer unit will now be described in detail with reference to FIGS. 53 to 56.

Figure 53:
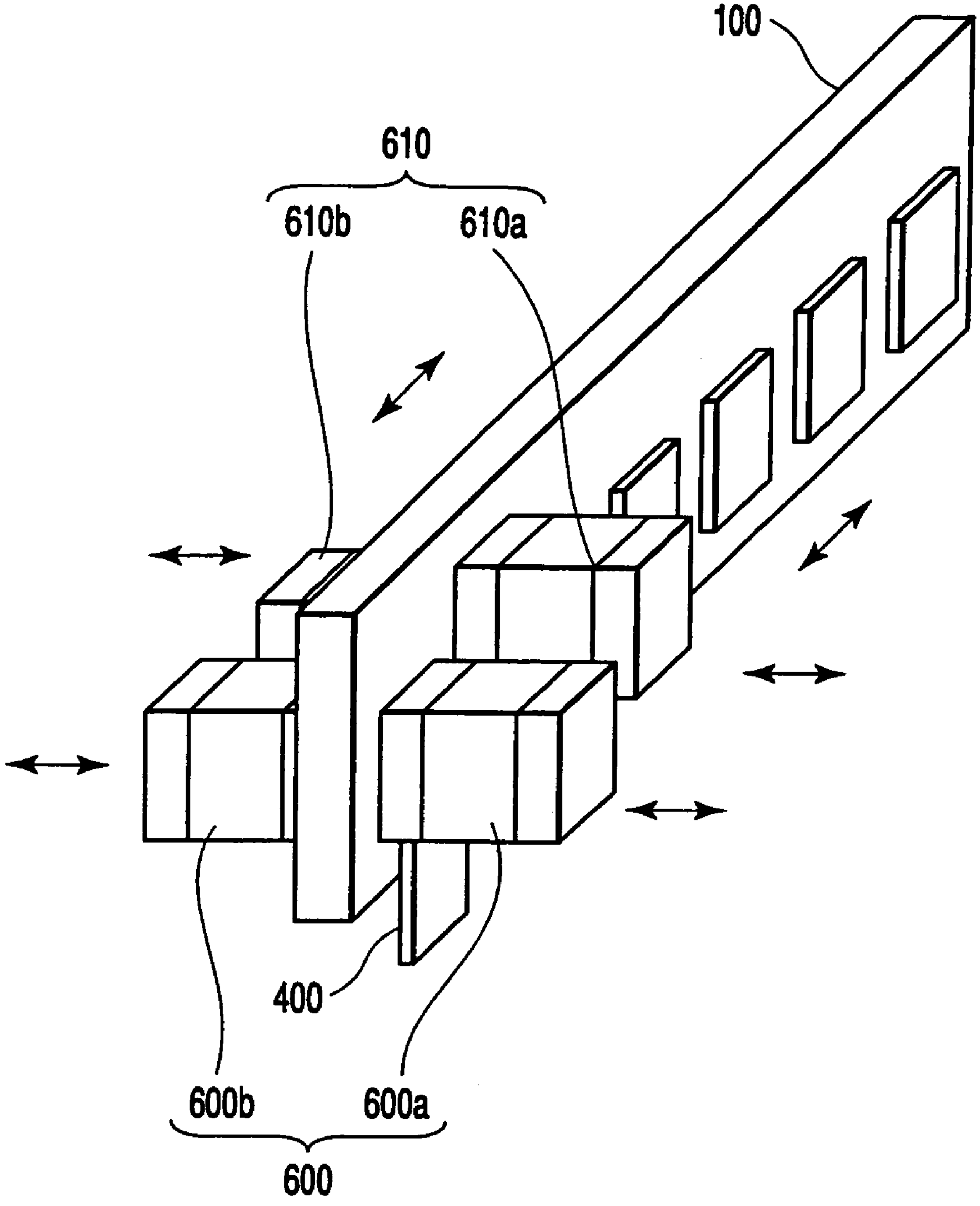
FIG. 53 is an oblique view schematically showing as an example the construction of the system of the heat transfer units arranged in the nucleic acid detecting closed cassette shown in FIG. 2 in the stage of transmitting heat to the nucleic acid detecting cassette.
Figure 54:
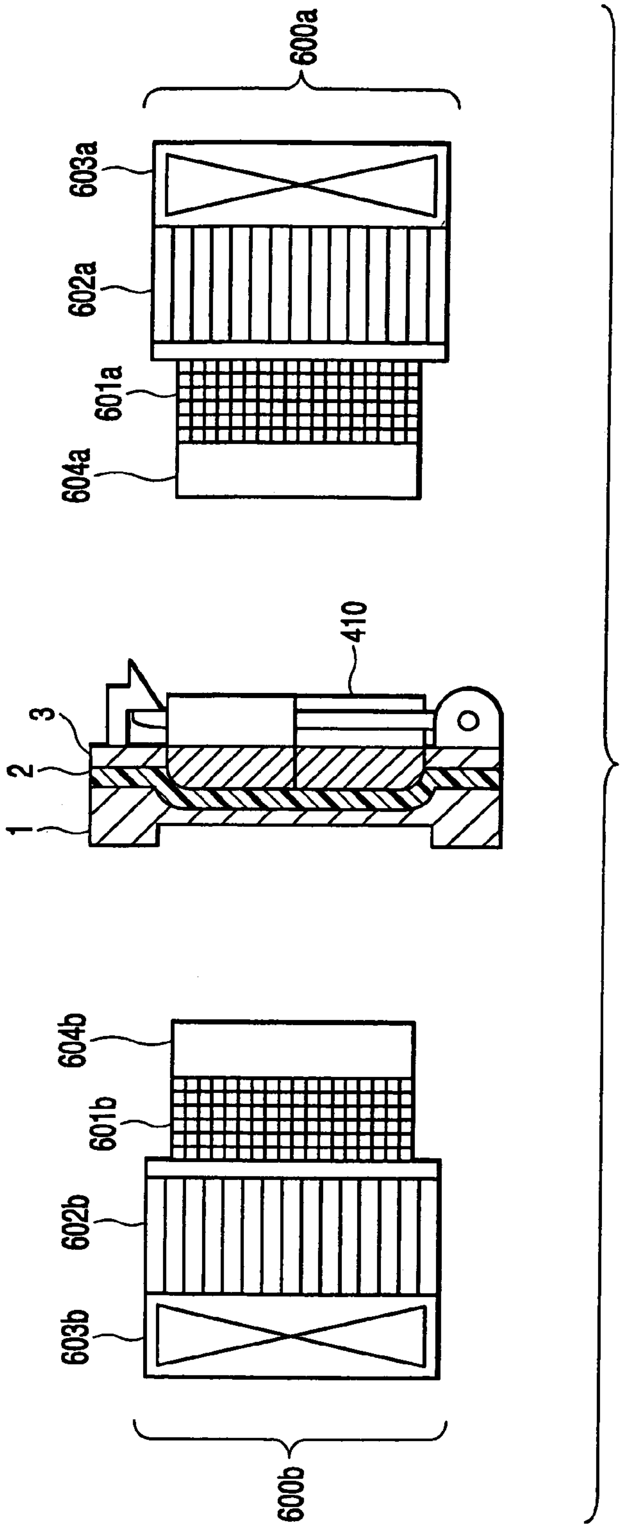
FIG. 54 is a cross sectional view schematically showing the state that the heat transfer unit shown in FIG. 53 is detached from the nucleic acid detecting cassette.
Figure 55:
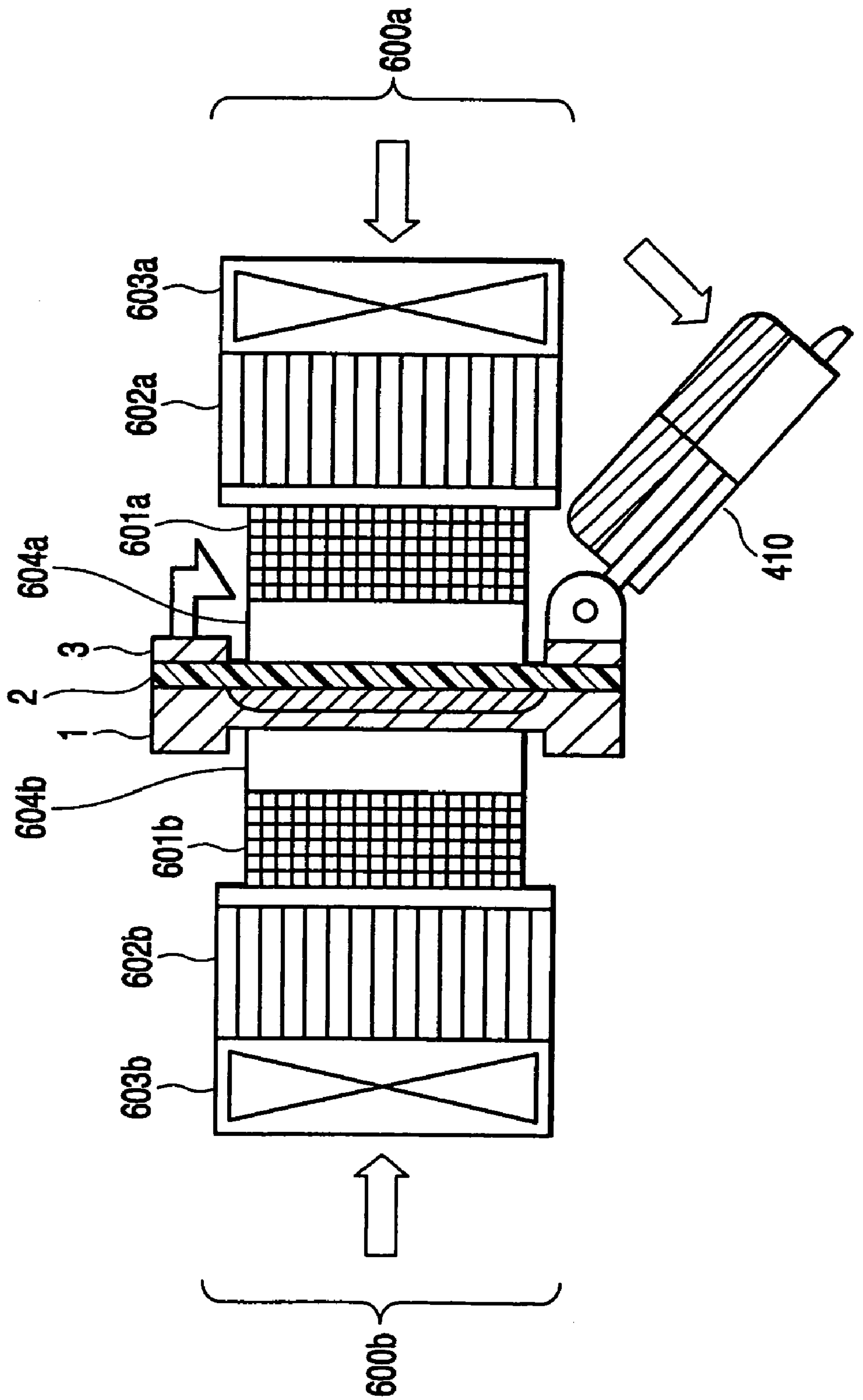
FIG. 55 is a cross sectional view schematically showing the state that the heat transfer unit shown in FIG. 53 is brought into contact with the nucleic acid detecting cassette.

FIG. 53 is an oblique view exemplifying the construction of a heat transfer unit 600 consisting of two heat transfer blocks 600*a* and 600*b*, the heat transfer unit 600 being used in the stage of transferring heat to the nucleic acid detecting cassette 100. FIG. 54 is a cross sectional view showing the state that the heat transfer blocks 600*a* and 600*b* are positioned apart from the nucleic acid detecting cassette 100. Further, FIG. 55 is a cross sectional view showing the state that the heat transfer blocks 600*a* and 600*b* are in contact with the nucleic acid detecting cassette 100.

(5)-1 Construction of Heat Transfer Unit:

As shown in FIG. 54, the heat transfer unit 600 is used for imparting a temperature circulation to the PCR process and, thus, it is necessary for the heat transfer unit 600 to be capable of performing both heating and cooling. Such being the situation, the heat transfer block 600*a* consists of a Peltier element 601*a*, a contact pad 604*a* made of a metal having a high thermal conductivity such as aluminum or copper, a heat sink 602*a* and a cooling fan 603*a*. A grease prepared by mixing a powder having a high thermal conductivity such as an alumina powder with a base oil such as a silicone oil is used for achieving the bonding between the Peltier element 601*a* and the contact pad 604*a* and between the Peltier element 601*a* and the heat sink 602*a*. The heat transfer unit 600 also comprises a temperature sensor (not shown) for measuring the temperature of the nucleic acid detecting cassette 100 or prescribed portions of the heat transfer blocks 600*a*, 600*b*, 610*a* and 610*b* or for controlling the temperature of the nucleic acid detecting cassette 100 or prescribed portions of the heat transfer blocks 600*a*, 600*b*, 610*a* and 610*b*. Incidentally, the heat transfer blocks 600*a*, 600*b*, 610*a* and 610*b* are substantially equal to each other in construction.

(5)-2 Contact of Heat Transfer Unit with Cassette:

FIG. 54 shows the initial state of the arrangement of the heat transfer unit 600. The pushing block 4 consisting of the central pad 401, the left side block 402 and the right side block 403 and corresponding to the fluid holding channel 111 is under the closed state. Under this state, the heat transfer units 600 and 610 are movable relative to the nucleic acid detecting cassette 100 and can be arranged at optional positions of the nucleic acid detecting cassette 100.

FIG. 55 shows the heat transfer state of the heat transfer unit 600 to the nucleic acid detecting cassette 100. In this stage, the pushing block 4 is under the completely opened state achieved by further opening the pushing block 4 that is under the opened state. Where the pushing block 4 is under the completely opened state, it is possible for the heat transfer block 600*a* to transfer heat through the flexible sheet 2 to the liquid material inside the channel. In view of the situation that the flexible sheet 2 has a thickness of about 0.3 mm, the thickness of the stationary base plate 1 forming the back surface of the fluid holding channel 111 is set at about 0.4 mm so as to make the conditions of the heat transfer from both sides substantially equal to each other. In this fashion, the heat transfer blocks 600*a* and 600*b* perform the heat transfer to the fluid holding channel 111 performing the heat transfer to the nucleic acid detecting cassette 100. It should be noted that the heat transfer blocks 600*a* and 660*b* are in contact with both surfaces of the fluid holding channel 111 and, thus, the heat transfer to the fluid holding channel 111 is performed from both sides of the fluid holding channel 111.

Figure 56:
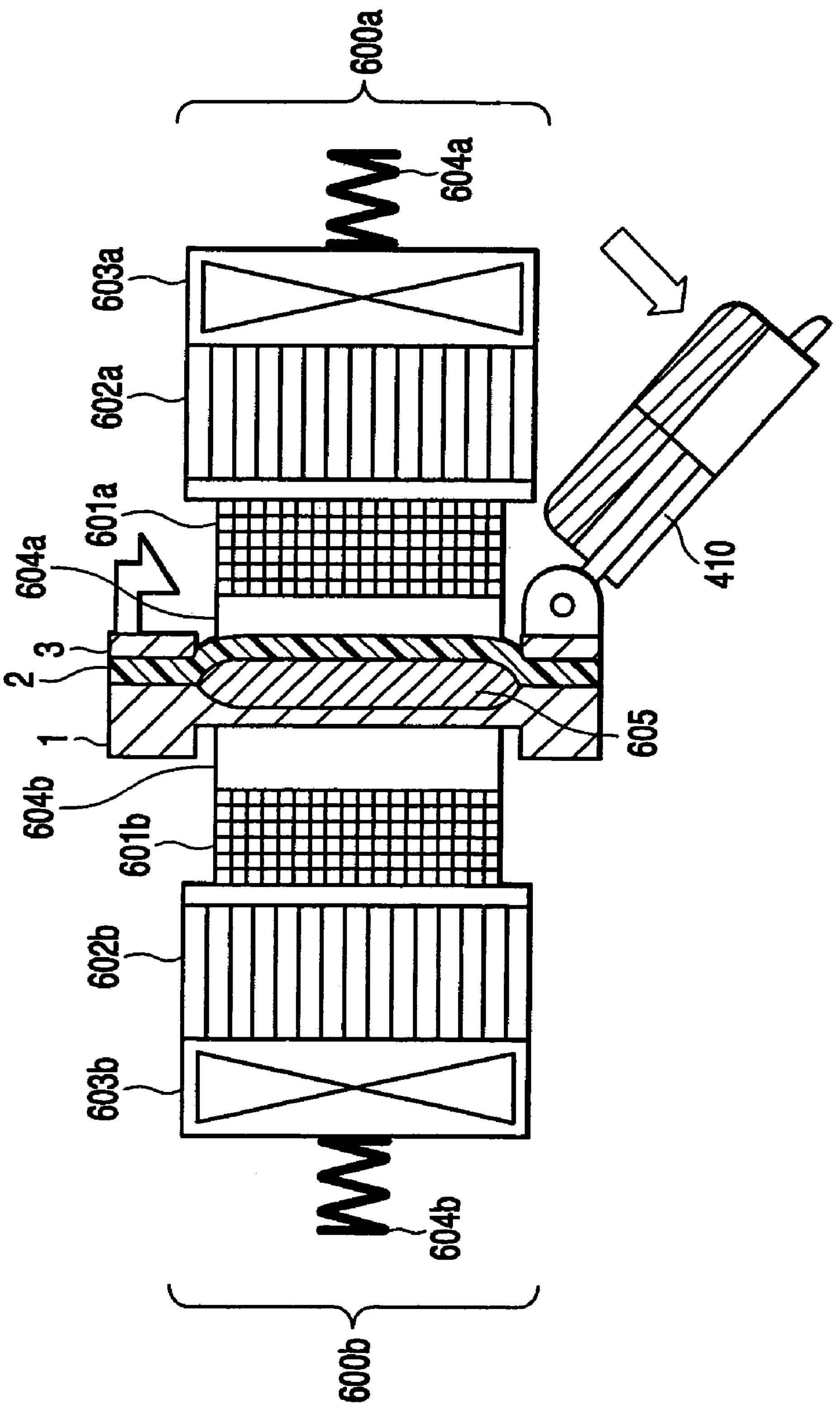
FIG. 56 is a cross sectional view schematically showing the state that the heat transfer unit shown in FIG. 53 is brought into contact with the nucleic acid detecting cassette.

(5)-3 Expansion of Flexible Sheet Toward Outside:

FIG. 56 schematically shows the situation that the liquid material 605 inside the channel is thermally expanded by the heat transfer from the heat transfer unit 600. A prescribed load is imparted to the heat transfer blocks 600*a* and 600*b* by pushing springs 604*a* and 604*b* serving to push the heat transfer unit. If the liquid material 605 inside the channel is thermally expanded, the flexible sheet 2 is expanded toward the outside of the nucleic acid detecting cassette 100 so as to increase the volume inside the channel. As a result, the pressure elevation inside the channel is moderated even during the heating stage so as to make it possible to prevent the liquid material 605 inside the channel from leaking to the outside of the nucleic acid detecting cassette 100 and to the inside of the other channel in accordance with the pressure elevation. Particularly, it is possible to moderate the rapid pressure fluctuation inside the channel accompanying the rapid thermal circulation in the nucleic acid amplifying stage performed by the PCR method. It follows that the heat transfer unit of the present invention is effective for preventing the fluid leakage inside the channel during the nucleic acid amplifying stage.

In order to moderate the pressure elevation inside the channel by the expansion of the flexible sheet 2 toward the outside of the nucleic acid detecting cassette 100 and in order to perform the heat transfer by maintaining the contact of the flexible sheet 2 with the contact pad 604*a*, it is necessary for the pushing spring 604*a* of the heat transfer block on the side of the flexible sheet 2 to be a spring of a low load. Preferably, a spring of a constant load is used as the pushing spring 604*a* noted above. It should also be noted that the requirements of the heat transfer to the flexible sheet 2 and the thermal expansion can be satisfied simultaneously as far as the contact pad 604*a* and the flexible sheet 2 are positioned close to each other even if the contact pad 604*a* and the flexible sheet 2 are not in mutual contact entirely or partially.

As described above, the flexibility of the flexible sheet 2 performs the three functions given below simultaneously:

a. The flexible sheet 2 is deformed toward the inner region of the channel so as to apply pressure to the fluid inside the channel. As a result, the fluid inside the channel is transferred to the adjacent fluid holding channel 111*b* via the joining channel 117.

b. The flexible sheet 2 is deformed toward the outside of the channel in accordance with the increase in volume of the fluid caused by, for example, the thermal expansion. As a result, the pressure elevation of the fluid inside the channel is moderated so as to prevent the fluid leakage.

c. The flexible sheet 2 is kept in good contact with or is positioned very close to the contact pad 604*a* even during the thermal expansion stage so as to carry out the heat transmission.

(5)-4 Cooling of Adjacent Fluid Holding Channel:

FIG. 53 shows the contact state of the heat transfer blocks 600*a*, 600*b*, 610*a* and 610*b* with the nucleic acid detecting cassette 100. As shown in FIG. 53, the heat transfer blocks 600*a* and 600*b* are arranged to conform with the position of the fluid holding channel 811*a* serving to amplify nucleic acid. For example, where the amplification of nucleic acid is performed by the PCR method, the temperature of the fluid holding channel 811*a* is elevated to about 98° C. Also, in the case of the LAMP method utilizing the isothermal amplification reaction, the temperature of the fluid holding channel 811*a* is maintained at 60 to 65° C. In this stage, a reagent containing an enzyme is already loaded in the adjacent fluid holding channel 811*b*. Since the function of the enzyme loaded in the fluid holding channel 811*b* begins to be deteriorated under temperature not lower than 50° C., it is necessary to prevent the temperature of the fluid holding channel 811*b* from being elevated to 50° C. or more by the conduction of heat from the fluid holding channel 811*a* in which the amplification of nucleic acid is being carried out. Such being the situation, the heat transfer units 610*a* and 610*b* arranged in contact with the adjacent fluid holding channel 811*b* also act as cooling units for cooling the adjacent fluid holding channel 811*b*.

(5)-5 Series-Connected Channels:

Also, the reagent inside the fluid holding channel 811*c*, particularly, the nucleic acid probe inside the detecting channel 531, is weak against heat. Therefore, it is necessary to cool not only the adjacent fluid holding channel 811*b* but also the fluid holding channel 811*c* and the detecting channel 531 when the amplification of nucleic acid is being carried out. As shown in FIG. 53, the fluid holding channels such as the various fluid holding channels 111 and the retreating channel 131 are connected in series in the nucleic acid detecting cassette 100. Such being the situation, it is possible for the heat transfer from the fluid holding channel that is being heated to be absorbed by the adjacent fluid holding channel. As a result, it is possible to suppress the temperature elevation of the fluid holding channels downstream of the adjacent fluid holding channel.

(5)-6 Effect of Heat Transfer Unit:

Prominent effects can be produced by the combination of the heat transfer units 600, 610 with the nucleic acid detecting cassette 100 having a variable-volume channel structure as summarized in the following:

a. Since the channels are arranged in series, the temperature elevation of the unused reagent can be suppressed by simply cooling the adjacent fluid holding channel.

b. Since the pushing block used in a variable-volume channel is movable, it is possible to set the pushing block under the completely opened state. As a result, it is possible to achieve the thermal transfer from both sides of the fluid holding channel so as to suppress the heat loss.

Figure 57:
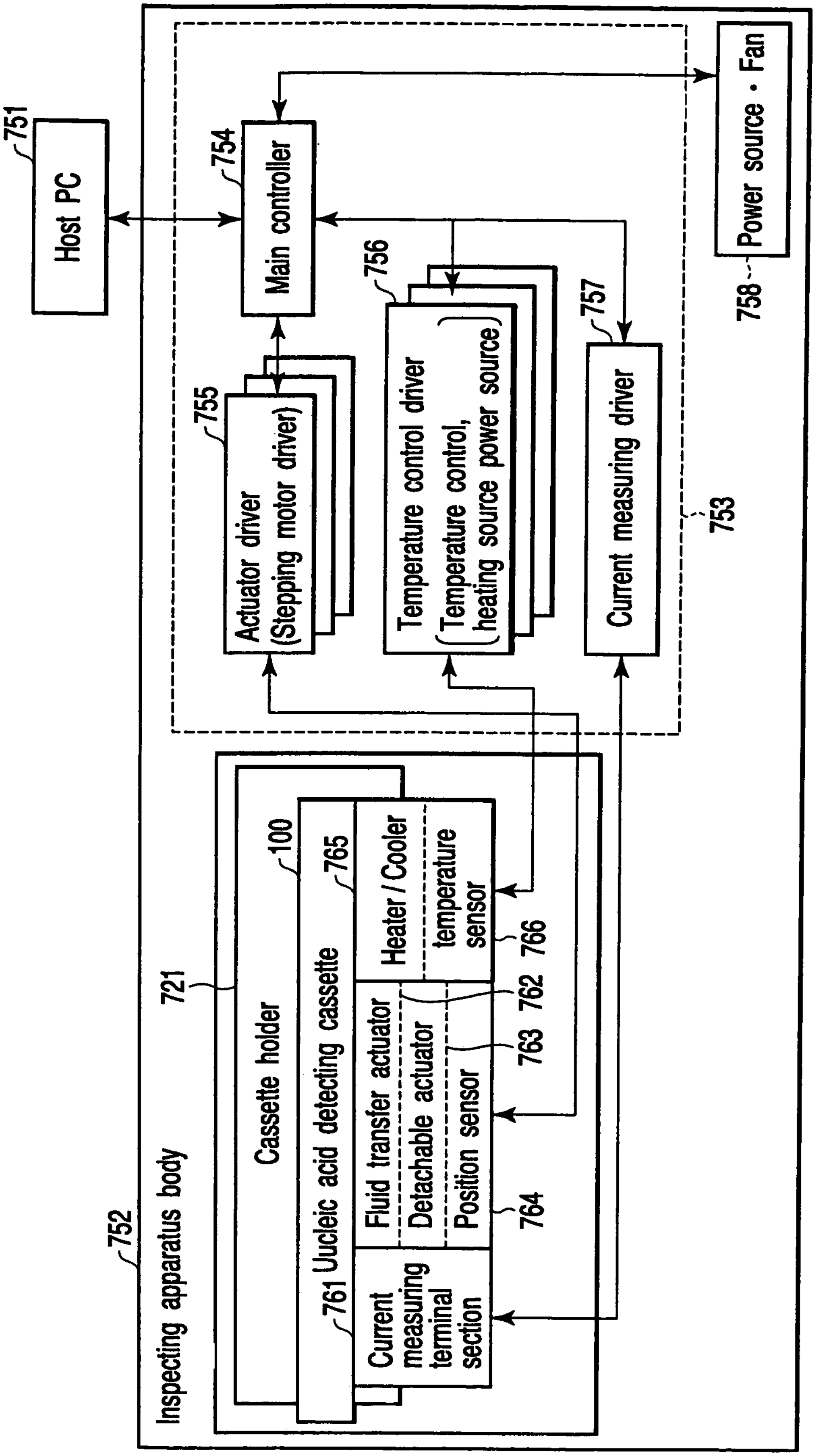
FIG. 57 is a block diagram showing the construction of the nucleic acid detecting system utilizing the nucleic acid detecting cassette shown in FIG. 2.

(6) Entire Structure of Automatic Control Apparatus:

(6)-1 Automatically Controlling Constituent:

(6)-1-1 Block Diagram:

FIG. 57 is a block diagram showing the construction of the nucleic acid detecting system including the construction for automatically controlling each constituent of the nucleic acid detecting system. As shown in FIG. 57, it is possible to perform the nucleic acid detection automatically by applying various operations to the nucleic acid detecting cassette 100 based on the instruction given from a host personal computer 751. A control section 753 generating a control signal based on the instruction given from the host personal computer 751 for controlling the various constituents of the nucleic acid detecting system is mounted in an inspecting apparatus body 752. The control section 753 comprises a main controller 754, an actuator driver 755 that is operated on the basis of the instruction given from the main controller 754, a temperature control driver 756, and a current measuring driver 757. The main controller 754 is connected with a power source•fan 758 mounted outside the control section 753.

(6)-1-2 Motion Control:

The actuator driver 755 is formed of, for example, a stepping motor driver. The actuator driver 755 serves to drive a fluid transferring actuator 762 and a detachable actuator 763 based on the position of the nucleic acid detecting cassette 100 detected by a position sensor 764 so as to transfer the fluid or perform the attaching-detaching operation. The position sensor 764, which is not particularly shown in the drawings showing the construction of the system, is arranged in the vicinity of the moving positions of driving units 701 and 702, which are described herein later, of the nucleic acid detecting cassette 100. The fluid transferring actuator 762 and the detachable actuator 763 are realized by the driving units 701 and 702 in this embodiment of the present invention.

(6)-1-3 Temperature Control:

The temperature control driver 756 serves to control a heater/cooler 765 based on the temperature detected by the temperature sensor 766 so as to control the temperature. The heater/cooler 765 is realized by the heat transfer units 600 and 610 in this embodiment of the present invention.

(6)-1-4 Current Measuring Control:

The current measuring driver 757 takes out a current signal via an electric connector 703 connected to the nucleic acid detecting cassette 100 that is supported by a cassette holder 721 so as to gain the current signal via a current measuring terminal section 761.

Figure 58:
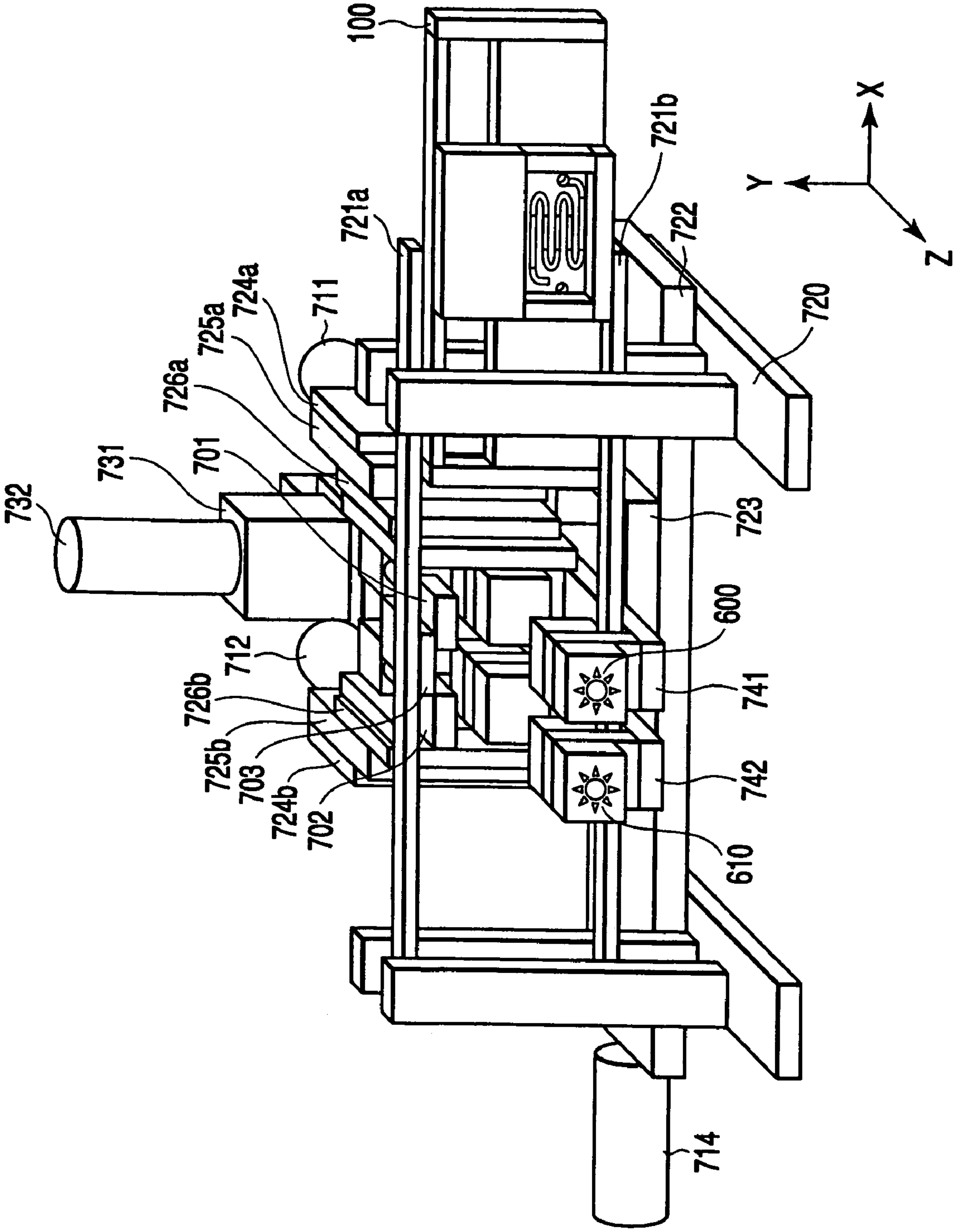
FIG. 58 is an oblique view exemplifying the construction of the automatic control mechanism of the nucleic acid detecting system shown in FIG. 57.
Figure 59:
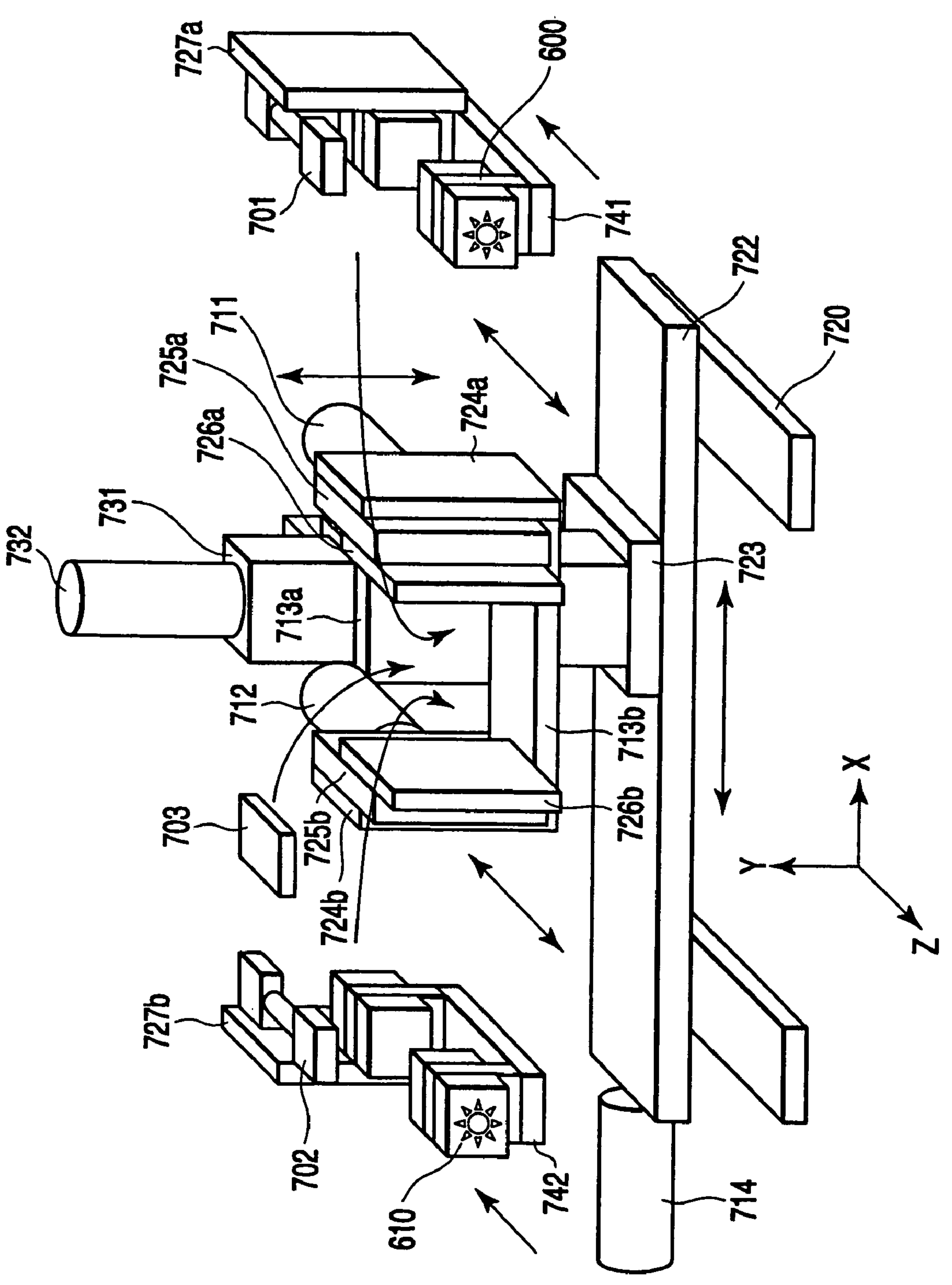
FIG. 59 is an oblique view showing in a dismantled fashion the construction of each of the constituents of the automatic control mechanism shown in FIG. 58.

(6)-2 Motion Control Mechanism:

Each of FIGS. 58 and 59 exemplifies the construction of an automatic control mechanism for automatically executing each of the reactions described above. To be more specific, FIG. 58 is an oblique view showing the construction of the automatic control mechanism during use of the mechanism. On the other hand, FIG. 59 is an oblique view showing in a dismantled fashion the construction of each of the constituting parts of the automatic control mechanism for the sake of convenience in the description.

(6)-2-1 X-Direction Motion Control:

As shown in FIG. 58, a cassette holder 721 and a stationary X-stage 722 are arranged in a fixed fashion on a support table 720. The cassette holder 721 includes rails 721*a* and 721*b* serving to hold the two sides of the nucleic acid detecting cassette 100 so as to guide the nucleic acid detecting cassette 100 in the direction of the X-axis so as to reach the operating section. A movable X-stage 723 is disposed on the stationary X-stage 722. The position of the movable X-stage 723 can be determined in the X-direction on the stationary X-stage 722 by an X-driving device 714.

Arranged in the operating section are an electric connector 703, two driving units 701, 702, and the two heat transfer units 600, 610 as objects to be driven. The operating section can be moved freely in the X-, Y- and Z-directions by the driving system in the X-direction referred to above and by the driving systems in the Y- and Z-directions.

(6)-2-2 Y-Direction Motion Control:

The driving system in the Y-direction comprises a stationary Y-stage 731, a movable Y-stage 713*a* that can be moved in the Y-direction relative to the stationary Y-stage 731 by a Y-driving device 732 so as to have the position determined in the Y-direction, and a movable mounting plate 713*b* that is moved together with the movable Y-stage 713*a*. The stationary Y-stage 731 is fixed to the movable X-stage 723. It follows that the stationary Y-stage 731 can be moved in the X-direction together with the movement of the movable X-stage 723 in the X-direction.

(6)-2-3 Z-Direction Motion Control:

A first driving system in the Z-direction comprises a stationary Z-stage 725*a* and a movable Z-stage 726*a* that can be driven by a first Z-driving device 711 such that the position of the movable Z-stage 726*a* can be determined in the Z-direction relative to the stationary Z-stage 725*a*. The stationary Z-stage 725*a* is fixed to a first Z-stage mounting plate 724*a* that is fixed to a movable mounting plate 713*b*. As a result, the stationary Z-stage 725*a* can also be moved in the X- and Y-directions together with the movement of the first Z-stage mounting plate 724*a* in the X- and Y-directions.

A second driving system in the Z-direction comprises a stationary Z-stage 725*b* and a movable Z-stage 726*b* that can be driven by a second Z-driving device 712 such that the position of the movable Z-stage 726*b* can be determined in the Z-direction relative to the stationary Z-stage 725*b*. The stationary Z-stage 725*b* is fixed to a second Z-stage mounting plate 724*b* that is fixed to a movable mounting plate 713*b*. As a result, the stationary Z-stage 725*b* can also be moved in the X- and Y-directions in accordance with the movement of the second Z-stage mounting plate 724*b* in the X- and Y-directions.

(6)-2-4 Related Motion Control:

The driving units 701 and 702 are fixed to the movable Z-stages 726*a* and 726*b* via the mounting plates 727*a* and 727*b*, respectively. As a result, the driving units 701 and 702 can be moved freely in the X-, Y- and Z-directions in accordance with the movement of the movable Z-stages 726*a* and 726*b* in the X-, Y- and Z-directions.

Also, the heat transfer units 600 and 610 are fixed to the movable Z-stages 726*a* and 726*b* via the mounting tables 741 and 742 and, further, via the mounting plates 727*a* and 727*b* such that the heat transfer units 600 and 610 are selectively movable. Similarly, the electric connector 703 is also fixed to the movable Z-stages 726*a* or 726*b* such that the electric connector 703 is positioned in the vicinity of the region right above the driving units 701 and 702 and is selectively movable. As a result, the heat transfer units 600, 610 and the electric connector 703 can also be moved freely in the X-, Y- and Z-directions together with the movement of the movable Z-stages 726*a* and 726*b* in the X-, Y- and Z-directions. It should be noted, however, that the heat transfer units 600, 610 and the electric connector 703 can be moved selectively in the Z-direction so as to make it possible to bring individually the heat transfer units 600, 610 and the electric connector 703 to positions in the vicinity of the nucleic acid detecting cassette 100 or into contact with the nucleic acid detecting cassette 100.

Two driving units 701 and 702 are arranged in the present invention and these two driving units can be driven individually. As a result, it is possible to realize the fluid transfer operation by allowing one of these driving units to perform the operation of pressurizing the pad and the other driving unit so as to release the pressurization. For example, it is possible to circulate the reagent within the fluid holding channel by pushing the center of the channel by using the driving unit 701 and by releasing the pressurization on the left side of the fluid holding channel by using the driving unit 702.

Similarly, the two heat transfer units 600 and 610 are arranged in the present invention, and the temperature of these two heat transfer units can be individually controlled. As a result, it is possible to perform a unique control such that, for example, the heating is performed in one channel and the cooling is performed in the other channel.

(6)-3 Effect of Nucleic Acid Detecting System:

As described above, according to the nucleic acid detecting cassette 100 according to the first embodiment of the present invention and the nucleic acid detecting system equipped with the nucleic acid detecting cassette 100 as well as with the driving system and the control system for automatically controlling the nucleic acid detecting cassette 100, it is possible to automatically carry out continuously the series of operations including the amplification of nucleic acid and the other required processing and the detection of the target nucleic acid within a closed system.

(7) Modifications of First Embodiment:

Incidentally, the present invention is not limited to the first embodiment described above.

Specifically, the materials of the stationary base plate 1, the flexible sheet 2 and the cover plate 3 are not limited to those described previously.

Also, the present invention is not limited to the constructions of the blocks 101, 102, 103 and 106 shown in FIG. 1. It is also possible to arrange different kinds of blocks depending on the types of the required reactions. For example, it is possible to omit the intermediate section block 101 so as to allow the nucleic acid detecting cassette to be formed of the edge side block 102, the detecting section block 106 and the edge side block 103 alone. Alternatively, it is also possible to increase the number of intermediate section blocks 101 arranged in the nucleic acid detecting cassette 100 shown in FIG. 1.

The shape of the pad pushing each of the flexible sheets 2 is not limited to that in the first embodiment described above. In this embodiment, the pad of the fluid holding channel 111 or the retreating channel 131 consists of three pads. However, it is possible for the pad noted above to consist of at most two pads or at least four pads.

Also, in the first embodiment of the present invention, the opening-closing of each of the channels is controlled by using two driving units 701 and 702. However, it is also possible to use three or more driving units. Similarly, it is also possible to use many other heat transfer units in addition to the heat transfer units 600 and 610.

Second Embodiment

A second embodiment of the present invention, which corresponds to a modification of the first embodiment described with reference to FIGS. 1 to 59, will now be described. The second embodiment corresponds to modifications in the cassette structure and in the channel pattern. It should be noted that the construction or structure similar to that in the first embodiment is applied in the second embodiment of the present invention.

(1) Modification in Cassette Structure:

FIGS. 60 to 64 are cross sectional views showing the cassette structures relating to modifications employed in the second embodiment of the present invention. The cross sections shown in these drawings correspond to the cross section denoted by a broken line F in FIG. 41.

Figure 60:
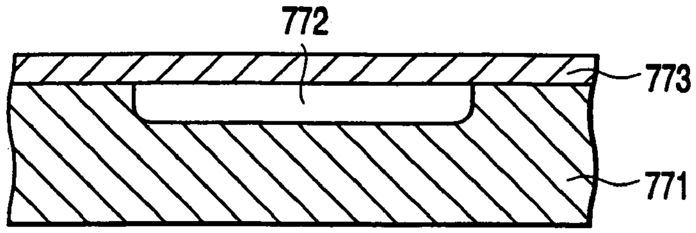
FIG. 60 is a cross sectional view schematically showing the construction of the nucleic acid detecting cassette according to a second embodiment of the present invention.

(1)-1 Channel Formed in Stationary Plate:

FIG. 60 shows an example in which a channel is formed in the stationary base plate. As apparent from the comparison with FIG. 41, the construction shown in FIG. 60 resembles the example of the construction shown in FIG. 41. In the construction shown in FIG. 60, a channel 772 is formed in a stationary base plate 771, and a flexible sheet 773 is bonded to the stationary base plate 771. In other words, a channel is formed on the side of the stationary base plate 771, and the channel thus formed is allowed to act as the channel 772.

Figure 61:
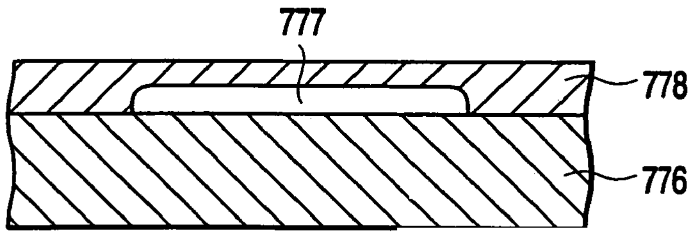
FIG. 61 is a cross sectional view schematically showing the construction of the nucleic acid detecting cassette shown in FIG. 60.

(1)-2 Channel Formed in Flexible Sheet:

FIG. 61 shows an example of the construction in which a channel is formed in the flexible sheet. As shown in FIG. 61, a stationary base plate 776 is formed of a flat plate in which a channel is not formed, and a flexible sheet 778 having a channel 777 formed therein is bonded to the stationary base plate 777. In other words, the channel is formed on the side of the flexible sheet 778, and the channel thus formed is allowed to act as the channel 777.

Figure 62:
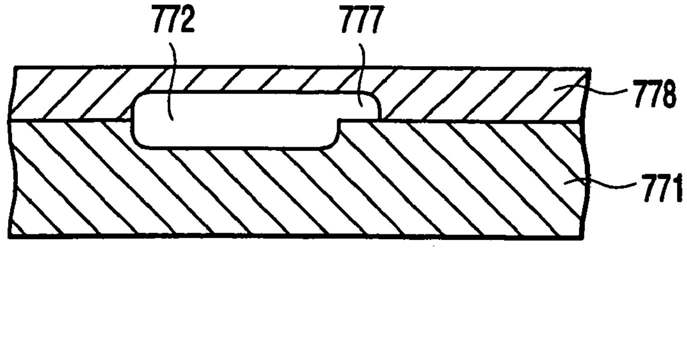
FIG. 62 is a cross sectional view schematically showing the construction of the nucleic acid detecting cassette shown in FIG. 60.

(1)-3 Channel Formed in Each of Stationary Plate and Flexible Sheet:

FIG. 62 shows an example of the construction in which a channel is formed in each of the stationary base plate and the flexible sheet. As shown in FIG. 62, a channel 772 is formed in a stationary base plate 771. Also, a flexible sheet 778 having a channel 777 formed therein is bonded to the stationary base plate 771 having the channel 772 formed therein.

(1)-4 Channel Formed by Expansion of Flexible Sheet

Figure 63:
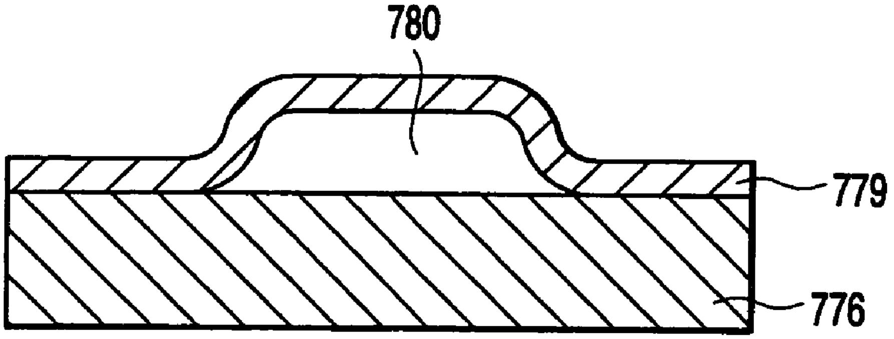
FIG. 63 is a cross sectional view schematically showing the construction of the nucleic acid detecting cassette shown in FIG. 60.

FIG. 63 shows an example of construction in which a channel is formed by the expansion of the flexible sheet stemming from the pressure increase of the fluid inside the channel. As shown in FIG. 63, a flexible sheet 779, which is expanded, is bonded to a stationary base plate 776 such that a space 780 is formed between the flexible sheet 779 and the stationary base plate 776. The space 780 thus formed performs the function of a channel. The state that the space 780 is formed denotes that the channel is opened. The channel thus formed can be closed by pushing the flexible sheet 779 against the stationary base plate 776 by using a cover expansion regulating member (not shown).

(1)-5 Coated Channel

Figure 64:
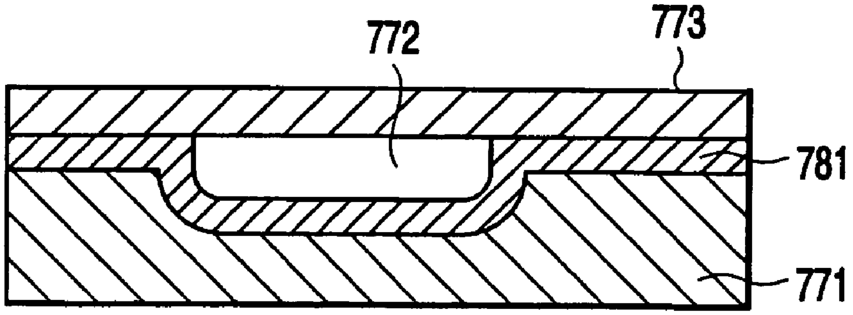
FIG. 64 is a cross sectional view schematically showing the construction of the nucleic acid detecting cassette shown in FIG. 60.

Further, FIG. 64 shows an example of construction in which a channel is formed in the stationary base plate. In this example, a coating is applied to the surface of the stationary base plate. As shown in the drawing, a coating member 781 is bonded in a manner to cover the surface of a stationary base plate 771 having a channel 772 formed therein. A flexible sheet 773 disposed on the stationary base plate 771 is bonded to the stationary base plate 771 with the coating member 781 interposed therebetween.

Incidentally, the examples shown in FIGS. 60 to 64 are no more than some of the examples that can be employed in the present invention. Also, it is possible to combine some of these examples within a single nucleic acid detecting cassette in accordance with the function of each of these examples.

Figure 65A:
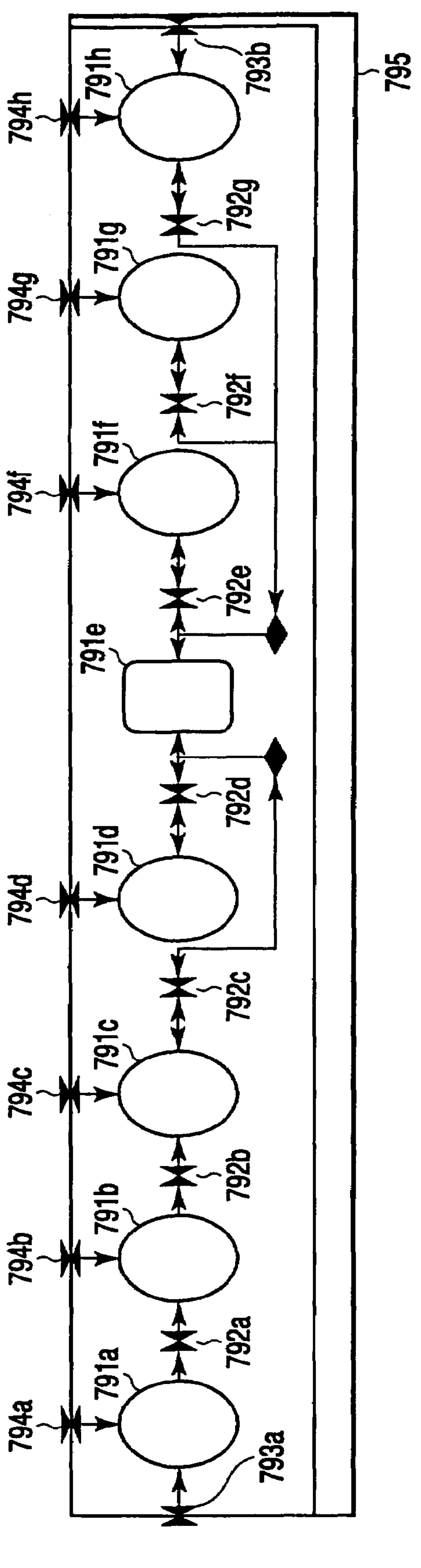
FIGS. 65A and 65B schematically show the construction of the nucleic acid detecting cassette in which the retreating channel and the detecting channel shown in FIGS. 42 to 52 are modified.
Figure 65B:
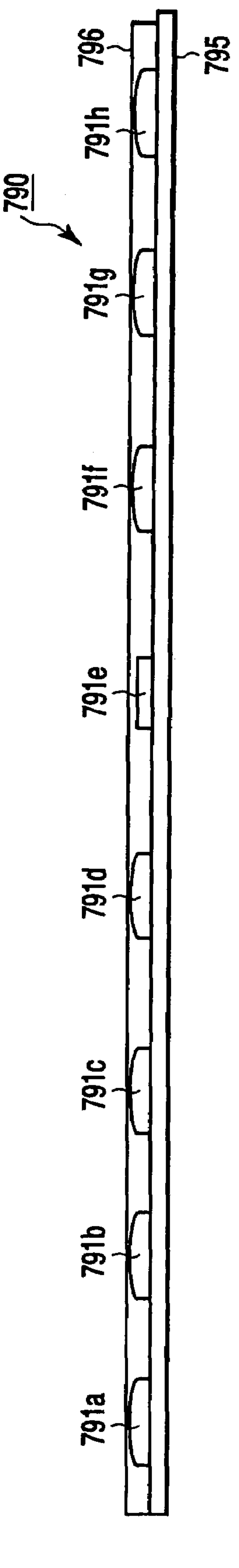

(2) Modifications of Channel Pattern:

(2)-1 One-Layer Structure Channel:

(2)-1-1 Structure of Each Channel:

FIGS. 65A and 65B schematically show the constructions of nucleic acid detecting cassettes 790, which are directed to a modification of the retreating channel and to a modification of the detecting channel, respectively. Specifically, FIG. 65A corresponds to the schematic drawings of FIGS. 42 to 52, and FIG. 65B is a cross sectional view in the vicinity of the fluid holding channel.

As shown in FIG. 65A, arranged are fluid holding channels 791*a*, 791*b*, 791*c*, a retreating channels 791*d*, a detecting channel 791*e*, and fluid holding channels 791*g* and 791*h* in the order mentioned as viewed from the left side in the drawing.

The fluid holding channel 791*a* is used as a reaction chamber for performing an amplification reaction of nucleic acid. The fluid holding channels 791*a* and 791*b* are joined to each other by a joining channel having the joining valve 792*a* mounted thereto. It is possible to inject a reagent and a sample into the fluid holding channel 791*a* via two valves 793*a* and 794*a*.

The fluid holding channel 791*b* is used as a reaction chamber for carrying out a reaction for the producing a single stranded nucleic acid. The fluid holding channels 791*b* and 791*c* are joined to each other by a joining channel having a joining valve 792*b* mounted thereto. It is possible to inject a reagent into the fluid holding channel 791*b* via a valve 794*b*.

The fluid holding channel 791*c* is used as a reaction chamber for carrying out a reaction for imparting a protective chain. The fluid holding channels 791*c* is joined to a detecting channel 791*e* by a joining channel having the joining valve 792*c* mounted thereto. It is possible to inject a reagent into the fluid holding channel 791*c* via a valve 794*c*.

The retreating channel 791*d* is used as a retreating channel of the detecting channel 791*e*. The retreating channel 791*d* is connected to the detecting channel 791*d* by a joining valve 792*d*. It is possible to inject a fluid into the retreating channel 791*d* via a valve 794*d*.

The detecting channel 791*e* is used as a reaction chamber for carrying out a reaction such as a hybridization reaction or for the detection. The fluid transferred in the detecting channel 791*e* is purged into the fluid holding channel 791*g* with gaseous material loaded in the retreating channel 791*d*. The fluid transferred in the detecting channel 791*e* is also purged into the fluid holding channel 791*c* with gaseous material loaded in the retreating channel 791*f*.

The retreating channel 791*f* is used as a retreating channel of the detecting channel 791*e*. The retreating channel 791*f* is joined to the detection channel 791*e* by a joining valve 792*e*. It is possible to inject a fluid into the retreating channel 791*f* via the valve 794*f*.

The fluid holding channel 791*g* is used as a chamber for holding a washing solution used for performing the washing treatment within the detecting channel 791*e* after the hybridization reaction. The fluid holding channel 791*g* is joined to the detecting channel 791*e* by a joining valve 792*f*. It is possible to inject a reagent into the fluid holding channel 791*g* via a valve 794*g*.

The fluid holding channel 791*h* is used as a chamber for holding a solution of an intercalating agent used for imparting the intercalating agent within the detecting channel 791*e* after the hybridization reaction and the washing treatment. The fluid holding channel 791*h* is joined to the detecting channel 791*e* by a joining channel having a joining valve 792*g* mounted thereto. It is possible to inject a reagent into the fluid holding channel 791*h* via a valve 794*h* or a valve 793*b*.

(2)-1-2 Effect of One-Layer Structure:

As shown in FIG. 65B, the channels 791*a* to 791*h* are formed on a single plane by the channels formed in the flexible sheet 796 positioned on the stationary base plate 795 and, thus, the second embodiment differs in this respect from the first embodiment in which the detecting channel and the retreating channel are formed to have a two-layer structure consisting of an upper layer and a lower layer. Therefore, the thickness of the cassette structure can be decreased in the case of forming the channels in a manner to form a planar arrangement. Incidentally, in the example shown in FIG. 65B, two retreating channels are formed. However, it is possible to omit one of these retreating channels so as to have the other retreating channel alone included in the cassette structure.

Also, it is possible to modify the channel pattern in various fashions in addition to the construction shown in FIGS. 65A and 65B. For example, in the embodiment described above, the standard inner volume of the reaction chamber is set at 48 μl in each of the fluid holding channels, the retreating channels, and the detecting channels. However, it is possible to decrease the standard inner volume noted above so as to miniaturize the cassette structure.

Also, in the case of using a single flexible sheet 796 for forming each of the fluid holding channels 791*a*, etc. and the detecting channel 791*e* as in the example shown in FIGS. 65A and 65B, it is possible for the flexible sheet 796 to be also used as a flexible member.

In the example according to the first embodiment of the present invention, the nucleic acid detecting chip 500 is immobilized on the glass base plate 500*a*. However, the present invention is not limited to the particular construction. For example, the nucleic acid detecting chip 500 can be made integral by forming the electrodes such as the nucleic acid immobilizing electrode 501, the counter electrode 503 and the reference electrode 504 on the stationary base plate 1. In the case of using the stationary base plate 795 shown in FIGS. 65A and 65B, it is possible to form the nucleic acid immobilizing electrode 501, the counter electrode 503 and the reference electrode 504 on the stationary base plate 795.

It should also be noted that, in the example according to the first embodiment of the present invention, the nucleic acid detecting chip 500 is fixed to the stationary base plate 1. However, the present invention is not limited to the particular construction. In the case of using, for example, a glass base plate as the stationary base plate 1, it is possible to make the nucleic acid detecting chip 500 integral by forming the nucleic acid immobilizing electrode 501, the counter electrode 503 and the reference electrode 504 on the glass base plate.

Figure 66:
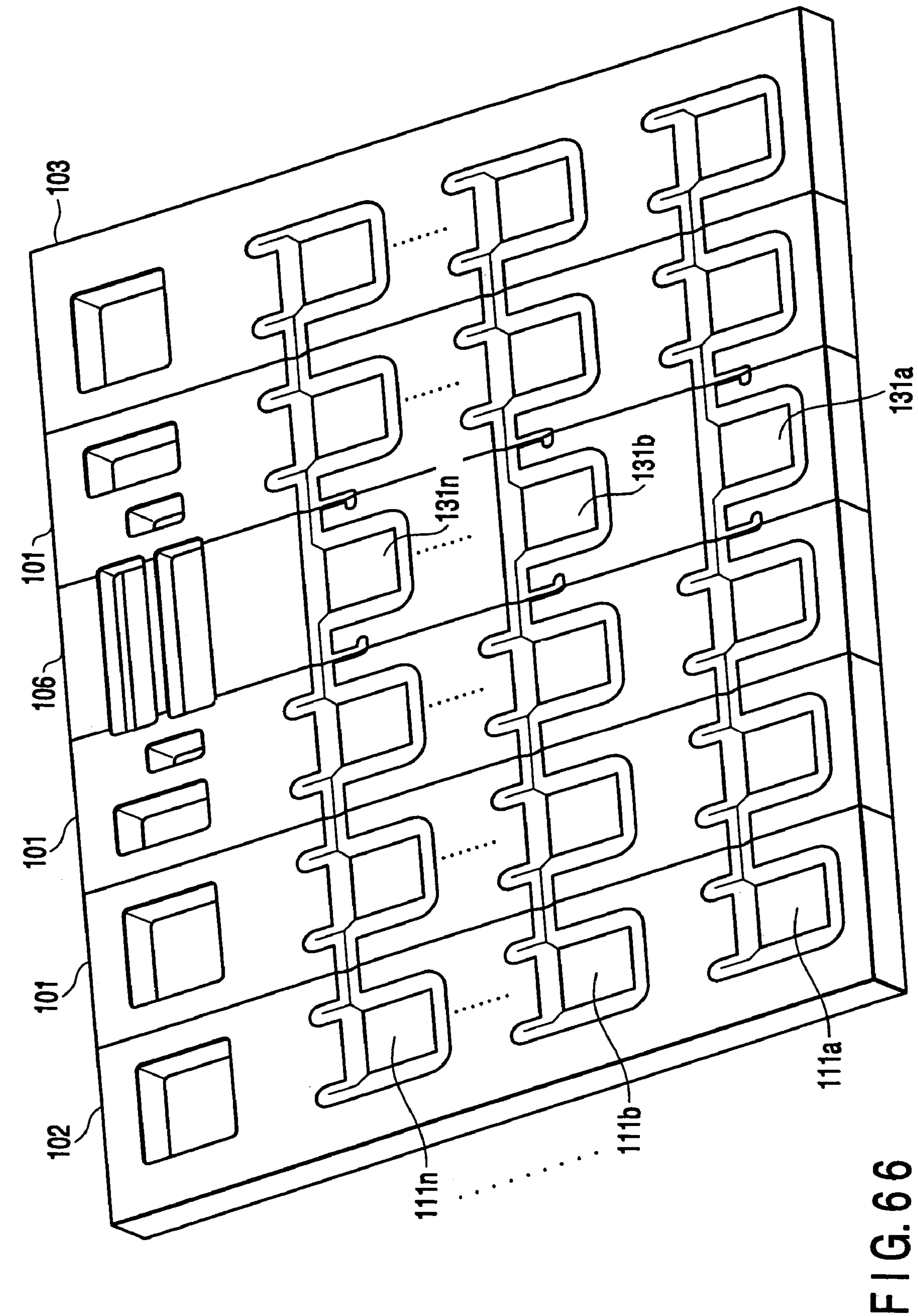
FIG. 66 is an oblique view schematically showing as an example the construction of the multiplex nucleic acid detecting cassette included in the nucleic acid detecting cassette shown in FIG. 77.

(2)-2 Multiplex Detecting Apparatus:

Also, in the example according to the first embodiment of the present invention, the fluid holding channel and the retreating channel are arranged on a single line. However, it is also possible to arrange the fluid holding channels and the retreating channels on a plurality of straight lines so as to obtain a multiplex detecting apparatus. FIG. 66 is an oblique view schematically showing as an example the construction of the multiplex nucleic acid detecting cassette 797, which corresponds to the construction shown in FIG. 4 in conjunction with the first embodiment of the present invention. As shown in FIG. 66, an n-number of fluid holding channels 111*a*, 111*b*, . . . , 111*n*, which are equal to each other in construction, are formed in the edge section block 102. Also, an n-number of fluid holding channels each having the same construction are formed in each of the two intermediate section blocks 101. Further, an n-number of retreating channels each having the same construction are formed in the detecting section block 106 that is positioned adjacent to the left-side intermediate section block 101. Further, an n-number of the same fluid holding channels are formed in the intermediate section block 101 adjacent to the detecting section block 106 on the left side. Still further, an n-number of fluid holding channels, which are equal to each other in the construction, are formed in the edge section block 103. Incidentally, the n-number of the fluid holding channels are equal to each other in respect of the construction of the peripheral portion (not shown), too. It should be noted that the second embodiment is common with the first embodiment in respect of the construction inside the block, though the construction inside the block is not shown in detail in conjunction with the second embodiment of the present invention. In the case of employing the multiplex system involving the n-number of channels, it is possible to obtain various merits. For example, it is possible to carry out a plurality of reactions and the detection simultaneously. Also, a plurality of different kinds of target nucleic acid can be detected simultaneously. Further, a plurality of samples can be detected simultaneously. Still further, the detected data can be made uniform. Incidentally, in the example shown in FIG. 66, a single contact point opening 151 is formed for the n-number of retreating channels 131, i.e., the n-number of detecting channels 531. However, it is also possible to arrange the contact point opening 151 for each of the n-number of retreating channels 131, i.e., the n-number of detecting channels 531.

(3) Effect and Modifications of Second Embodiment:

Further, as another channel pattern, the continuous channels can be formed by increasing or decreasing the number of reaction chambers. For example, in the construction exemplified in FIGS. 65A and 65B, six fluid holding channels including the retreating channels are arranged consecutively. In the example of the construction shown in FIGS. 65A and 65B, seven fluid holding channels including the retreating channels and one detecting channel are arranged consecutively. Needless to say, however, the number of channels is not limited to that exemplified above.

As described above, according to the second embodiment of the present invention, which is achieved by modifying the construction according to the first embodiment of the present invention, it is possible to provide a nucleic acid detecting closed cassette that can be used for the automatic continuous processing throughout the system including the amplification of nucleic acid and other required processing and the detection of the target nucleic acid as in the first embodiment of the present invention.

Third Embodiment

The third embodiment corresponds to a modification in the shapes of the variable-volume channels such as the fluid holding channel and the retreating channel in each of the first and second embodiments described above. In the first embodiment, the channel is shaped substantially rectangular. However, it is possible to use, for example, a U-shaped variable-volume channel as in the third embodiment of the present invention. The construction substantially equal to that in the first embodiment is employed in the third embodiment unless otherwise specified.

Figure 67:
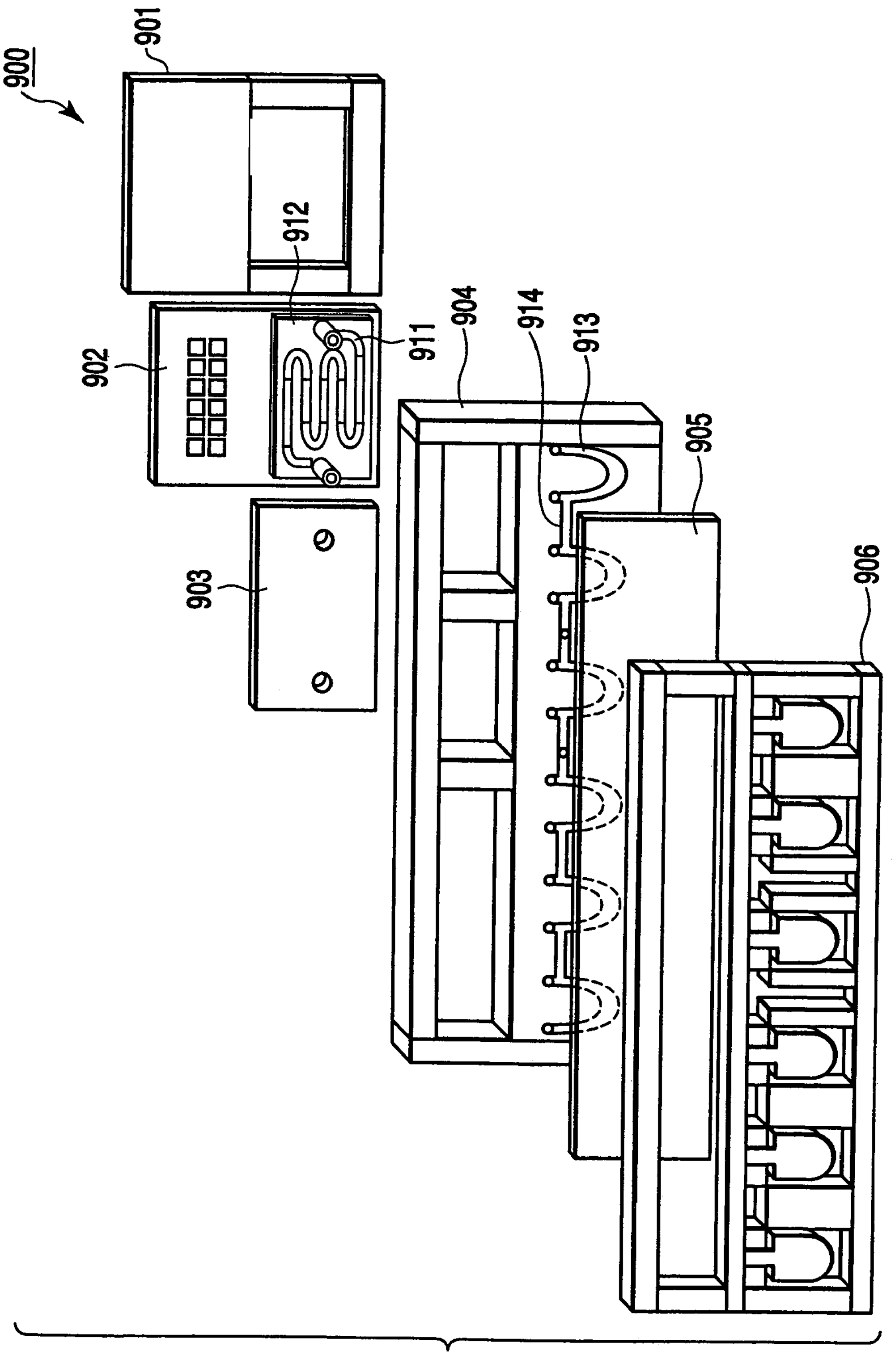
FIG. 67 is an oblique view showing in a dismantled fashion, i.e., the state before the assembly, the construction of the nucleic acid detecting cassette employing a U-shaped variable-volume channel according to modifications of the retreating channel and the detecting channel shown in FIGS. 65A and 65B.
Figure 68:
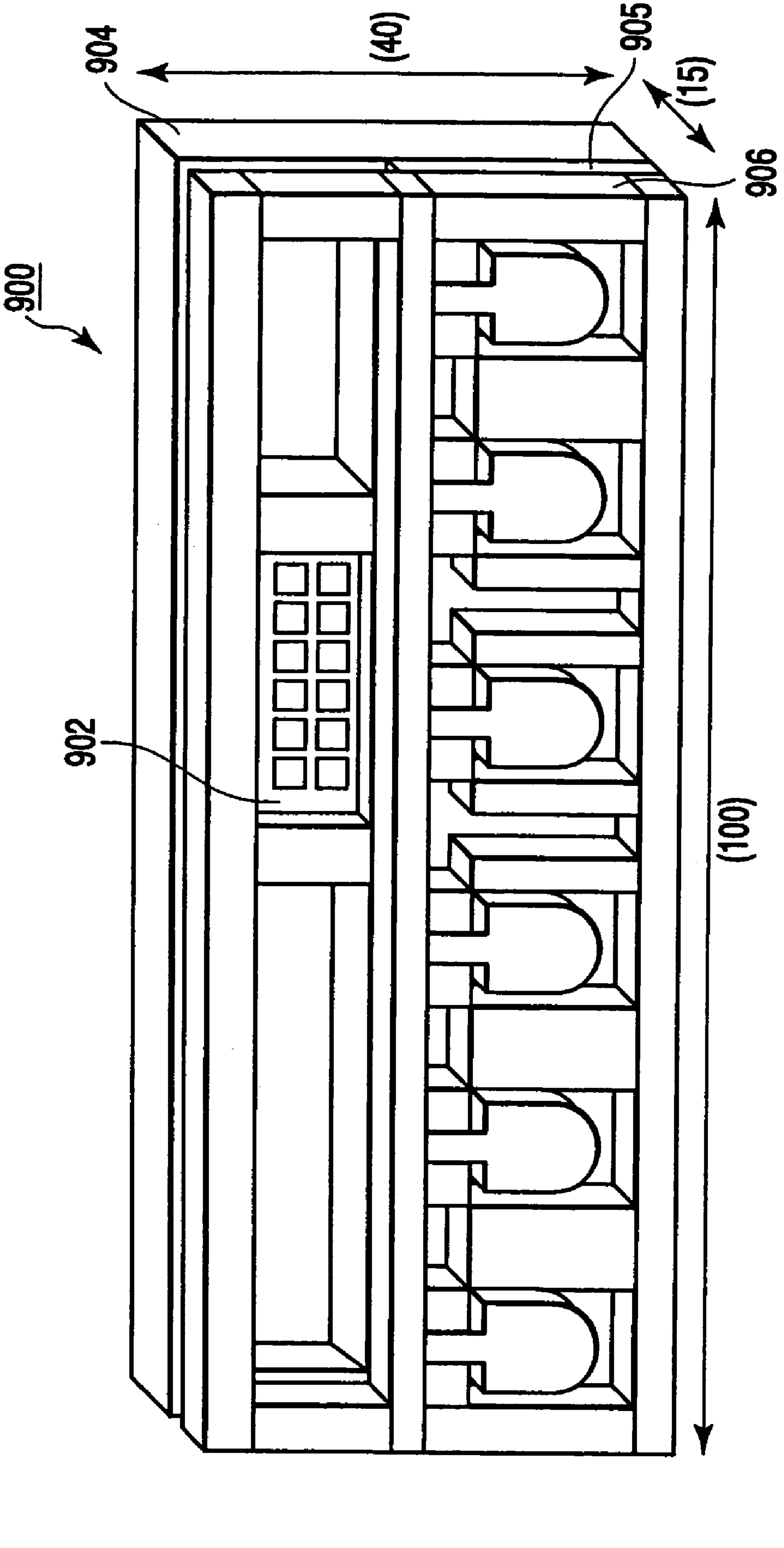
FIG. 68 is an oblique view schematically showing the construction of the nucleic acid detecting cassette after assembly in respect of the nucleic acid detecting cassette employing the U-shaped variable-volume channel shown in FIG. 67.

(1) Basic Construction of Cassette:

FIGS. 67 and 68 exemplify the basic construction of a nucleic acid detecting cassette 900 employing a U-shaped variable-volume channel. Specifically, FIG. 67 is an oblique view showing in a dismantled fashion before the assembly of the nucleic acid detecting cassette 900, and FIG. 68 is an oblique view showing the construction of the assembled nucleic acid detecting cassette 900 that is put to the practical use.

As shown in FIG. 67, the nucleic acid detecting cassette 900 comprises a chip holder 901, a nucleic acid detecting chip 902, a chip cover 903, a channel block 904, a flexible sheet 905, and a seal block 906. An electrode (not shown) is arranged in the nucleic acid detecting chip 902. A channel 911 is formed in a detecting channel seal 912 in a manner to cover the electrode arranged in the nucleic acid detecting chip 902, and the detecting channel seal 912 is bonded to the chip cover 903. After the detecting channel seal 912 is covered with the chip cover 903, the nucleic acid detecting chip 902, the detecting channel seal 912 and the chip cover 903 are fixed by the chip holder 901.

A plurality of U-shaped channels 913 whose inner volumes are variable are formed on the surface of the channel block 904. The adjacent U-shaped channels 913 are joined to each other by a joining valve 914. The fourth U-shaped channel 913 as viewed from the left side in the drawing performs the function of a retreating channel. The chip holder 901 that is made integral with the nucleic acid detecting chip 902 is fixed to the back surface of the fourth U-shaped channel 913 referred to above. Also, all of the U-shaped channels 913 are covered with the flexible sheet 905, and the seal block 906 is bonded to the flexible sheet 905. As a result, formed is the nucleic acid detecting cassette 900 shown in FIG. 68.

Figure 69:
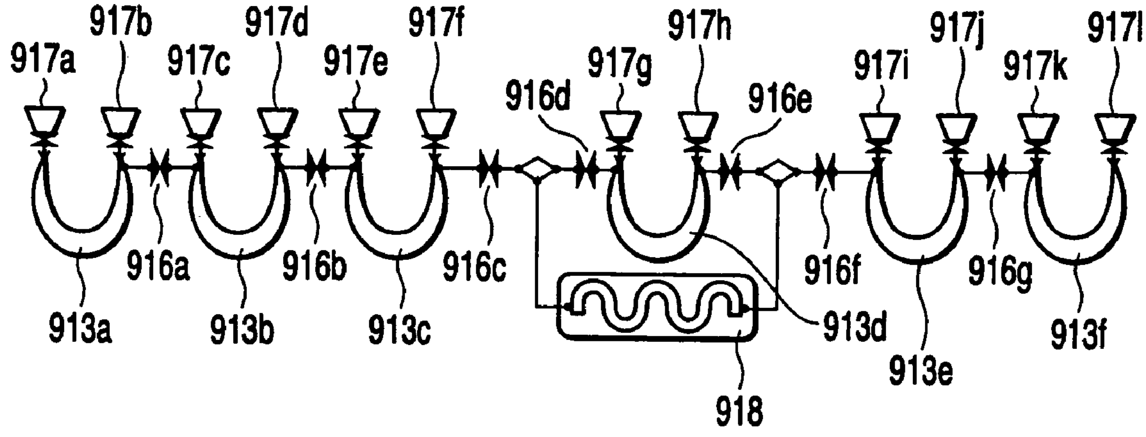
FIG. 69 schematically exemplifies the U-shaped channel system in the manufacturing stage of the nucleic acid detecting cassette shown in FIGS. 65A and 65B.

(2) Channel System of U-Shaped Channel:

(2)-1 Entire Structure of Channel System:

FIG. 69 exemplifies the construction of the U-shaped channel 913 as manufactured. As shown in the drawing, arranged are six U-shaped channels 913*a* to 913*f*. These U-shaped channels 913*a* to 913*f* perform respectively the function of a reaction chamber for amplification of nucleic acid, the function of a reaction chamber for producing a single stranded nucleic acid, the function of a reaction chamber for imparting a protective chain, the function of a retreating channel, the function of a washing solution holding chamber, and the function of an intercalating agent holding chamber. Also, the adjacent U-shaped channels are joined to each other via joining valves 916*a* to 916*g*. Also, self-sealing type ports 917*a* to 9171 are formed in these U-shaped channels 913*a* to 913*f*. It should be noted that two self-sealing type ports are mounted to each of the U-shaped channels. Also, a detecting channel 918 is joined to both edges of the U-shaped channel 913*d* acting as a retreating channel.

Figure 70:
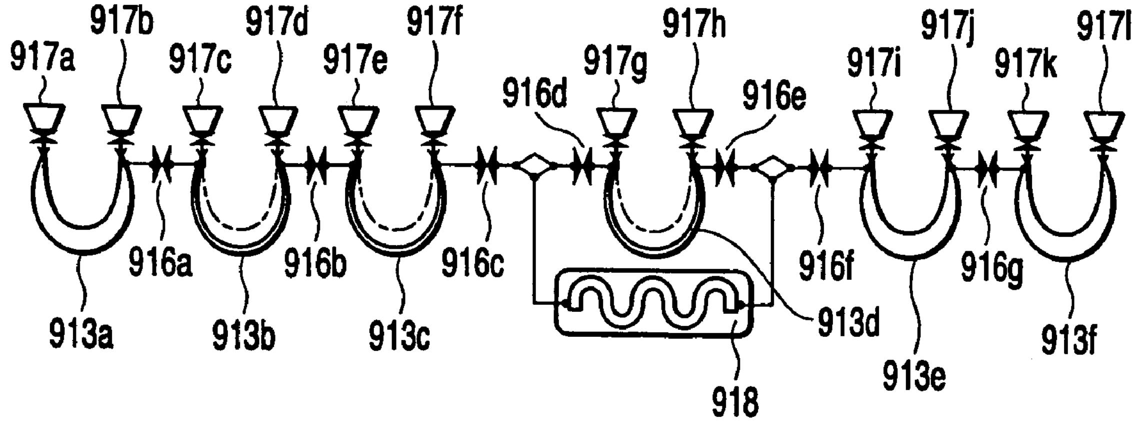
FIG. 70 schematically exemplifies the U-shaped channel system in the shipping stage of the nucleic acid detecting cassette shown in FIGS. 65A and 65B.

FIG. 70 exemplifies the construction in the stage of delivery to the market. All the required reagents are already loaded in the U-shaped channels 913*a* to 913*f*. During the use, the detection can be achieved by an apparatus by simply injecting a sample containing a nucleic acid material.

Figure 71A:
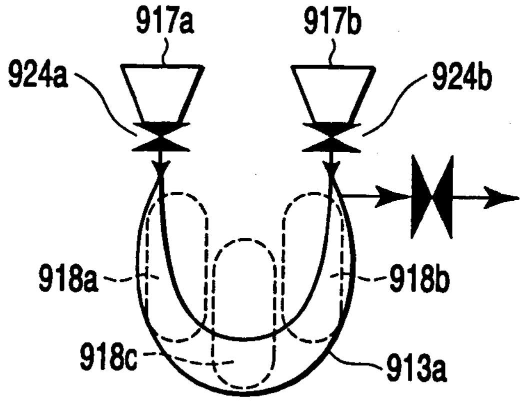
FIGS. 71A and 71B schematically show the basic construction of the U-shaped channel having a variable inner volume, which is shown in FIGS. 65A and 65B.
Figure 71B:
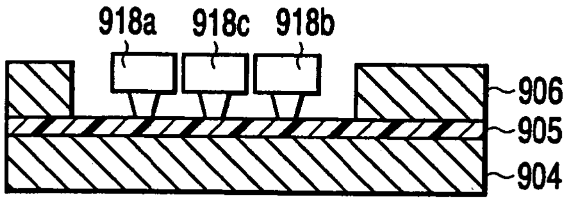
Figure 72A:
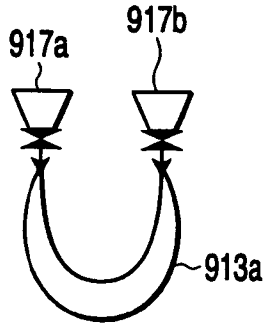
FIGS. 72A to 72C schematically show the opened and closed states of the channel using the compression pressurizing pad shown in FIGS. 71A and 71B.
Figure 72B:
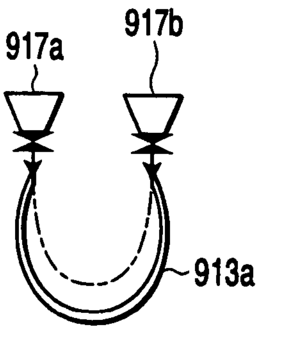
Figure 72C:
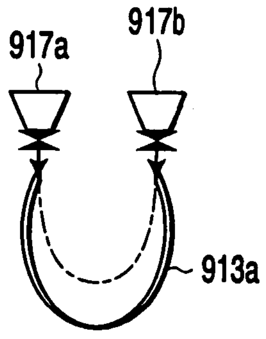

(2)-2 Structure of the U-Shaped Channel:

FIGS. 71A and 71B are for describing the basic structure of the U-shaped channel 913 having a variable inner volume. FIG. 71A is an upper view, and FIG. 71B is a cross sectional view. As shown in the drawings, pushing pads 918*a* to 918*c* for compression are arranged on the right side, on the left side and in the center of the channel. The opening-closing between a self-sealing type port 917*a* and the fluid holding channel 913*a* is controlled by the inlet-outlet valve 924*a*, the opening-closing between a self-sealing type port 917*b* and the fluid holding channel 913*a* is controlled by an inlet-outlet valve 924*b*. The other U-shaped channels have the similar construction. FIGS. 72A, 72B and 72C show the opened-closed state of the channel using the pushing pads 918*a* to 918*c* for compression. To be more specific, FIG. 72A shows the completely opened state of the channel, FIG. 72B shows the half-opened state of the channel, and FIG. 72C shows the completely closed state of the channel.

Figure 73:
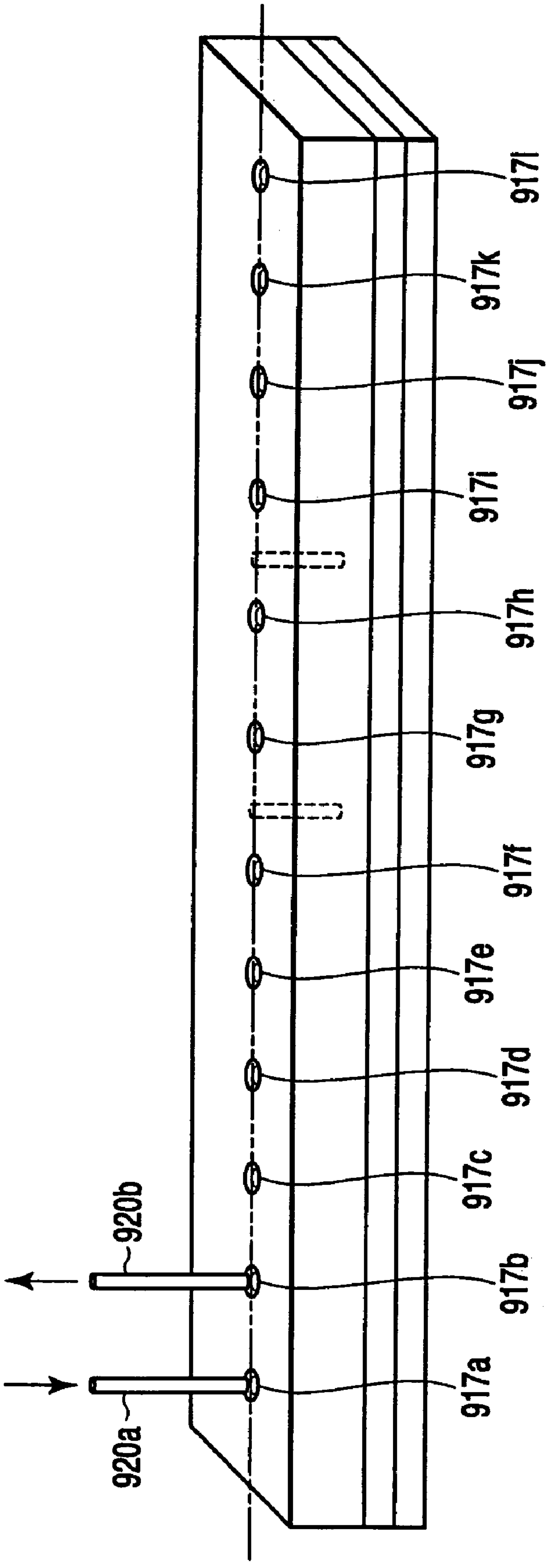
FIG. 73 is an oblique view for explaining the operation for injecting a solution into the nucleic acid detecting cassette using a self-sealing type port shown in FIGS. 71A and 71B.

(2)-3 Self-Sealing Type Port:

FIG. 73 is an oblique view for explaining the fluid injecting operation of the cassette using the self-sealing type ports. A fluid injecting tip 920*a* and a tip 920*b* equipped with a check valve are inserted into the self-sealing type ports 917*a* and 917*b*, respectively. A reagent is injected into the fluid injecting tip 920*a*, and the air is withdrawn from the tip 920*b* equipped with a check valve. Each of the self-sealing type ports 917*a* and 917*b* is formed of a flexible member that can be expanded or shrunk. Under the expanded state in which an external force is not applied, the port is closed so as to interrupt the passage of the gas and the liquid between the inside and the outside of the cassette. If the fluid injecting tip 920*a* and the tip 920*b* equipped with a check valve are inserted into the self-sealing type ports 917*a* and 917*b*, respectively, the flexible member is shrunk in an amount corresponding to the dimension of the tip so as to make it possible to achieve the passage of the gas and the liquid between the inner space of the chip and the channel within the cassette.

Figure 74:
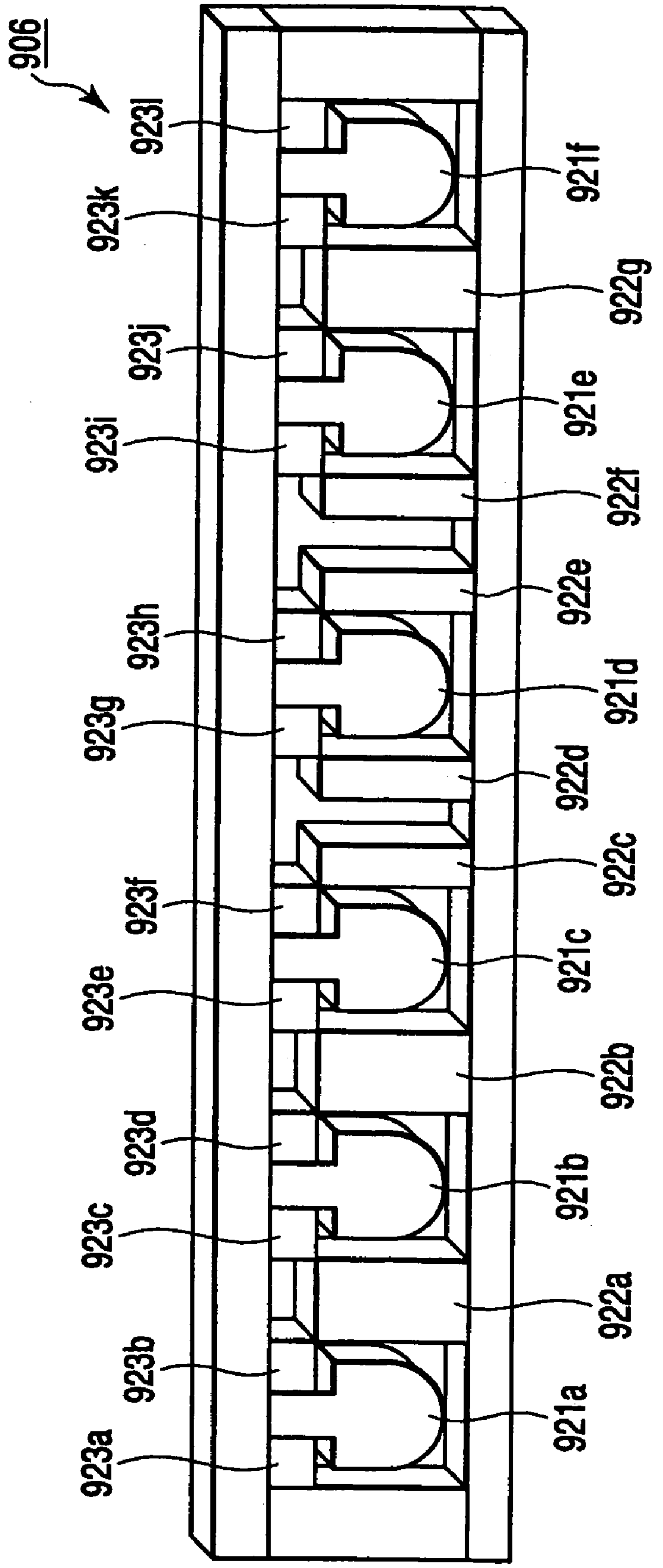
FIG. 74 shows in detail the construction of the channel block shown in FIG. 67.

(2)-4 Seal Block:

FIG. 74 shows the outer appearance of the seal block 906. The channel pressurizing pads 921*a* to 921*f* are pads for pressurizing the channels 913*a* to 913*f*, respectively. To be more specific, each of the pressurizing pads is formed of the three pads 918*a* to 918*c*. Joining pressurizing pads 922*a* to 922*g* are pads for opening-closing the joining channels for joining the channels 913*a* to 913*f* to each other. The joining valves 916*a* to 916*g* are realized by these joining pressurizing pads 922*a* to 922*g*. Further, inlet-outlet pressurizing pads 923*a* to 9231 are pads for opening-closing the inlet-outlet channels for joining the channels 913*a* to 913*f* to the self-sealing type ports 917*a* to 917*l*. The joining valves between the self-sealing type ports 917*a* to 917*l* and the channels 913*a* to 913*f* are realized by these inlet-outlet pressurizing pads 923*a* to 923*l*.

Figure 75A:
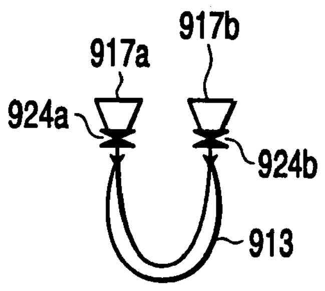
FIGS. 75A to 75D schematically show the operation for injecting solution into the nucleic acid detecting cassette under the air bubble-free state shown in FIGS. 67 and 68.
Figure 75B:
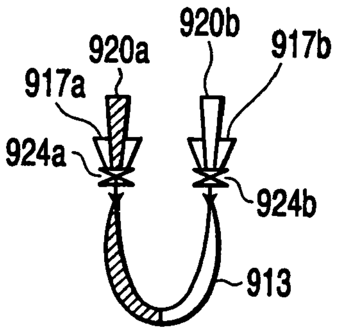
Figure 75C:
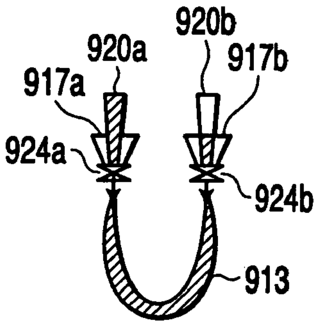
Figure 75D:
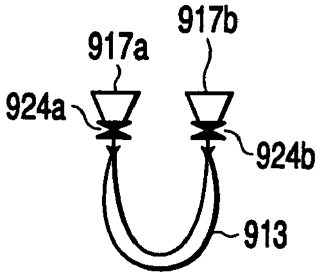

(2)-5 Fluid Injection:

FIGS. 75A to 75D are intended to explain the Air bubble-free fluid injection. As shown in FIG. 75A, the inner volume of the fluid holding channel 913 is set to the volume equal to the injecting volume by using the pressurizing pad 921*a*. In the next step, after the fluid injecting tip 920*a* and the tip 920*b* equipped with a check valve are inserted into the self-sealing type ports 917*a* and 917*b*, respectively, the solution is slowly injected so as not to catch the air bubble, as shown in FIG. 75B. Then, the solution is injected until a small amount of the solution is allowed to flow into the tip 920*b* equipped with a check valve for withdrawing the air, as shown in FIG. 75C. Further, the inlet-outlet pressurizing pads 923*a* and 923*b* are pressurized so as to close the inlet-outlet valves 924*a* and 924*b* and, thus, to completely close the fluid holding channel 913.

Figure 76:
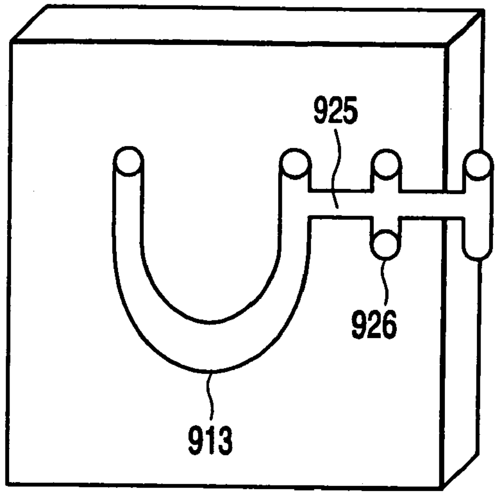
FIG. 76 schematically shows a modification of a channel for holding a reagent in the nucleic acid detecting cassette shown in FIGS. 67 and 68.

(2)-6 Individually Holding Section:

FIG. 76 shows a fluid holding channel 926 for holding a reagent according to a modification of the present invention. Where it is impossible to store a mixed reagent, the required reagent is stored in a holding section 926 serving to hold individually the reagent in the joining channel 925 joining the fluid holding channel 913 to the adjacent fluid holding channel 913, as shown in FIG. 76. Holding section 926 is provided two self-sealing type inlet-outlet ports.

Figure 77:
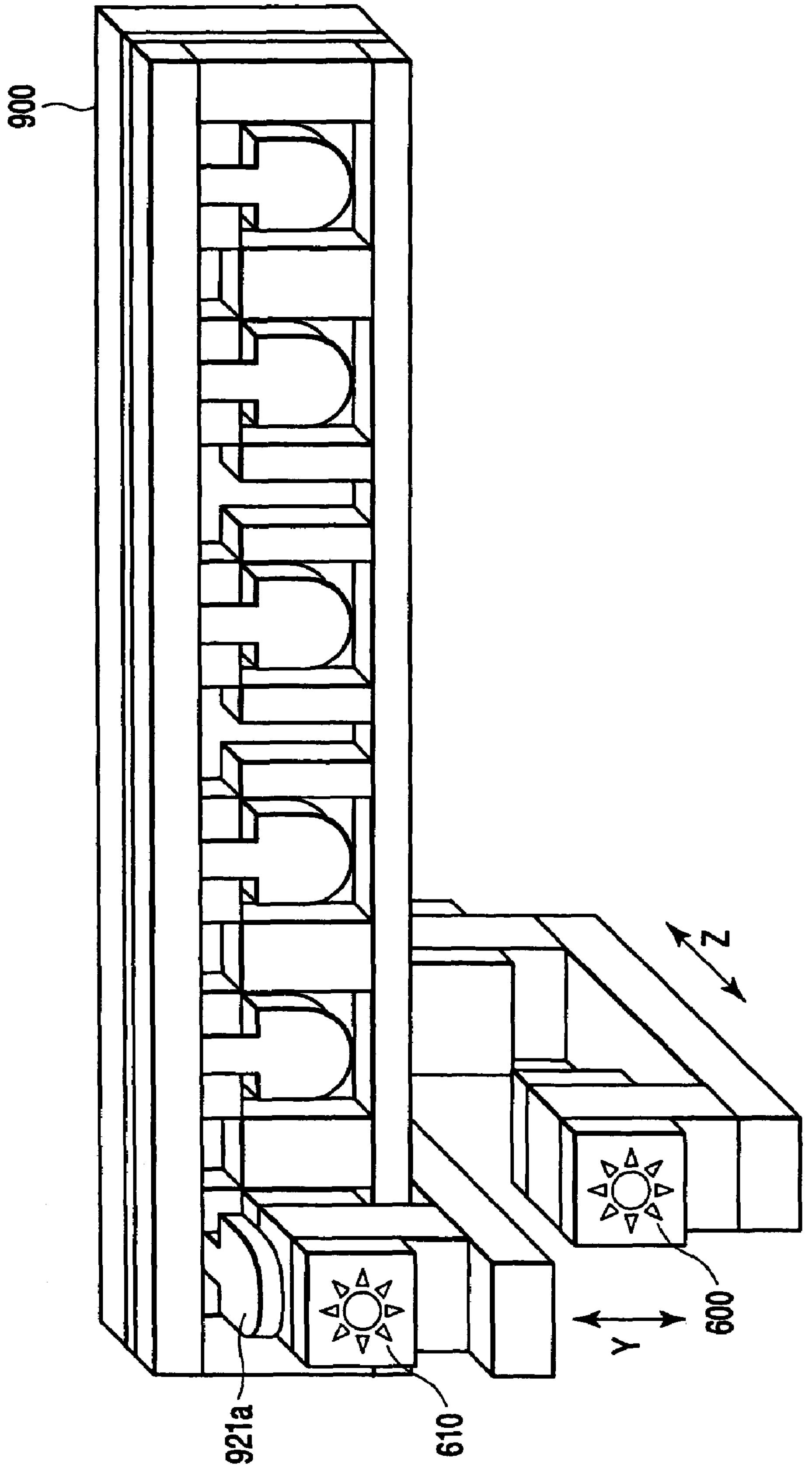
FIG. 77 is an oblique view for explaining the thermal cycling operation in the heat transfer stage in the nucleic acid detecting cassette shown in FIGS. 67 and 68.
Figure 78A:
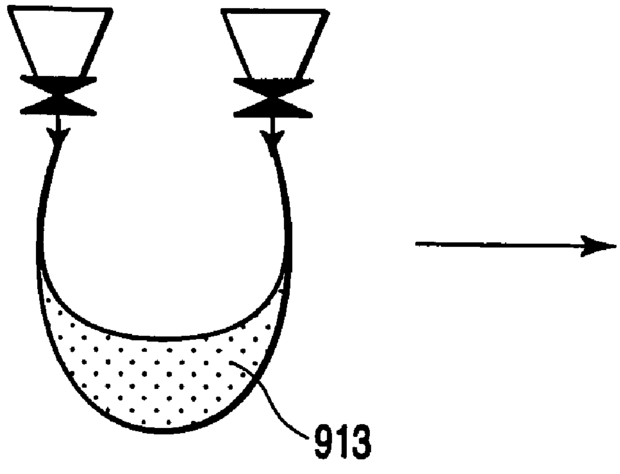
FIGS. 78A and 78B are oblique views showing in detail the state of the channel in the thermal cycling stage in the nucleic acid detecting cassette utilizing the heat transfer unit shown in FIG. 77.
Figure 78B:
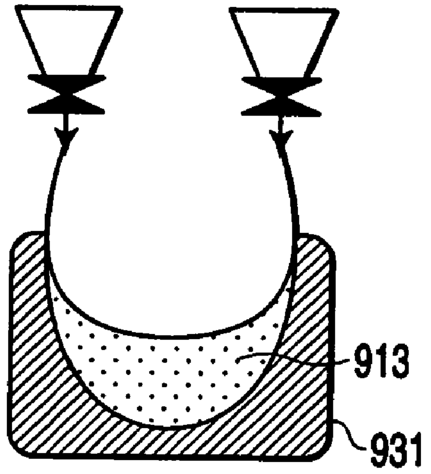

(3) Heat Transfer System:

FIG. 77 is an oblique view for explaining the thermal cycling operation in the stage of the heat transfer. The heat transfer units 610 and 600 are movable in the Y-direction and the Z-direction shown in FIG. 77. The heat transfer unit 610 is brought into contact with the front surface and the back surface of the nucleic acid detecting cassette 900 so as to permit the nucleic acid detecting cassette 900 to be positioned between the front surface and the back surface of the heat transfer unit 610. In the heat transfer stage, the heat transfer unit 610 is brought into contact with the flexible sheet 905 under the state that the channel pressurizing pad 921*a* is upheaved. FIGS. 78A and 78B schematically show in detail the channel in the thermal cycling stage. In the first step, the heat transfer unit 610 permits the solution to be concentrated in the central portion of the channel, as shown in FIG. 78A. Then, the heat transfer unit 610 is brought into contact with the front surface and the back surface of the nucleic acid detecting cassette 900 so as to repeat the cycle of heating a region 931 and, then, cooling the region 931, as shown in FIG. 78B.

Figure 79:
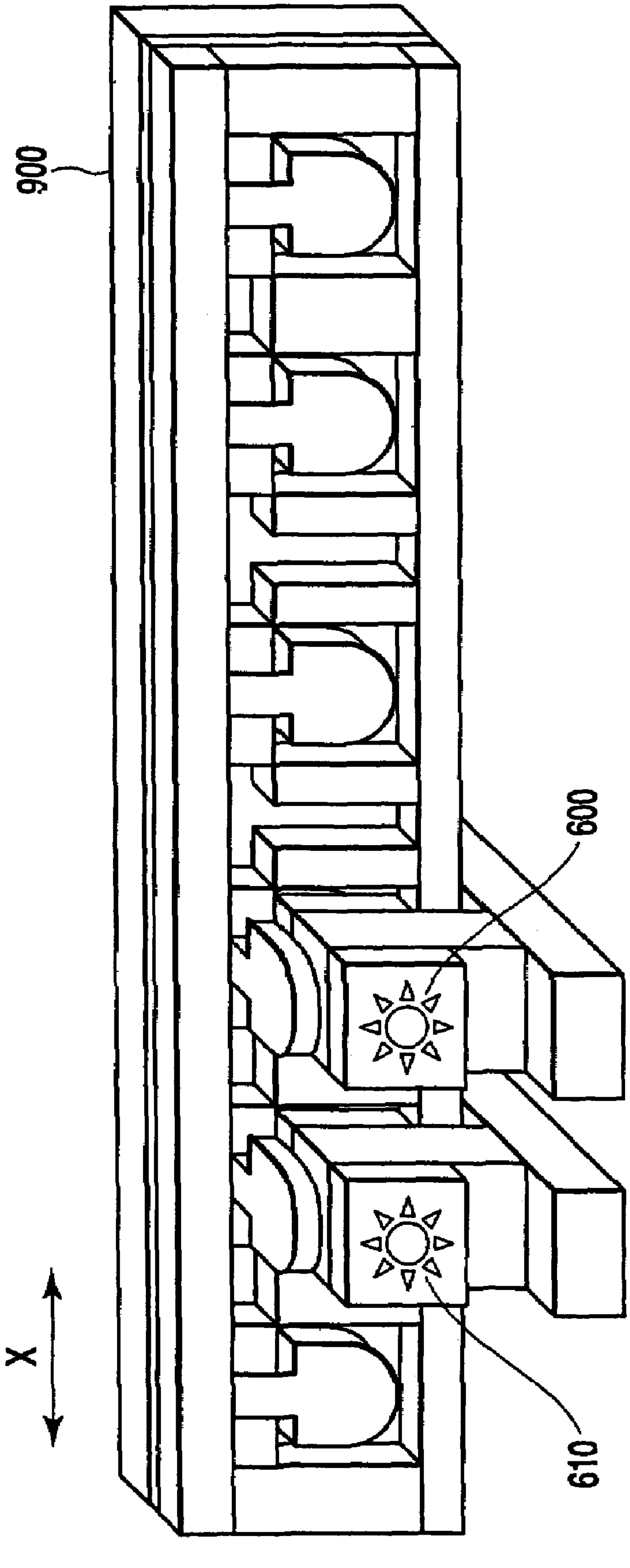
FIG. 79 is an oblique view for explaining the thermal cycling operation in the heat transfer stage in the nucleic acid detecting cassette utilizing the heat transfer unit shown in FIG. 77.

After completion of the heating•cooling of the fluid holding channel 913*a* for amplifying nucleic acid in the process shown in FIG. 78B, the nucleic acid detecting cassette 900 is moved in the direction of the X-axis as shown in FIG. 79 so as to heat and cool the adjacent fluid holding channel 913*b* and to cool the fluid holding channel 913*c*. In this fashion, the reaction is successively carried out.

Figure 80:
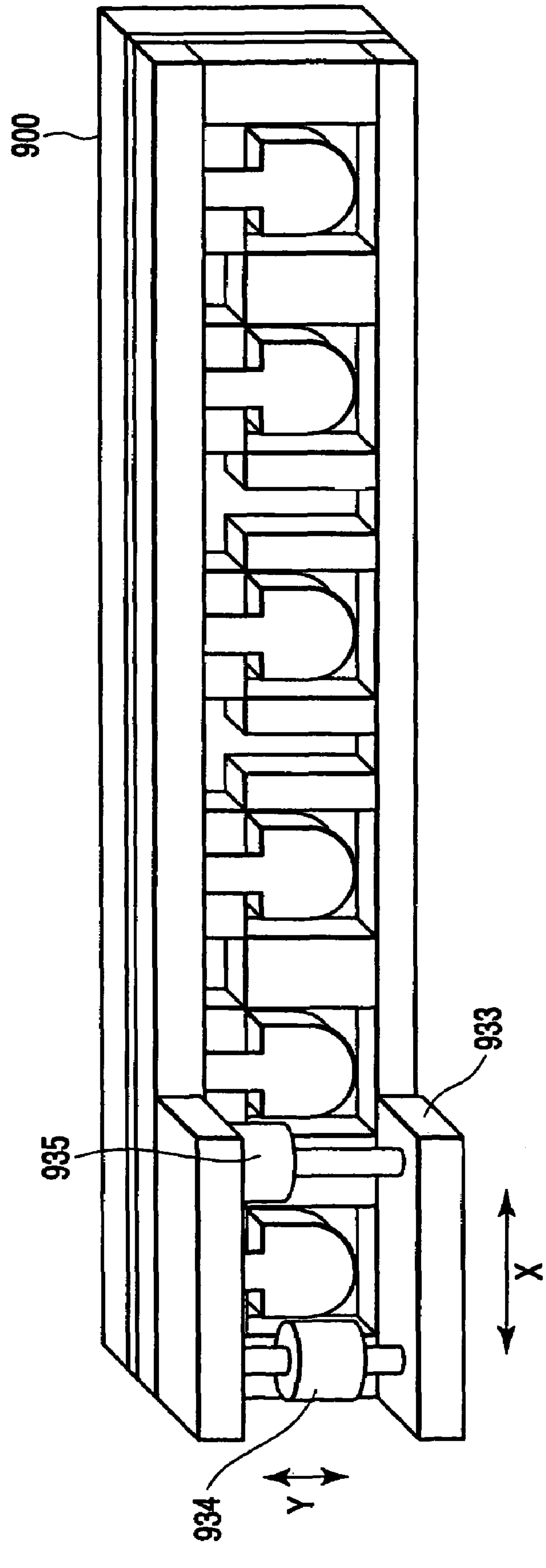
FIG. 80 is an oblique view for explaining as an example the solution transfer process in the nucleic acid detecting cassette shown in FIG. 77.

(4) Fluid Transfer System:

(4)-1 Fluid Transfer Module:

FIG. 80 is an oblique view for explaining as an example the fluid transfer process. Rollers 934 and 935 for opening-closing the pressurizing pad are mounted to a fluid transfer module 933 that is movable in a horizontal direction relative to the nucleic acid detecting cassette 900, i.e., in the direction of X-axis shown in FIG. 80. The rollers 934 and 935 noted above serve to release the locking section formed on the front surface of the nucleic acid detecting cassette 900. Alternatively, the pad is pressurized so as to lock the locking section. In this fashion, the fluid is transferred.

(4)-2 Fluid Transfer Process:

FIGS. 81A to 81D schematically show collectively the process of transferring the fluid. As shown in FIG. 81A, the joining valve 916*a* is opened so as to compress the fluid holding channel 913*a*, with the result that the transfer of the fluid is started. The channel 913*a* is not necessarily compressed uniformly by this compression. Such being the situation, the left side portion of the fluid holding channel 913*a* from which the fluid is transferred is completely compressed first, as shown in FIG. 81B. Then, the central portion of the fluid holding channel 913*a* is compressed as shown in FIG. 81C. Finally, the fluid holding channel 913*a* is completely compressed as shown in FIG. 81D, followed by closing the joining valve 916*a*.

(4)-3 Residue Removing Filter:

FIG. 82 exemplifies the construction in which a filter 937 is arranged in the fluid holding channel 913. The filter 937 is required in, for example, the case where the specimen residue after amplification of nucleic acid is transferred. Where the filter 937 is arranged in the terminating edge portion of the fluid holding channel 913, the residue is removed by the filter 937.

(5) Effect of Third Embodiment:

As described above, according to the third embodiment of the present invention, which is achieved by modifying the construction according to the first and second embodiments of the present invention, it is possible to provide a nucleic acid detecting closed cassette that can be used for the automatic continuous processing throughout the system including the amplification of nucleic acid and other required processing and the detection of the target nucleic acid as in the first and second embodiments of the present invention.

According to the present invention, all the steps including the amplification of nucleic acid and other required processing and the detection of the target nucleic acid can be automatically carried out continuously without causing the air bubbles to be taken into the liquid material.

(Effect and Modifications of all Embodiments)

As described above, the present invention is effective in the technical field of a nucleic acid detecting closed cassette and a nucleic acid detecting apparatus that can be used for the automatic continuous processing throughout the system including the amplification of nucleic acid and other required processing and the detection of the target nucleic acid. The present invention is also effective in the technical field of a nucleic acid detecting system utilizing the particular nucleic acid detecting cassette and the nucleic acid detecting apparatus utilizing the particular nucleic acid detecting cassette.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A nucleic acid detecting cassette for detecting nucleic acid contained in a sample, comprising:

a stationary member;

a flexible member provided on the stationary member, the stationary member and flexible member forming a fluid holding channel, a joining channel and an inlet-outlet port therebetween, the fluid holding channel being configured to be able to vary its inner volume, and hold a reagent, the fluid holding channel having a channel starting edge portion and a channel terminating edge portion, the inlet-outlet port being connected to the fluid holding channel and being selectively set to one of an open-state under which the fluid holding channel is communicated with the outside of the cassette through the port and a closed-state under which the fluid holding channel is discommunicated with the outside of the cassette, the joining channel being connected to the fluid holding channel, and being provided to at least one of the channel starting edge portion and the channel terminating edge portion of the fluid holding channel, the joining channel being selectively set to one of an open state under which the communication with the fluid holding channel is made and a closed-state under which the communication with the fluid holding channel is interrupted;

a first opening-closing part configured to maintain the inlet-outlet port under the closed-state; and a second opening-closing part configured to maintain the joining channel under the closed-state.

2. The nucleic acid detecting cassette according to claim 1, wherein the first opening-closing part is formed of the flexible member, and the inlet-outlet port is sealed by the flexible member.

3. The nucleic acid detecting cassette according to claim 1, wherein the second opening-closing part is formed of the flexible member, and the joining channel is sealed by the flexible member.

4. The nucleic acid detecting cassette according to claim 1, wherein:

the nucleic acid detecting cassette comprises a detecting channel formed between the stationary member and the flexible member, configured to immobilize a nucleic acid probe of a single stranded nucleic acid having a base sequence complementary to that of nucleic acid that is to be detected; and the detecting channel is connected to the fluid holding channel via the joining channel.

5. The nucleic acid detecting cassette according to claim 1, wherein the fluid holding channel includes a channel starting edge portion and a channel terminating edge portion, and the inlet-outlet port is formed in each of the channel starting edge portion and the channel terminating edge portion of the fluid holding channel.

6. The nucleic acid detecting cassette according to claim 1, wherein the first opening-closing part includes a part configured to open and close the inlet outlet port by utilizing the mobility of the flexible member.

7. The nucleic acid detecting cassette according to claim 1, wherein the second opening-closing part includes a part configured to open and close the joining channel by utilizing the mobility of the flexible member.

8. The nucleic acid detecting cassette according to claim 4, wherein the detecting channel further includes a retreating channel, in which a prescribed loading material is loaded, configured to retreat the loaded material in a detecting stage of nucleic acid in the detecting channel, the inner volume of the retreating channel being maintained under a decreased state before the start-up of the detecting stage of nucleic acid, being capable of enlargement at the time of start-up of the detecting stage, and the difference in the inner volume of the channel between enlarged time and the decreased time being not smaller than the volume of the loaded material within the detecting channel.

9. The nucleic acid detecting cassette according to claim 4, wherein a prescribed loading material is loaded in the detecting channel, and the fluid holding channel acts as a retreating channel configured to retreat the loaded material in the stage of detecting nucleic acid in the detecting channel.

10. The nucleic acid detecting cassette according to claim 4, wherein the detecting channel shares at least one of the stationary member and the flexible member collectively constituting the fluid holding channel and the joining channel.

11. The nucleic acid detecting cassette according to claim 8, wherein:

the detecting channel includes a channel starting edge portion and a channel terminating edge portion;

first and second joining channels are provided to the channel starting edge portion and the channel terminating edge portion, respectively;

the first joining channel is joined to the fluid holding channel; and the second joining channel is joined to the retreating channel.

12. The nucleic acid detecting cassette according to claim 1, further comprising a pushing member configured to push the flexible member constituting the fluid holding channel from outside the nucleic acid detecting cassette, such that the inner volume of the fluid holding channel is decreased or the inner pressure of the fluid holding channel is increased by the pushing member.

13. A nucleic acid detecting device for detecting nucleic acid contained in a sample, comprising:

a nucleic acid detecting cassette including:

a stationary member, a flexible member provided on the stationary member, the stationary member and flexible member forming a fluid holding channel, a joining channel and an inlet-outlet port therebetween, the fluid holding channel being configured to be able to vary its inner volume, the inlet-outlet port being connected to the fluid holding channel and being selectively set to one of an open-state under which the fluid holding channel is communicated with the outside of the cassette through the port and a closed-state under which the fluid holding channel is discommunicated with the outside of the cassette, the joining channel being connected to the fluid holding channel and being selectively set to one of an open-state under which the communication with the fluid holding channel is made and a closed-state under which the communication with the fluid holding channel is interrupted, a detecting channel being connected to the fluid holding channel via the joining channel, in which a prescribed loading material is loaded.

a first opening-closing part configured to maintain the inlet-outlet port under the closed-state, and a second opening-closing part configured to maintain the joining channel under the closed-state; a reagent loaded in the fluid holding channel of the nucleic acid detecting cassette; and a nucleic acid probe of a single stranded nucleic acid immobilized within the detecting channel of the nucleic acid detecting cassette and having a base sequence complementary to that of the nucleic acid to be detected.

14. The nucleic acid detecting device according to claim 13, wherein the pressure increase inside the fluid holding channel causes the flexible member to be expanded toward the outside of the nucleic acid detecting cassette so as to increase the inner volume of the fluid holding channel.

15. A nucleic acid detecting system for detecting nucleic acid contained in a sample, using a nucleic acid detecting device including:

a stationary member, a flexible member provided on the stationary member, the stationary member and flexible member forming a fluid holding channel, a joining channel and an inlet-outlet port therebetween, the fluid holding channel being configured to be able to vary its inner volume, the inlet-outlet port being connected to the fluid holding channel and being selectively set to one of an open-state under which the fluid holding channel is communicated with the outside of the cassette through the port and a closed-state under which the fluid holding channel is discommunicated with the outside of the cassette, the joining channel being connected to the fluid holding channel and being selectively set to one of an open-state under which the communication with the fluid holding channel is made and a closed-state under which the communication with the fluid holding channel is interrupted, a detecting channel being connected to the fluid holding channel via the joining channel capable of immobilizing a nucleic acid probe of a single stranded nucleic acid having a base sequence complementary to that of nucleic acid that is to be detected, a first opening-closing part configured to maintain, the inlet-outlet port under the closed-state, and a second opening-closing part configured to maintain the joining channel under the closed-state; the nucleic acid detecting system comprising: a device holding part configured to hold the device;

a first driving mechanism configured to deform a first part of the flexible member corresponding to a first region of the fluid holding channel within the device held by the device holding part so as to deform the fluid holding channel;

a second driving mechanism configured to deform a second part of the flexible member corresponding to a second region of the fluid holding channel within the device held by the device holding part so as to deform the fluid holding channel;

a third driving mechanism configured to drive the second opening-closing part; and a temperature control part configured to control the temperature of at least one of the fluid holding channel and the detecting channel.

16. The nucleic acid detecting system according to claim 15, wherein at least two of the first driving mechanism, the second driving mechanism, and the third driving mechanism are formed of a common driving mechanism.

17. The nucleic acid detecting system according to claim 15, wherein:

the fluid holding channel includes a first fluid holding channel and a second fluid holding channel;

the joining channel serves to join the first fluid holding channel and the second fluid holding channel to each other; and the temperature control part includes a first temperature control part configured to control the temperature of the first fluid holding channel and a second temperature control part configured to control the temperature of the second fluid holding channel.

18. The nucleic acid detecting system according to claim 15, wherein:

the joining channel serves to join the fluid holding channel and the detecting channel to each other; and the temperature control part includes a first temperature control part configured to control the temperature of the fluid holding channel and a second temperature control part configured to control the temperature of the detecting channel.

19. The nucleic acid detecting system according to claim 15, wherein:

the device includes a pushing member configured to push the flexible member constituting the fluid holding channel from outside the device; and the nucleic acid detecting system further includes a part configured to allow the pushing member to be selectively located in a position facing the surface of the flexible member constituting the fluid holding channel and a position retreating from the surface of the flexible member, the temperature control part being selectively positioned close to, brought into contact with and pushed against the surface of the flexible member when the pushing member is in the retreating position.

20. The nucleic acid detecting system according to claim 15, wherein:

the device includes at least two fluid holding channels and detecting channels arranged in series, and the temperature control part includes a first temperature control part configured to control the temperature of one of one fluid holding channel and one detecting channel and a second temperature control part configured to control the temperature of one of the other fluid holding channel and the other detecting channel.

* * * * *